(12) United States Patent
Reiley et al.

(10) Patent No.: US 8,632,483 B2
(45) Date of Patent: Jan. 21, 2014

(54) SYSTEMS, DEVICES, AND METHODS FOR MECHANICALLY REDUCING AND FIXING BONE FRACTURES

(75) Inventors: Mark A Reiley, Washington, DC (US); Kurt Vedder, Danville, CA (US); Colin J. Corey, Walnut Creek, CA (US)

(73) Assignee: Fixes 4 Kids Inc., Salt Lake City, UT (US)

( * ) Notice: Subject to any disclaimer, the term of this patent is extended or adjusted under 35 U.S.C. 154(b) by 54 days.

(21) Appl. No.: 13/292,653

(22) Filed: Nov. 9, 2011

(65) Prior Publication Data
US 2012/0289879 A1 Nov. 15, 2012

Related U.S. Application Data

(63) Continuation-in-part of application No. 13/051,774, filed on Mar. 18, 2011.

(60) Provisional application No. 61/443,080, filed on Feb. 15, 2011, provisional application No. 61/396,562, filed on May 28, 2010.

(51) Int. Cl.
*A61F 5/00* (2006.01)

(52) U.S. Cl.
USPC .................................. 602/16; 602/23; 602/27

(58) Field of Classification Search
USPC ................ 602/16, 23, 27, 32–39; 606/54–59; 128/882
See application file for complete search history.

(56) References Cited

U.S. PATENT DOCUMENTS

| | | | | |
|---|---|---|---|---|
| 4,889,111 A * | 12/1989 | Ben-Dov | ......................... | 606/56 |
| 4,988,349 A * | 1/1991 | Pennig | ............................ | 606/58 |
| 5,099,992 A * | 3/1992 | Heimreid | ...................... | 206/366 |
| 7,422,593 B2 * | 9/2008 | Cresina et al. | .................. | 606/54 |
| 7,588,571 B2 * | 9/2009 | Olsen | .............................. | 606/57 |

* cited by examiner

*Primary Examiner* — Michael A. Brown
(74) *Attorney, Agent, or Firm* — Ryan Kromholz & Manion, S.C.

(57) ABSTRACT

A frame is sized and configured to support a reduced bone fracture of an individual. A guide assembly on the frame carries a bone fixing device guide that defines a guide path along which a bone fixing device can be advanced into a region of the reduced bone fracture. A linkage system couples the bone fixing device guide to the frame for articulation of the guide path among a plurality of desired orientations with respect to the reduced bone fracture. A guide bushing is included. Which includes packaging that maintains the guide bushing in a sterile condition prior to insertion into the bone fixing device guide.

17 Claims, 62 Drawing Sheets

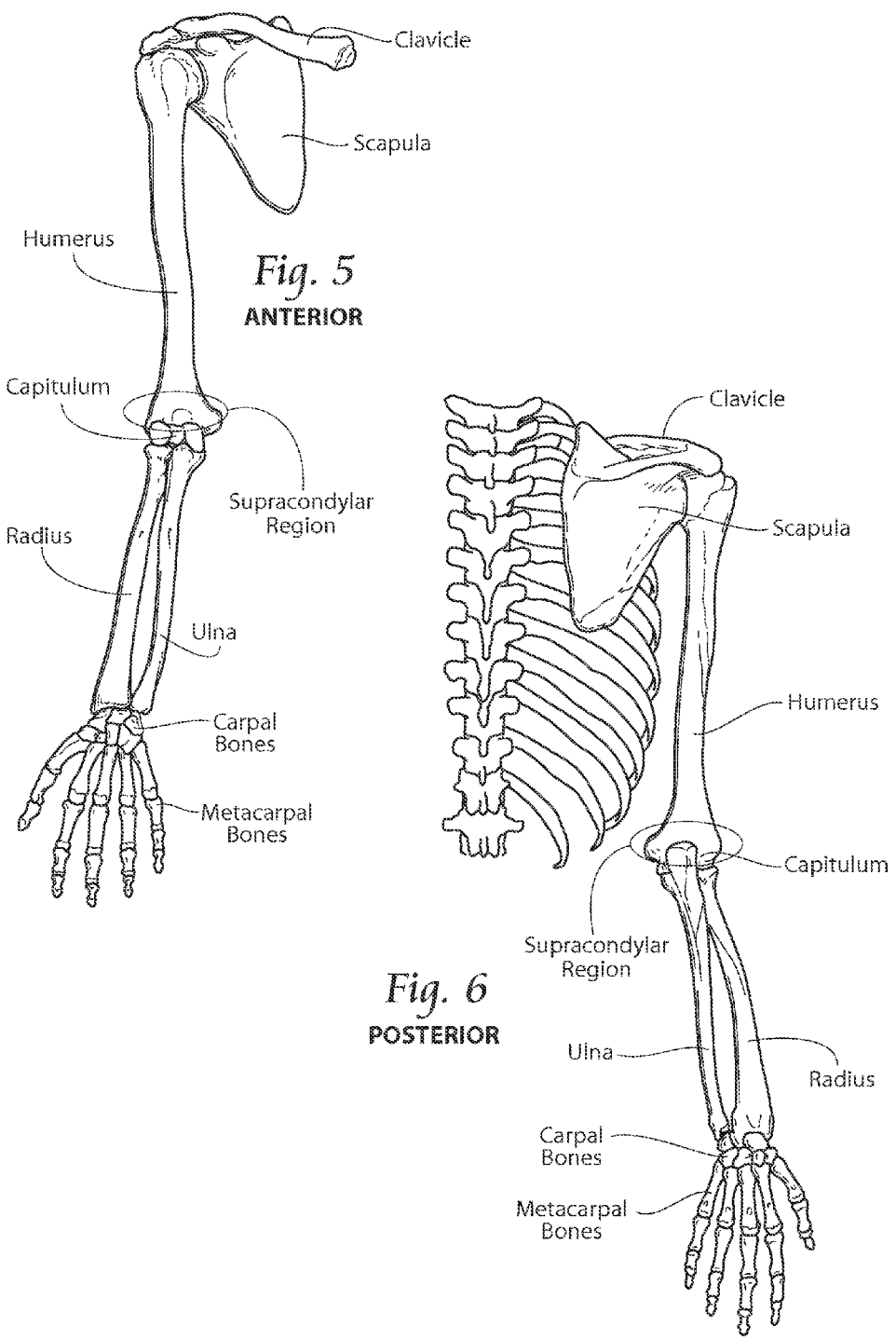

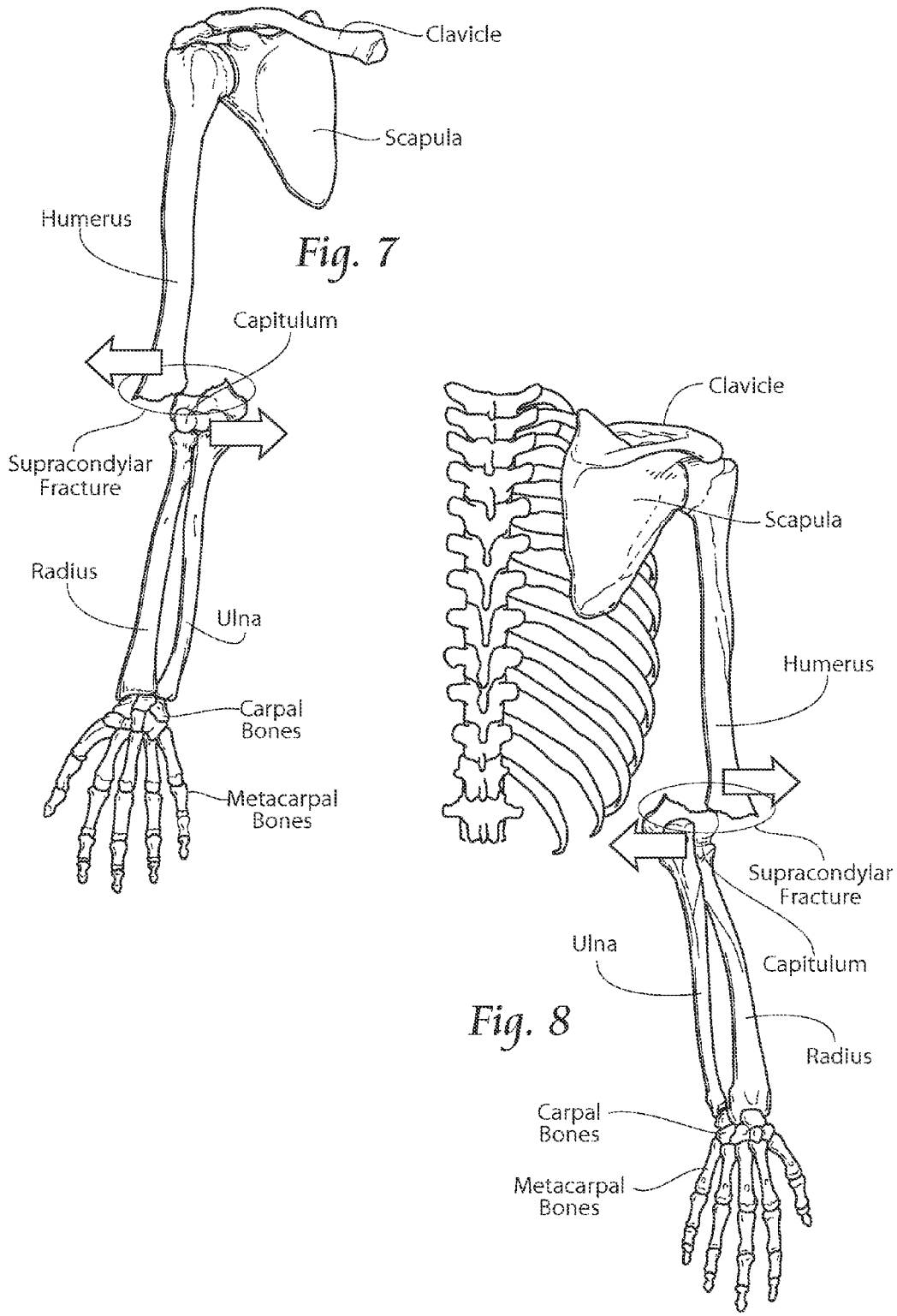

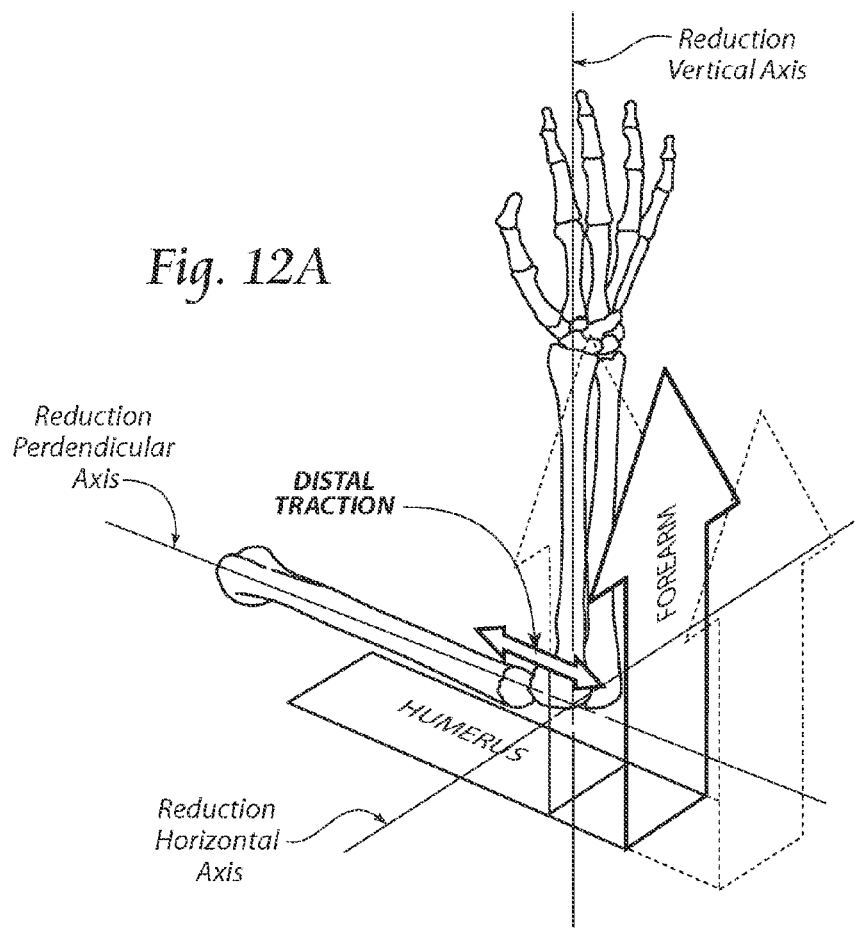
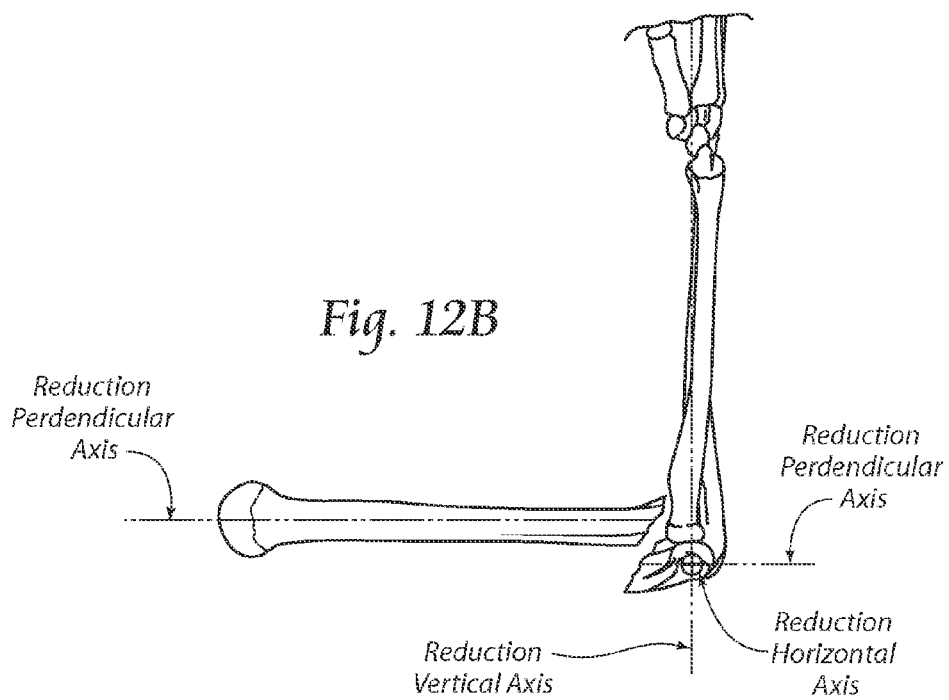

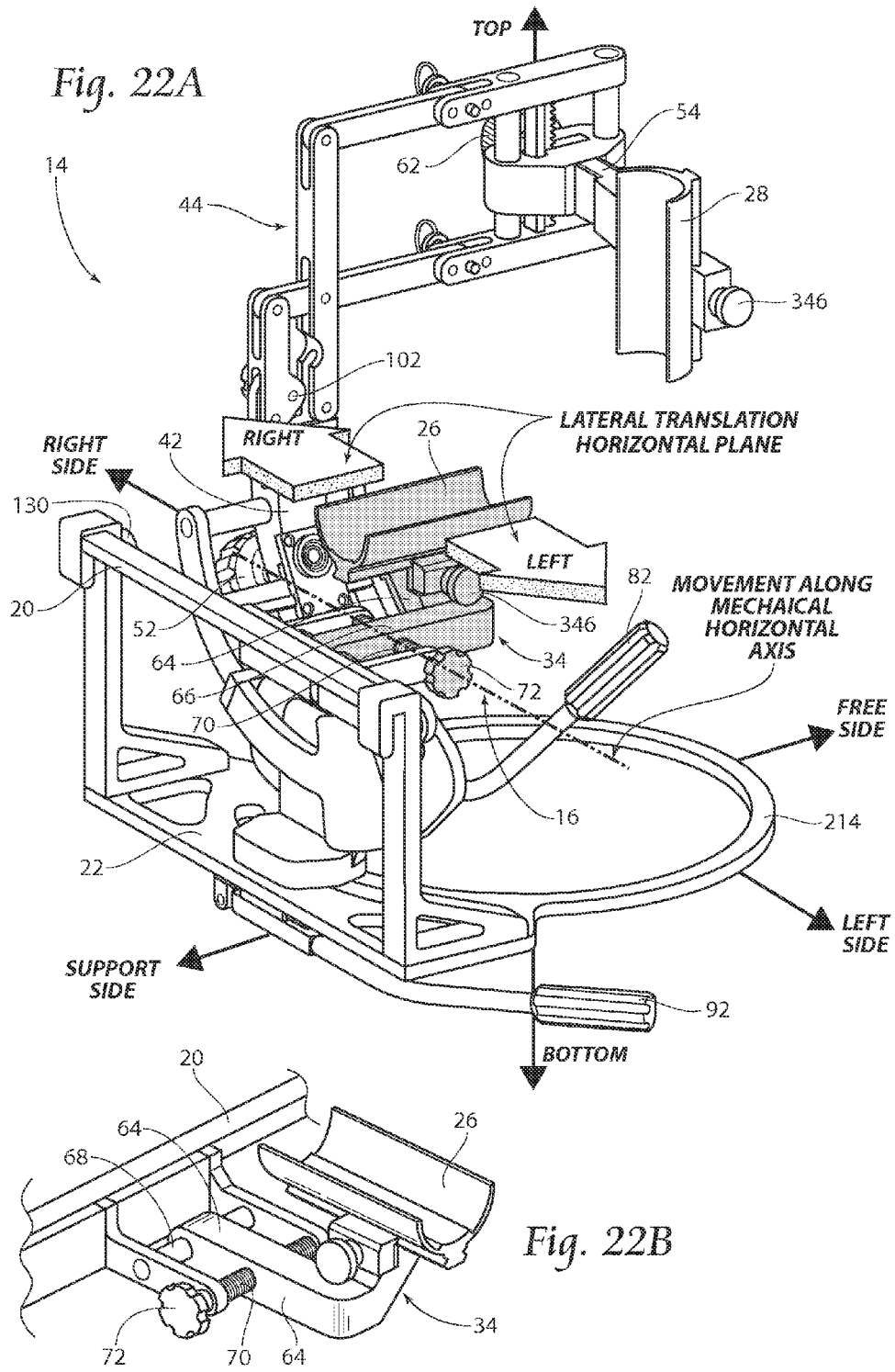

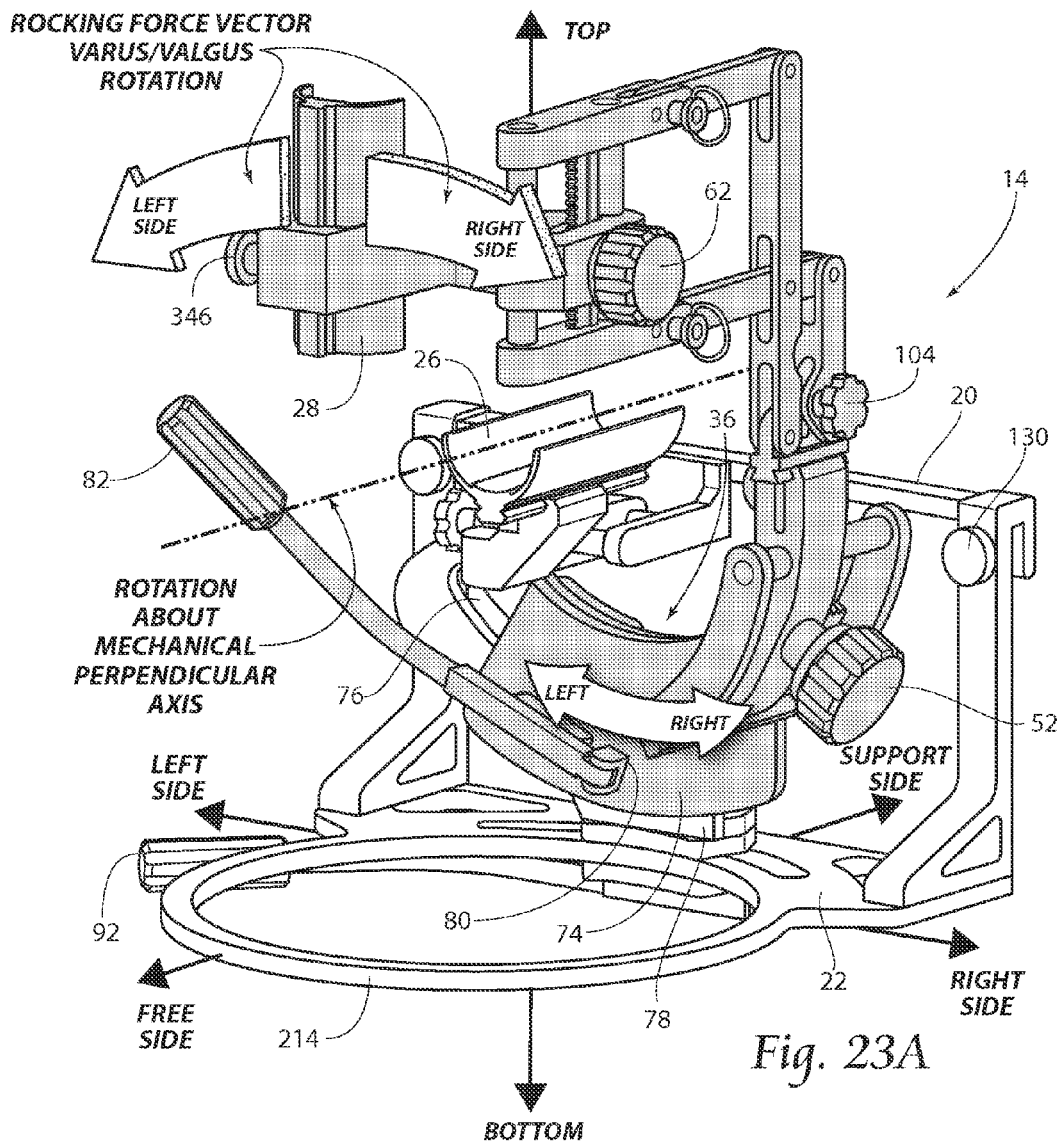
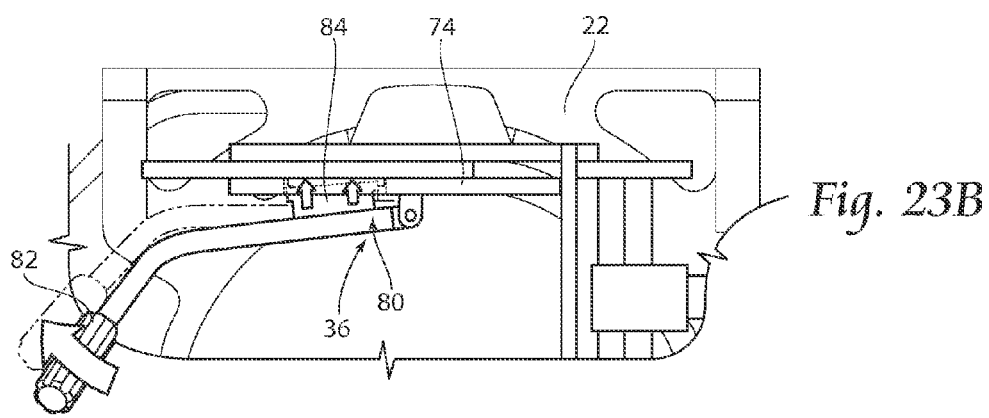
Fig. 23A
Fig. 23B

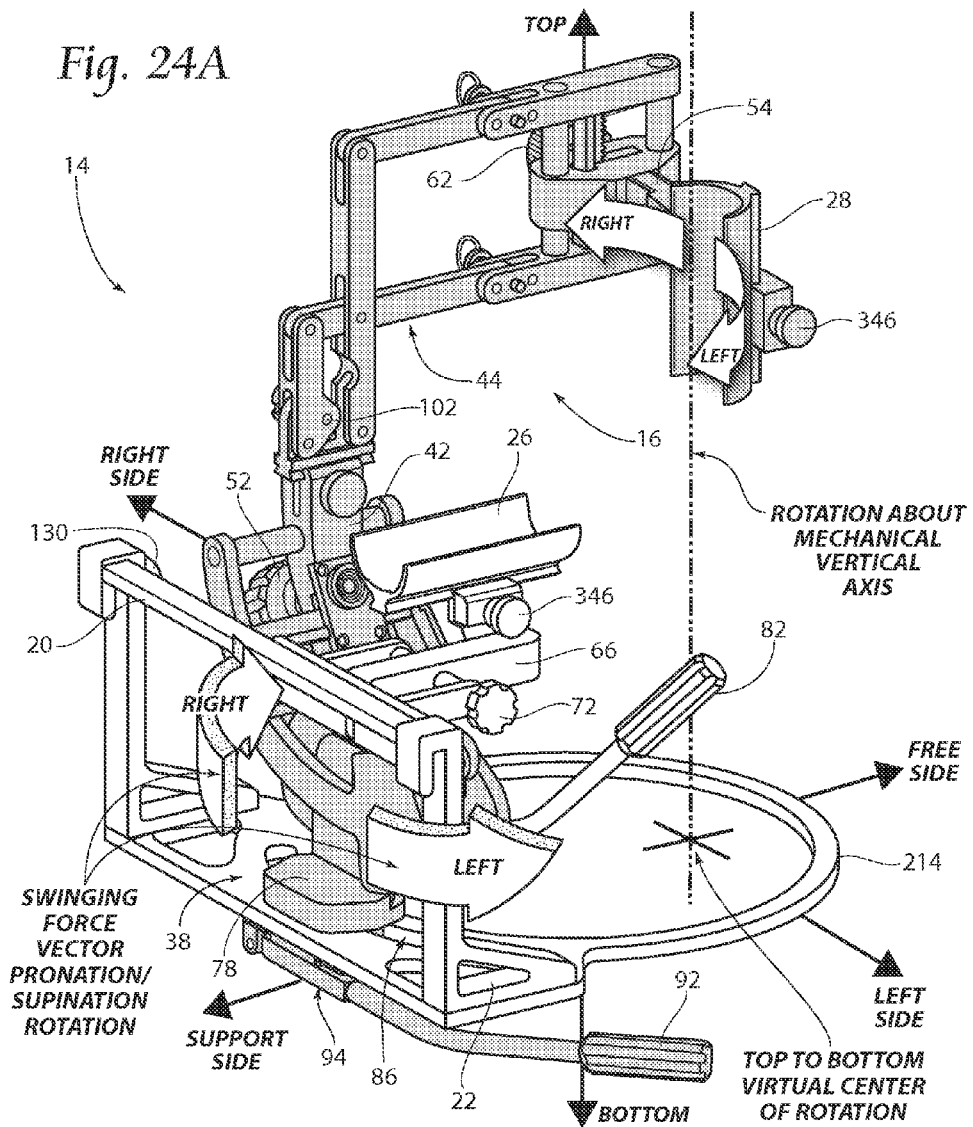
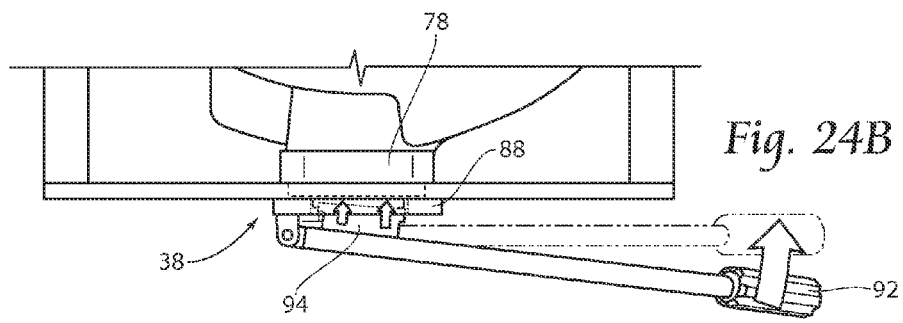

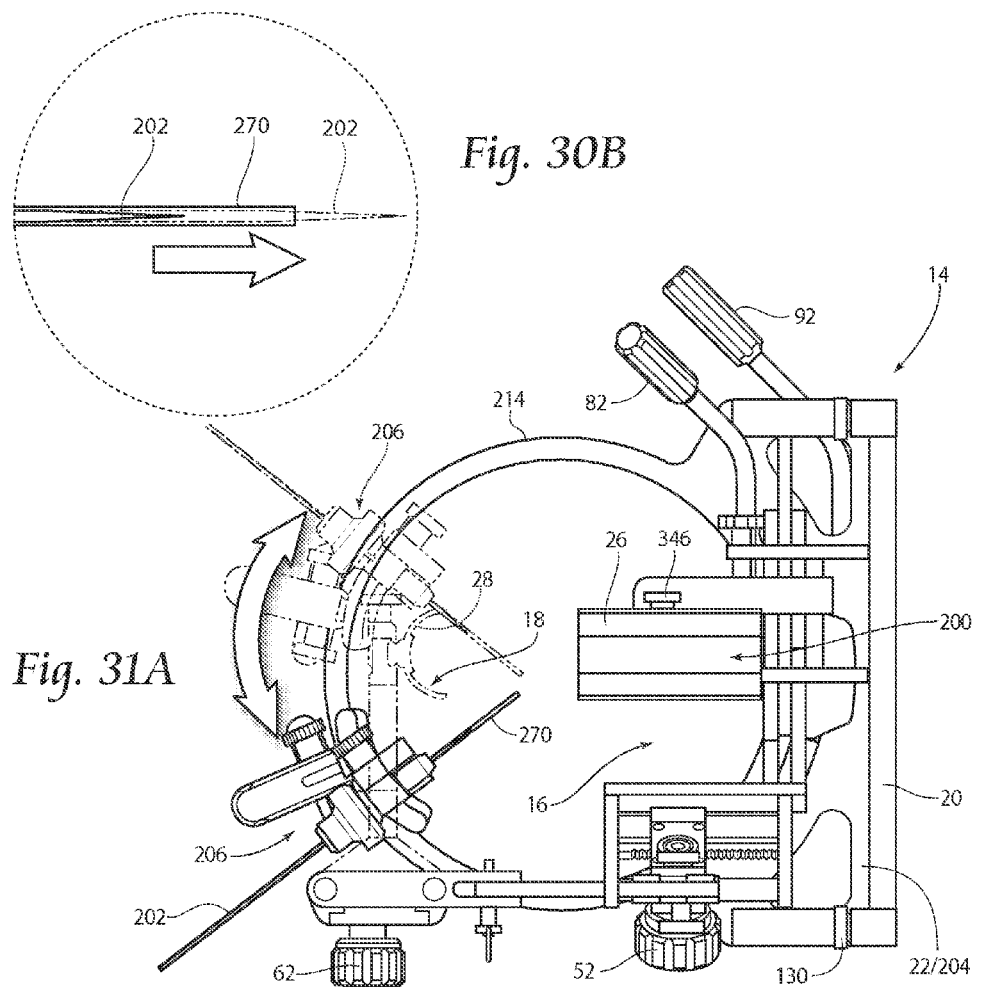
*Fig. 30B*
*Fig. 31A*
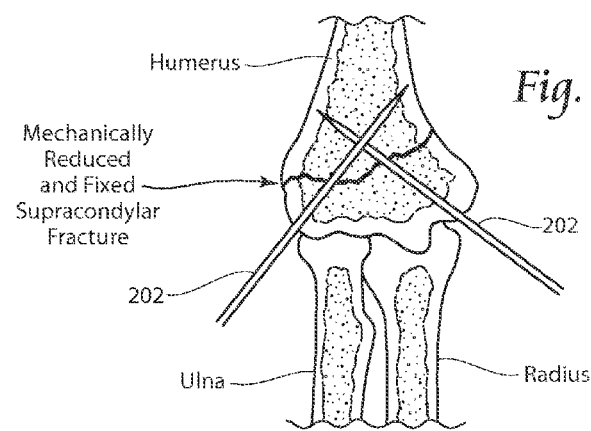
*Fig. 31B*

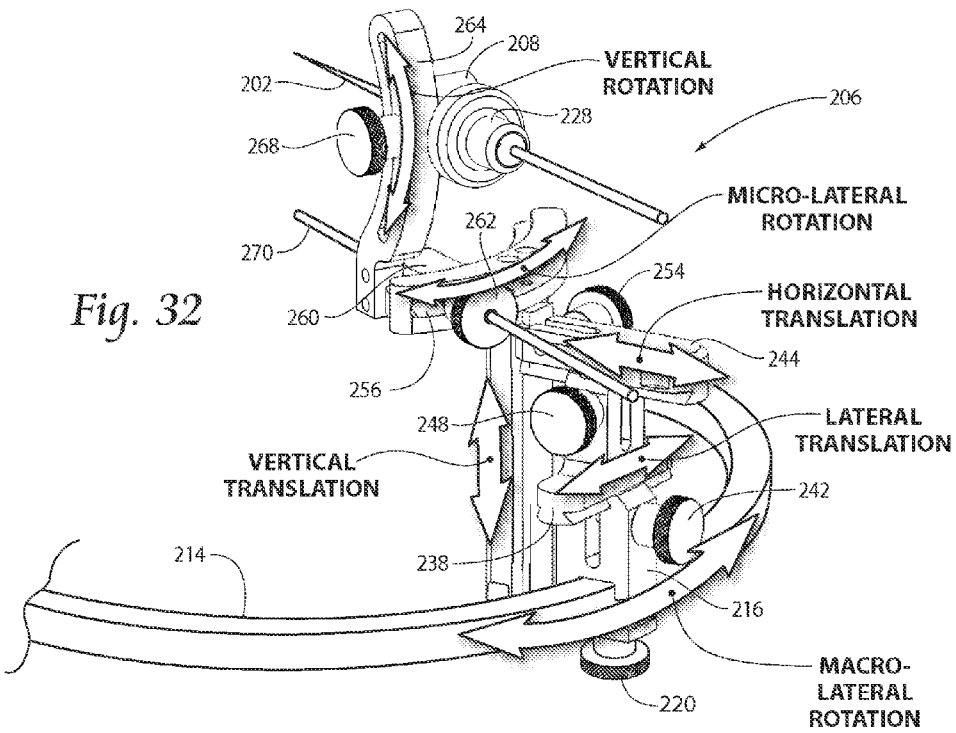
Fig. 32
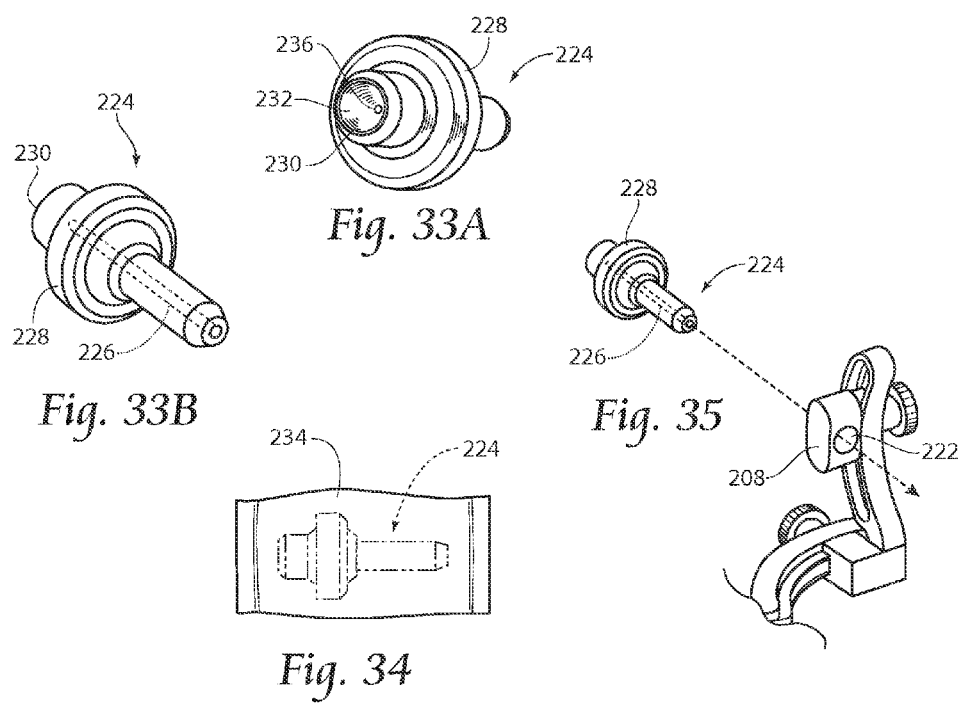
Fig. 33A
Fig. 33B
Fig. 34
Fig. 35

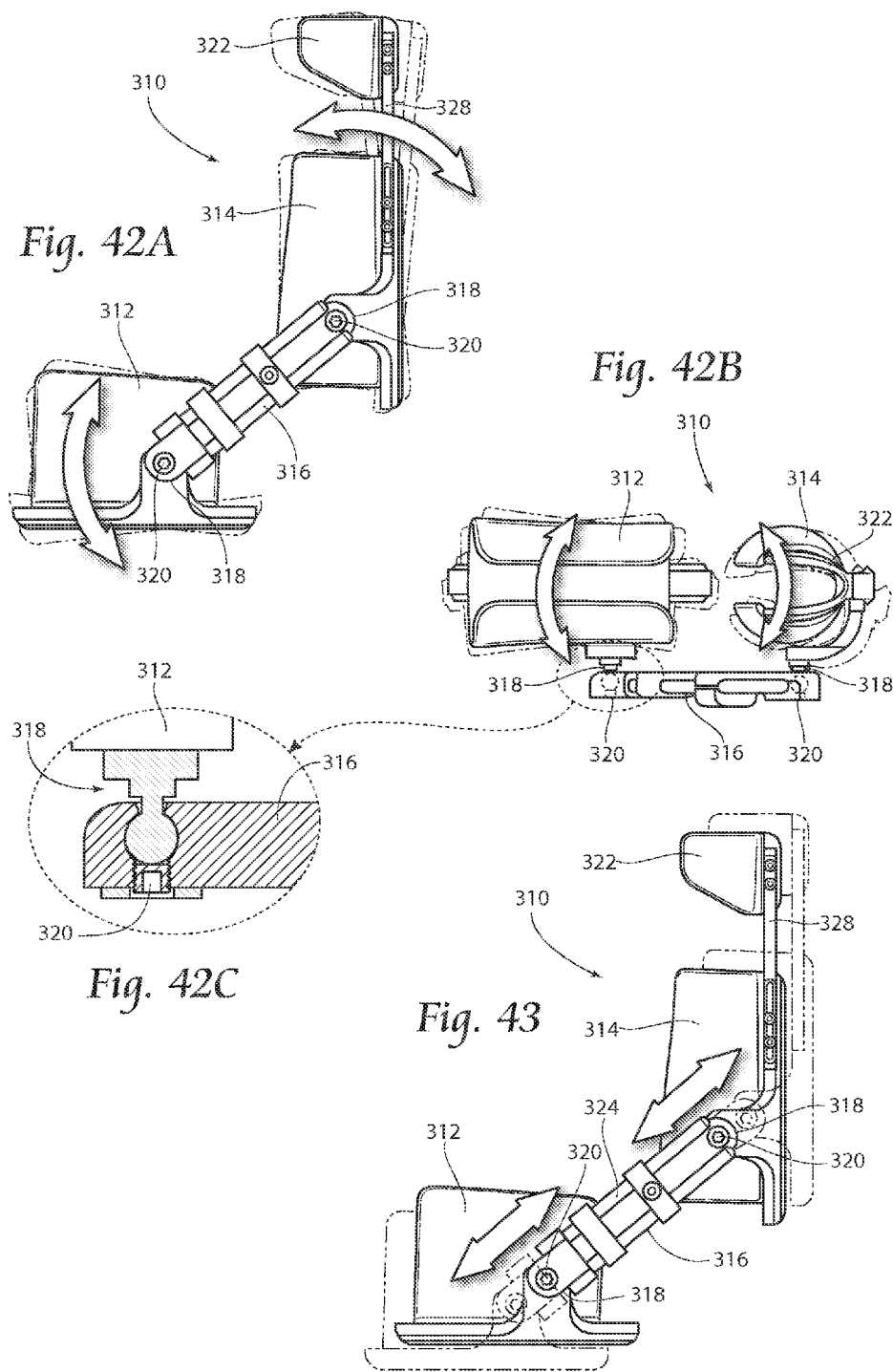

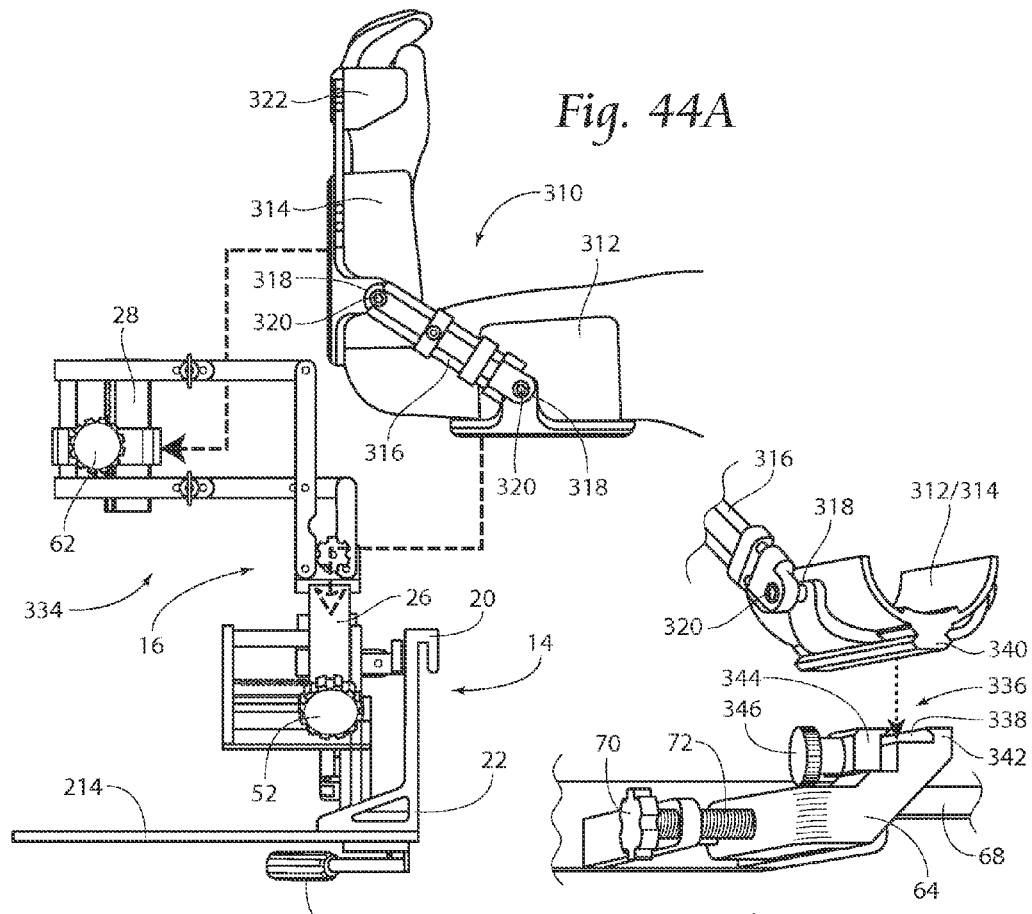
Fig. 44A
Fig. 44B
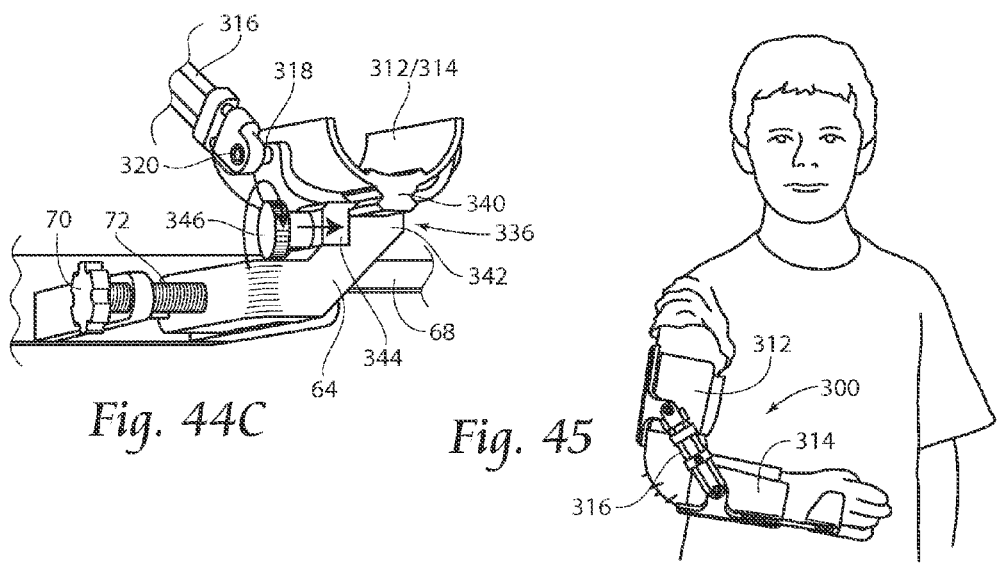
Fig. 44C
Fig. 45

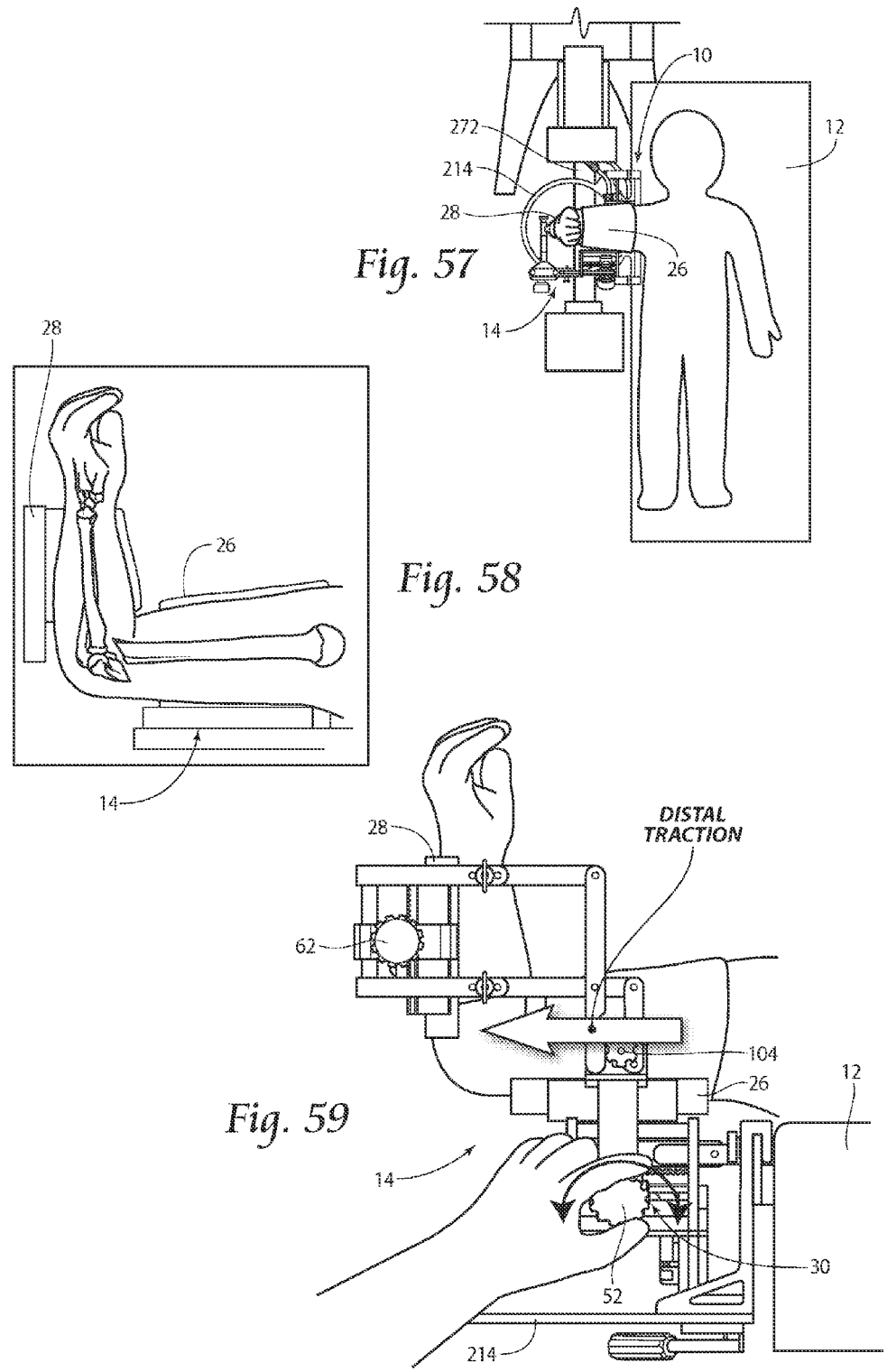

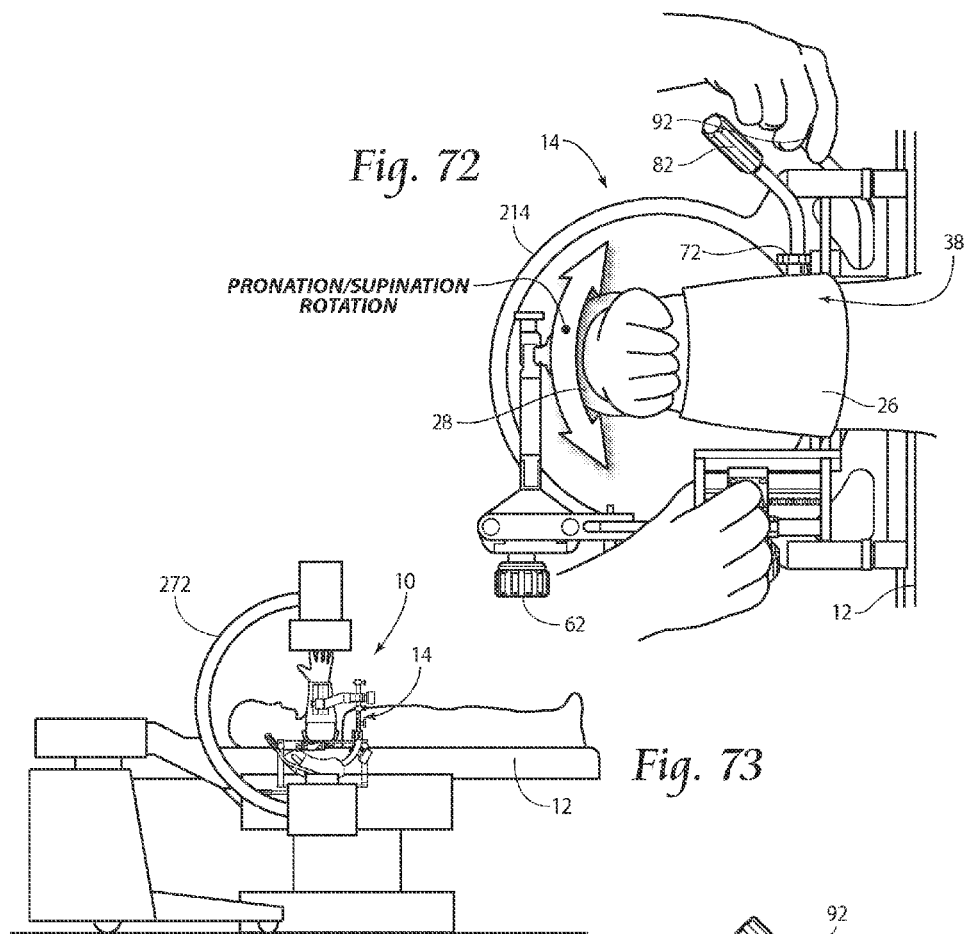
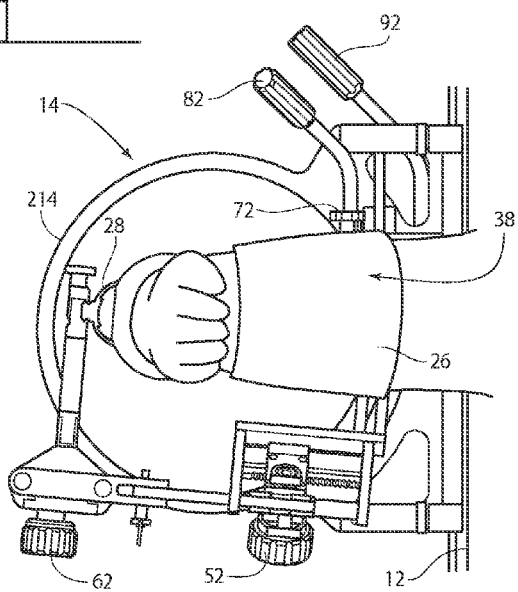

SYSTEMS, DEVICES, AND METHODS FOR MECHANICALLY REDUCING AND FIXING BONE FRACTURES

RELATED APPLICATIONS

This application is a continuation-in-part of co-pending U.S. application Ser. No. 13/051,774, filed on Mar. 18, 2011, which claims priority to of U.S. Provisional Patent Application Ser. No. 61/443,080, filed Feb. 15, 2011, entitled "Systems, Devices, and Methods, for Mechanically Reducing and Fixing Bone Fractures," which is incorporated herein by reference. This application also claims the benefit of U.S. Provisional Application No. 61/396,562, filed May 28, 2010, entitled "Apparatus and Method for Reduction and Stabilization of Bone Fractures," which is incorporated herein by reference.

FIELD OF THE INVENTION

The invention generally relates to systems, devices and methods for reducing and fixing bone fractures.

BACKGROUND OF THE INVENTION

Bone fractures can occur in various regions of the body, and affect both children and adults. Bone fractures can occur, e.g., in the arm, involving the humerus and/or forearm and/or wrist; in the leg, involving the tibia and/or fibula; or at, in, or near articulating condyles (also called a condular fracture), e.g. at, in, or near the elbow, or at, in, or near the knee.

Under some circumstances bone fractures may require more intensive treatment than simple immobilization. For example, due to the severity of the fracture, certain bone fractures may require surgical reducing and fixing, including placement of pins, screws, or other fixation devices, which must be precisely positioned to ensure that the fracture is properly reduced (i.e., aligned) and fixed during recovery and healing.

By way of example, several different treatment options exist for condylar fractures above the elbow, called supracondylar fractures. A supracondylar fracture is shown in FIGS. 7 and 8. Supracondylar fractures are relatively common in children, and may occur for example, when a child falls onto an outstretched arm. Fractures of this type may be classified according to the degree of fracture region separation, with the resultant treatment being predicated upon the fracture classification.

For example, Type 1 fractures are un-displaced or minimally displaced fractures, such as hairline fractures and are treated with simple immobilization in a cast without any manipulation. Type 2 fractures are partially displaced such that the regions are nearly aligned, with some bony contact present. This type is typically treated by manipulation followed by immobilization in a cast. Type 3 fractures (see, e.g., FIGS. 7 and 8) are completely displaced with fracture regions far apart from each other.

In known methods for treating type 2 and 3 fractures (see FIGS. 1 to 3), the current standard of care is, by manual manipulation of the arm (see FIG. 1), a surgeon attempts to return the fractured bone regions to an anatomically normal alignment, which can also be called "manual reduction." Following manual reduction, the fracture is "fixed" (see FIG. 2), during which the surgeon will hold the manually reduced bone regions in place and insert pins or other fixation device, while checking radiographs to verify pin placement, to prevent the manually reduced bone regions from moving out of alignment during the healing process (see FIG. 3).

In the current standard of care, both manual reduction and fixing are performed "free hand" with the aid of radiation imaging. The current standard of care is, at best, problematic in several respects. First, by free hand manual manipulation, the surgeon can at best only approximate a complete anatomic reduction of a complex fracture in all anatomic planes. Manual reduction competes against itself: manually bringing the fracture into alignment in one anatomic plane, can move the fracture out of alignment in another anatomic plane. Second, the surgeon must by free hand manual manipulation attempt to hold the free hand reduction in place, while also in a free hand fashion simultaneously insert the pins to fix the reduction. A loss of manual reduction, imperfect to begin with, occurs. As a result, the current standard of care is frequently inaccurate, with patient injury resulting from incomplete reduction. Third, the repeated radiation imaging of the fracture during manual reduction and pin placement process exposes both the patient and the surgeon's hands again and again to radiation.

While the traditional manual treatment method is effective in some instances, exposure of the fracture through an open incision is often required. Such treatment is invasive. Further, operative time for these difficult to treat fractures may become lengthy and exceed seven hours.

Due to the obvious risks involved, improvement in manual fracture reduction and fixation is desired.

SUMMARY OF THE INVENTION

The invention provides devices, systems, and methods for mechanically fixing bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condylar fracture), e.g. at, in, or near the elbow, or at, in, or near the knee.

According to one aspect of the invention, the devices, systems, and methods include a frame that is sized and configured to support a reduced bone fracture of an individual. The devices, systems, and methods include a guide assembly on the frame including a bone fixing device guide that defines a guide path along which a bone fixing device can be advanced into a region of the reduced bone fracture. The guide assembly includes a linkage system that couples the bone fixing device guide to the frame for articulation of the guide path among a plurality of desired orientations with respect to the reduced bone fracture. The devices, systems, and methods also include a guide bushing having an interior channel for passing a bone fixing device. The guide bushing is sized and configured to be handled separate from the guide assembly for insertion into the guide path of the bone fixing device guide at the instance of use and for separation from the guide path after use. The devices, systems, and methods also include packaging that maintains the guide bushing in a sterile condition prior to insertion into the guide path. The modular, sterile guide bushing makes possible the sterile insertion of a bone fixing device using the mechanical guidance mechanism, without the need to sterilize the entire mechanical guidance mechanism.

In one embodiment, the interior channel of the guide bushing includes an entrance end for receiving the bone fixing device for passage. The entrance end comprising a funnel shaped entrance surface that directs the bone fixing device directly into the interior channel. In this arrangement, the funnel shaped entrance surface shields contact with the interior channel prior to use.

The guide bushing can be disposable, or the guide bushing can be returned to a sterile condition and repackaged after use.

In one embodiment, the linkage system of the guide assembly includes first and second links. The first link articulates the bone fixing device guide in a first plane, including a mechanism that is sized and configured to mechanically interact with the first link to maintain a desired articulation in the first plane. The second link articulates the bone fixing device guide in a second plane different than the first plane, including a mechanism that is sized and configured to mechanically interact with the second link to maintain a desired articulation in the second plane without altering the desired articulation in the first plane. In one embodiment, the linkage system includes a third link that articulates the bone fixing device guide in a third plane that intersects one of the first and second planes at an angle. The third link includes a mechanism that is sized and configured to mechanically interact with the third link to maintain a desired articulation in the third plane without altering the desired articulations in the first and second planes.

According to another aspect of the invention, the devices, systems, and methods further include at least one fracture reduction mechanism on the frame that is sized and configured to apply at least one mechanical force vector to maintain the reduced bone fracture in at least one desired anatomic orientation during articulation of the guide path of the bone fixing device guide. In this arrangement, the frame carries both a fracture reduction mechanism and a fixing guide assembly to achieve systematic mechanical reduction and fixing of the bone fracture.

According to another aspect of the invention, the devices, systems, and methods further include an orthotic brace that is sized and configured to be fitted on the frame to a region of the reduced bone fracture.

In one embodiment, the invention provides devices, systems, and methods can be applied for mechanically fixing a fractured supracondylar region following a reduction.

Other objects, advantages, and embodiments of the invention are set forth in part in the description which follows, and in part, will be obvious from this description, or may be learned from the practice of the invention.

BRIEF DESCRIPTION OF THE DRAWINGS

FIGS. 5 and 6 are, respectively, an anterior and a posterior view of the supracondylar region and adjoin bone structures in a right human arm.

FIGS. 7 and 8 are, respectively, an anterior and a posterior view of bone structures in the right human arm, like that shown in FIGS. 5 and 6, but also showing a supracondylar fracture, showing left-right displacement of the proximal and distal bone regions of the fracture.

FIGS. 12A to 12D are anatomic and partially schematic views of a right human arm with a supracondylar fracture, demonstrating the application of a force reduction vector comprising distal traction.

FIGS. 22A to 22D are, respectively, a Support Side perspective view, an enlarged partial perspective view, and companion Top views of the mechanical bone reduction fixture shown in FIGS. 19A to 19F, with the principal components that function to achieve lateral translation shaded for identification, and also identifying in FIGS. 22A, 22C, and 22D the directional points of reference and the principal mechanical axis of movement for lateral translation, consistent with FIG. 19A.

FIGS. 23A to 23D are, respectively, a Free Side perspective view, an enlarged partial Top view, and companion Free Side elevation views of the mechanical bone reduction fixture shown in FIGS. 19A to 19F, with the principal components that function to achieve varus/valgus rotation shaded for identification, and also identifying in FIGS. 23A, 23C, and 23D the directional points of reference and the principal mechanical axis of movement for varus/valgus rotation, consistent with FIG. 19A.

FIGS. 24A to 24E are, respectively, a Support Side perspective view, an enlarged partial Top view, an enlarged partial Free Side View, and companion Top views of the mechanical bone reduction fixture shown in FIGS. 19A to 19F, with the principal components that function to achieve pronation/supination rotation shaded for identification, and also identifying in FIGS. 24A, 24D, and 24E the directional points of reference and the principal mechanical axis of movement for pronation/supination rotation, consistent with FIG. 19A.

FIG. 30B is an illustration of a radiographic image showing a bone fixing device being advanced under the guidance by an a-p guide pin, which has been oriented by manipulation the pin guide assembly shown in FIGS. 29 and 30A.

FIG. 31A is a Top view of the pin guide assembly shown in FIGS. 27 and 28 mounted for use an alignment rail in association with a mechanical bone reduction fixture as shown in FIGS. 19A to 19F, showing the mechanical orientation and guidance of a bone fixing device by the pin guide assembly for fixing a supracondylar fracture following reduction.

FIG. 31B is an anatomic side section view of a reduced supracondylar fracture following insertion of two bone fixing devices under guidance by the pin guide assembly shown in FIGS. 27 and 28 to fix the reduction.

FIG. 32 is a perspective view of the pin guide assembly shown in FIGS. 27 and 28 mounted for use an alignment rail, also identifying the translation of the bone fixing device guide by the pin guide assembly in different horizontal, vertical, and rotational paths.

FIGS. 33A and 33B are perspective end views of a guide bushing that can be mounted at the instance of use in a sterile condition on the bone fixing device guide of the pin guide assembly shown in FIGS. 27 and 28.

FIG. 34 is a top view of the guide bushing shown in FIGS. 33A and 33B packaged in a sterile condition within a pouch prior to use in association with the pin guide assembly.

FIG. 35 is an exploded perspective view of the mounting of the guide bushing shown in FIGS. 33A and 33B on the bone fixing device guide of the pin guide assembly shown in FIGS. 27 and 28 at the instance of use.

FIGS. 42A and 42B are side elevation views of the orthotic brace shown in FIG. 39, showing the articulation of the proximal and distal brace components within a range of rotational orientations to accommodate forces applied to reduce the fracture.

FIG. 42C is an enlarged view (in section) of the articulating linkage and associated locking mechanism of the orthotic brace shown in FIGS. 42A and 42B, which accommodate the rotational orientations shown in FIGS. 42A and 42B and the ability to maintain a desired rotational orientation within the range to maintain a desired reduction of the fracture.

FIG. 43 is a side elevation view of the orthotic brace shown in FIG. 39, demonstrating the ability to axially adjust the spacing between the proximal and distal brace components.

FIG. 44A is a side elevation view demonstrating the temporary fitment of the orthotic brace shown in FIGS. 42A and 42B in association with a mechanical bone reduction fixture, like that shown in FIGS. 19A to 19F.

FIGS. 44B and 44C are enlarged perspective views of the brace support mechanisms that make possible the temporary fitment of the orthotic brace shown in FIGS. 42A and 42B in association with a mechanical bone reduction fixture, like that shown in FIGS. 19A to 19F.

FIG. 45 is a perspective view of the orthotic brace shown in FIGS. 42A and 42B being worn by an individual after the bone fracture has been mechanically reduced and fixed.

FIGS. 57 to 80 are views exemplifying a method for achieving mechanical force reduction of a bone fracture by the application of mechanical force reduction vectors comprising distal traction, superior traction, lateral translation, varus/valgus rotation, pronation/supination rotation, and flexion/extension, by use of a system like that shown in FIGS. 18A and 18B.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

This Specification discloses various devices, systems, and methods for reducing and/or fixing bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condylar fracture), e.g. at, in, or near the elbow, or at, in, or near the knee. The technical features of the devices systems and methods can be well exemplified and highlighted with respect to the reduction and fixation of supracondylar fractures of the elbow. For this reason, the devices, systems, and methods will be described in this context.

Still, it is to be appreciated that the devices, systems, and methods that embody features of the invention are not restricted to supracondylar applications. It is to be appreciated that the disclosed devices, systems, and methods are readily applicable for use in treating all types of bone fractures, simple or complex, of any bone type, in children or adults, anywhere in the body.

I. Anatomy of the Elbow

Figure 1:
FIGS. 1 to 3 illustrate prior art manual reduction and fixation of a bone fracture.
Figure 2:
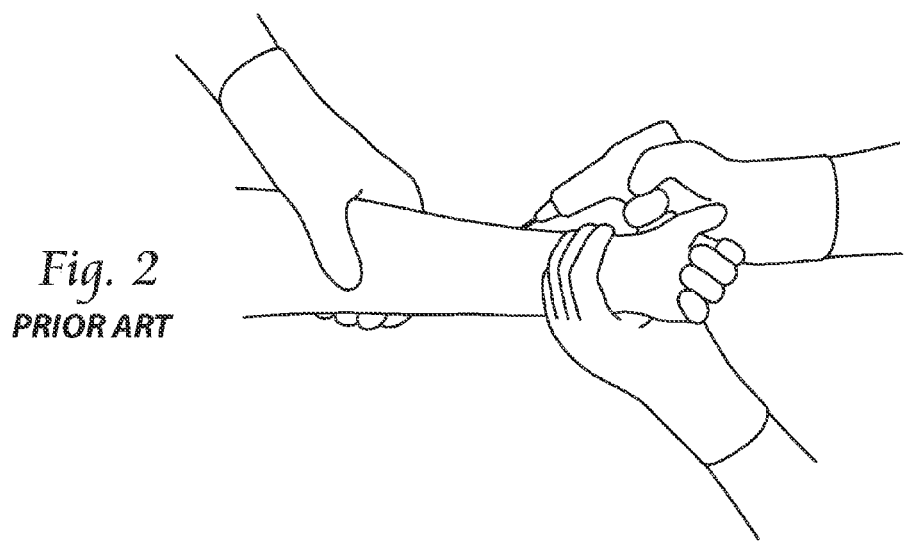
Figure 3:
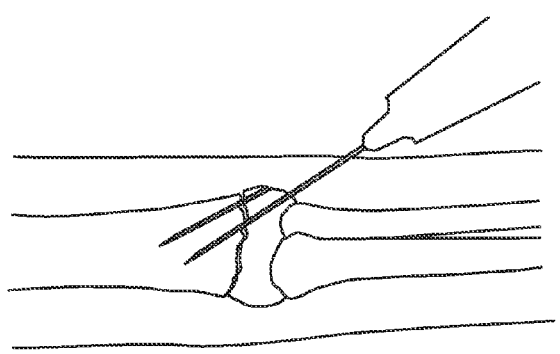
Figure 4:
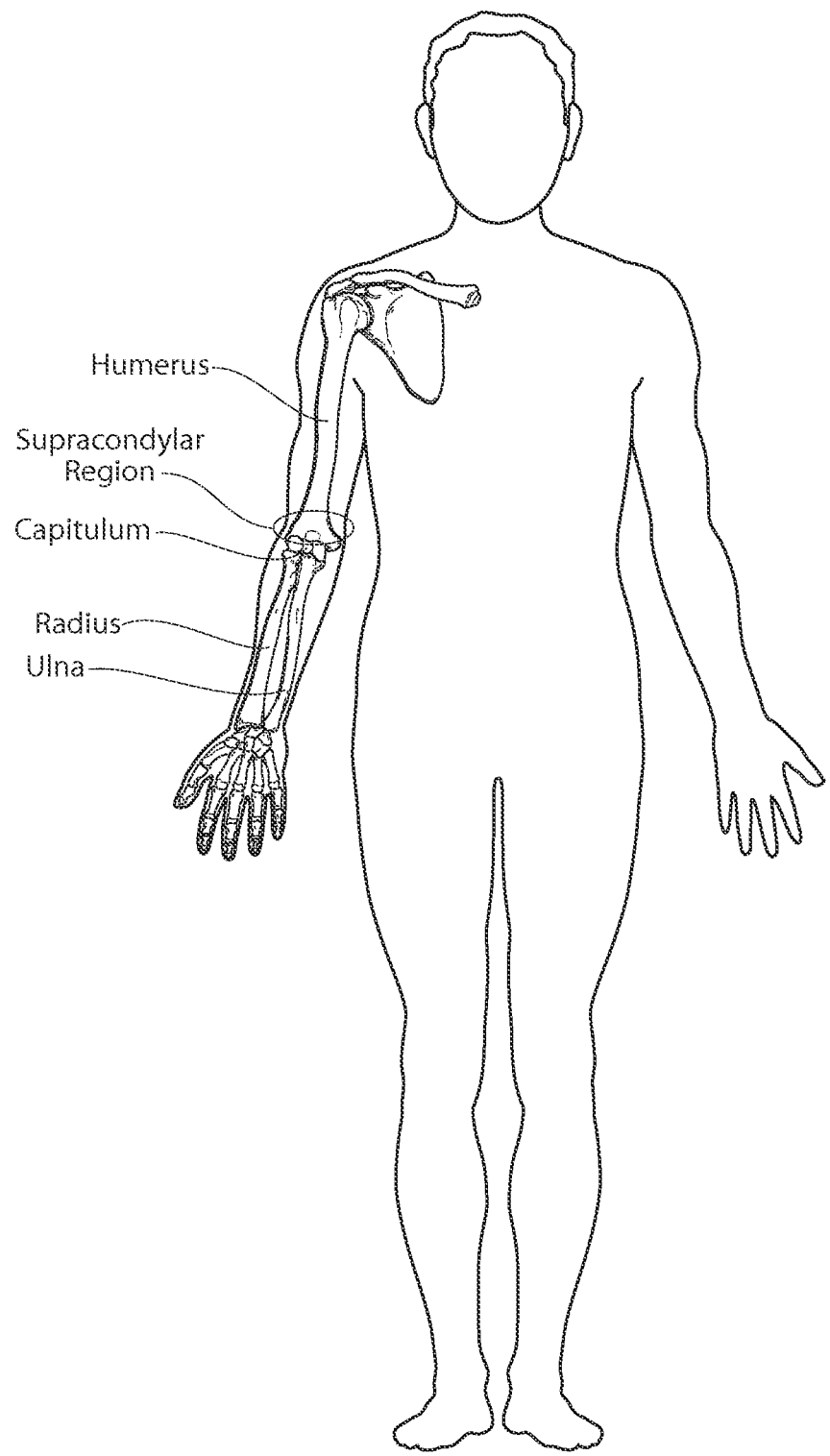
FIG. 4 is an anatomic view of a human torso, showing the supracondylar region of the right arm.

FIGS. 4, 5, and 6 exemplify the complex nature of the human elbow and its various interacting components.

As can be seen in FIGS. 4, 5, and 6, the human elbow is formed by the articulation of three bones; namely, the lower end of the humerus, the upper end of the radius, and the upper end of the ulna. Involvement of these three bones means that the human elbow consists of three joints; namely, those located (i) between the humerus and the ulna (the ulno-humeral joint); (ii) between the humerus and the radius (the radio-humeral joint); and (iii) between the ulna and the radius (the radio-ulnar joint).

Part of the ulna that articulates with the humerus includes the olecranon process and the coronoid process. The corresponding part of humerus that articulates with these processes is called the trochlea. The head of the radius articulates with the capitulum of the humerus.

II. Supracondylar Fractures

The supracondylar region (see FIGS. 4, 5, and 6) in general encompasses an area of relatively thin, weak bone located in the distal humerus. This region is bordered posteriorly by the olecranon fossa and anteriorly by the coronoid fossa.

One type of fracture to the elbow is a supracondylar fracture (see FIGS. 7 and 8). Supracondylar fractures are relatively common in children, and may occur for example, when a child falls onto an outstretched arm. With attention to the illustrated detailed views, it may be seen that the force of a fall is transmitted through the olecranon to the weak supracondylar region, causing a supracondylar fracture.

The fracture line typically propagates transversely across the distal humerus through the center of the olecranon fossa. As FIGS. 7 and 8 show, the supracondylar fracture separates the supracondylar region into a proximal fracture region and a distal fracture region. The proximal fracture region includes at least a portion of the humerus (in this context, "proximal" meaning on the side of the fracture line closer to the shoulder). The distal fracture region includes at least a portion of the radius and/or the ulna (together comprising the forearm) (in this context, "distal" meaning the side of the fracture line closer to the hand).

Depending on the severity of the fracture, the separated proximal and distal bone regions can be displaced laterally right and left (i.e., anatomically, in a medial direction toward the body or laterally away from the body). For example, FIGS. 7 and 8 show, respectively, anterior and posterior views of a supracondylar fracture of the right elbow, with the distal fracture region displaced laterally to the left (toward the body) and the proximal fracture region displaced medially to the right (away from the body).

Figure 9:
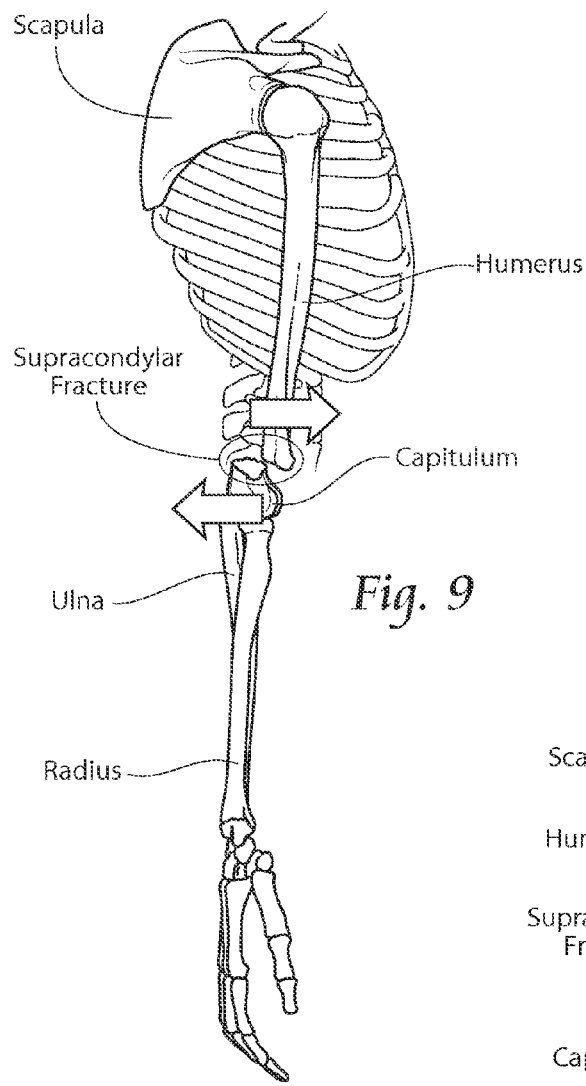
FIGS. 9 and 10 are medial views of the supracondylar fracture shown in FIGS. 7 and 8, FIG. 9 showing an anterior-posterior displacement of the proximal and distal bone regions of the fracture, and FIG. 10 showing a rotational displacement of the proximal and distal bone regions of the fracture.

Also depending on the severity of the fracture, the separated proximal and distal bone regions can be displaced forward or backwards (i.e., anatomically, to the anterior (front) or to the posterior (back), respectively). For example, FIG. 9 shows a medial view (looking toward the body) of a supracondylar fracture of the right elbow, with the distal fracture region displaced in a posterior direction (toward the back) and the proximal fracture region displaced in an anterior direction (toward the front).

Figure 10:
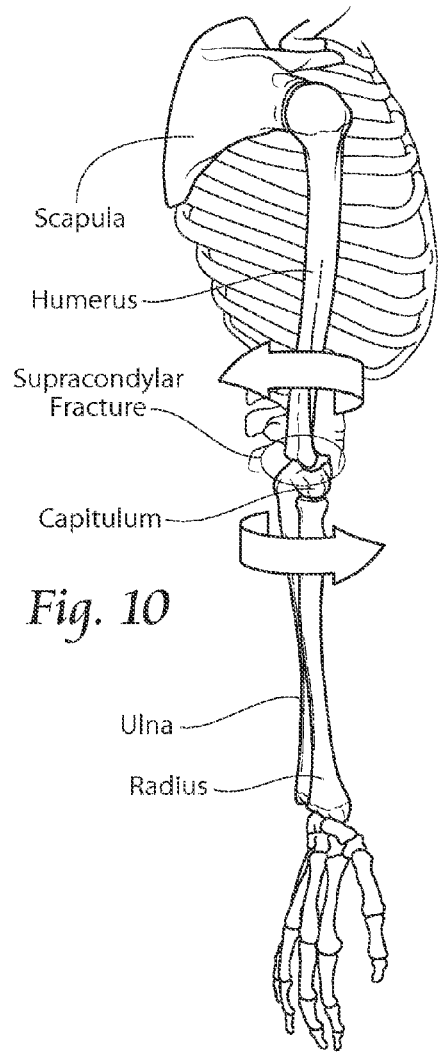

In addition to the forgoing separations and displacements of the distal fracture segment relative to the proximal fracture segment, the angular alignment of the anterior, posterior, and medial cortical surfaces of the bones in the supracondylar region may be displaced rotationally about the native longitudinal axis of the bones. For example, FIG. 10 shows a medial view (looking toward the body) of a supracondylar fracture of the right elbow, with the distal fracture region and proximal fracture region displaced rotationally out of their native axial alignment.

III. Reducing and Fixing a Bone Fracture

In conventional meaning, a fracture is "reduced" by the application of one or more forces to return the bone regions separated and displaced by the fracture back toward the native state of alignment, i.e., that which existed prior to the fracture. In conventional meaning, a fracture is "fixed" following a reduction, by stabilizing the alignment of the reduction, to prevent the reduced bone regions from moving out of reduction as healing occurs.

Depending upon the native anatomic structure of a given fracture site, and the nature of the fracture itself, reduction and fixation of a given fracture can be difficult, inexact, and time consuming. This is particularly true for fractures in the supracondylar region, as previously described, due to the nature and extent to which the native bone structures can be separated and displaced by the fracture.

The morphology and interrelationship of native anatomic structures in a given region of the body can be generally understood by medical professionals using textbooks of human skeletal anatomy along with their knowledge of the site. The physician is also able to ascertain the nature and extent of the fracture in that region of the body using, for example, plain film x-ray, fluoroscopic x-ray, or MRI or CT scanning. Based upon this information, the physician can ascertain the magnitude and direction of forces that ideally should be applied to achieve a complete reduction of the fracture. In this specification, the magnitude and direction of these forces will be called "force reduction vectors." A force reduction vector represents a reduction force operating in a defined direction and magnitude.

Figure 11A:
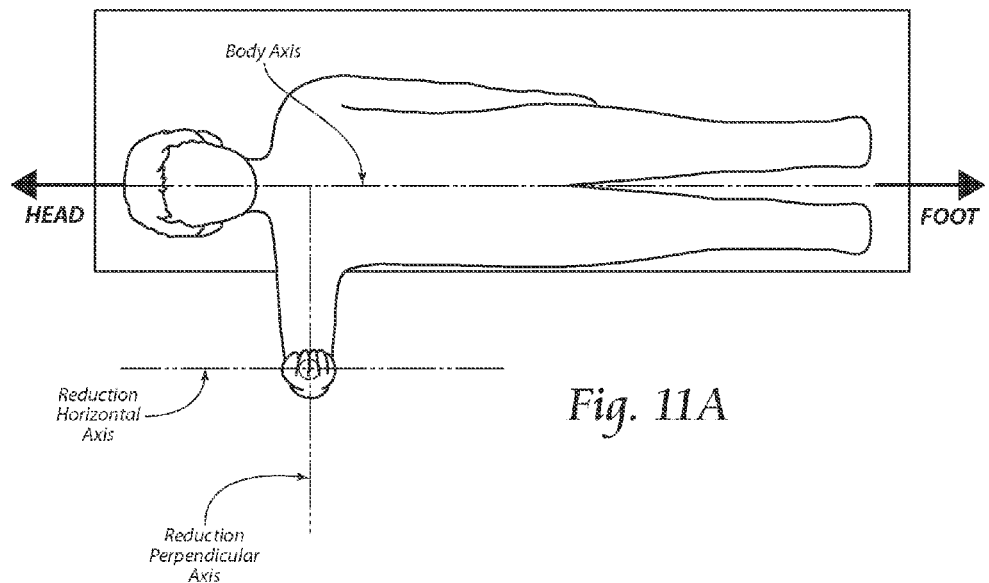
FIGS. 11A and 11B are, respectively, a top view and a right side view of an individual in a prone position, with the humerus and forearm of the individual orientated in a manner conducive for reducing a typical supracondylar fracture of the right arm, and also illustrating the principal anatomical reduction axes for the supracondylar fracture.
Figure 11B:
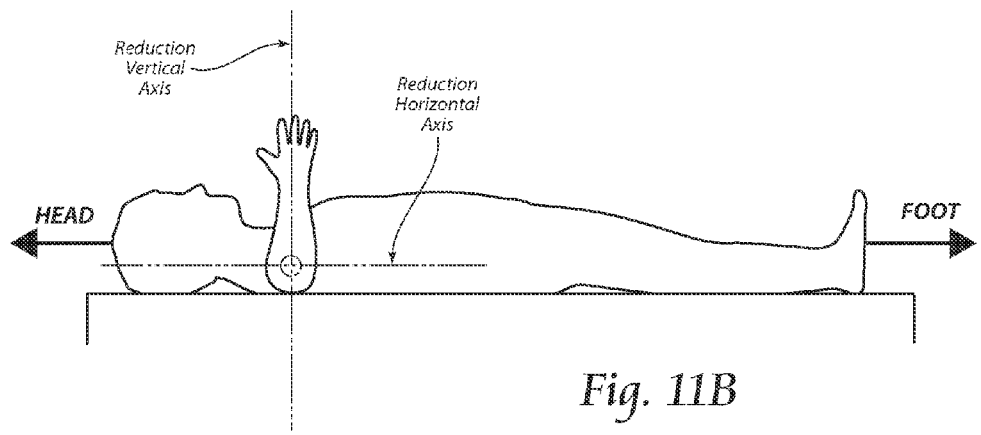

These general principles can be applied for the purpose of illustration to the humerus and elbow to treat the supracondylar region, which comprises the humerus, the forearm (comprising the ulna and radius), joined by the elbow joint. For example, as shown in FIGS. 11A and 11B, the humerus and forearm of an individual are shown orientated in a manner conducive for reducing a typical supracondylar fracture of the right arm. In this orientation, the humerus is extended at a right angle from the body axis, and the forearm is articulated upward relative to the elbow. This orientation conducive for reduction of the fracture can also be defined in terms of a fracture reduction coordinate system, which includes the principal anatomical reduction axes for a fractured supracondylar region.

The fracture reduction coordinate system comprises an anatomical reduction perpendicular axis (sometimes in shorthand called the "ARPA") (see FIG. 11A), which extends generally perpendicular to the body axis along the native longitudinal axis of the humerus to the elbow. The fracture reduction coordinate system also comprises an anatomical reduction vertical axis (sometimes in shorthand called the "ARVA") (see FIG. 11B), which extends from the elbow upward along the native longitudinal axis of the forearm, generally perpendicular to the ARPA. The fracture reduction coordinate system further includes an anatomical reduction horizontal axis (sometimes in shorthand call the "ARHA") (see FIGS. 11A and 11B), which extends through the native articulation axis of the elbow joint parallel to the body axis, which is generally perpendicular to the ARPA and ARVA.

In summary, in the fracture reduction coordinate system, the ARPA extends along the native longitudinal axis of the humerus when oriented for reduction of a supracondylar fracture. The ARVA defines the native longitudinal axis of the articulated forearm when orientated for reduction of a supracondylar fracture, the ARPA and ARVA being perpendicular to each other. The ARHA defines the native articulation axis of the elbow joint. FIG. 12A shows this orientation of the ARPA, ARVA, and ARHA, along with the presence of a supracondylar fracture, like that shown in FIGS. 7 to 10, thereby also defining the existence of the proximal bone region and the distal bone region as previously described.

With reference to the fracture reduction coordinate system shown in FIGS. 11A and 11B, the force reduction vectors required to achieve a complete reduction of the supracondylar fracture can be identified. As will now be described in greater detail, there are a total of six possible force reduction vectors for a supracondylar fracture. These are (i) distal traction (FIGS. 12A to 12D); (ii) superior traction (FIGS. 13A to 13D); (iii) lateral translation (FIGS. 14A to 14D); (iv) varus/valgus rotation (FIGS. 15A to 15D); (v) pronation/supination rotation (FIGS. 16A to 16D); and (vi) flexion/extension rotation (FIGS. 17A to 17D).

A. DISTAL TRACTION

Figure 12C:
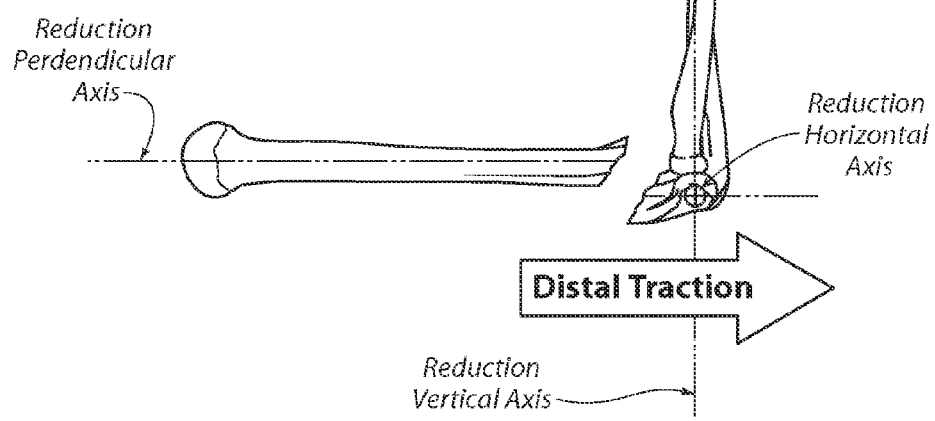
Figure 12D:
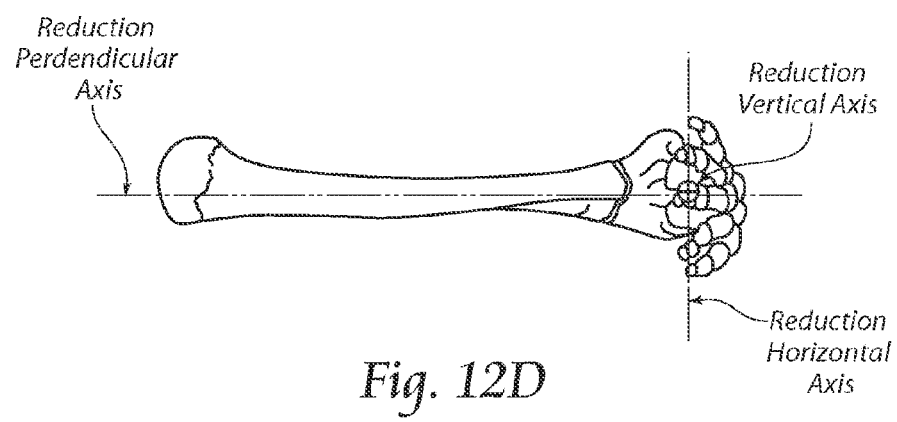

FIG. 12A illustrates a first force reduction vector called distal traction. Distal traction comprises a force vector applied along the ARPA. As shown in FIGS. 12B, 12C, and 12D, distal traction along the ARPA separates the distal bone region and the proximal fracture region so that subsequent force reduction vectors can be applied to return the proximal and distal bone regions separated and displaced by the fracture back toward the native state of alignment.

B. Superior Traction

Figure 13A:
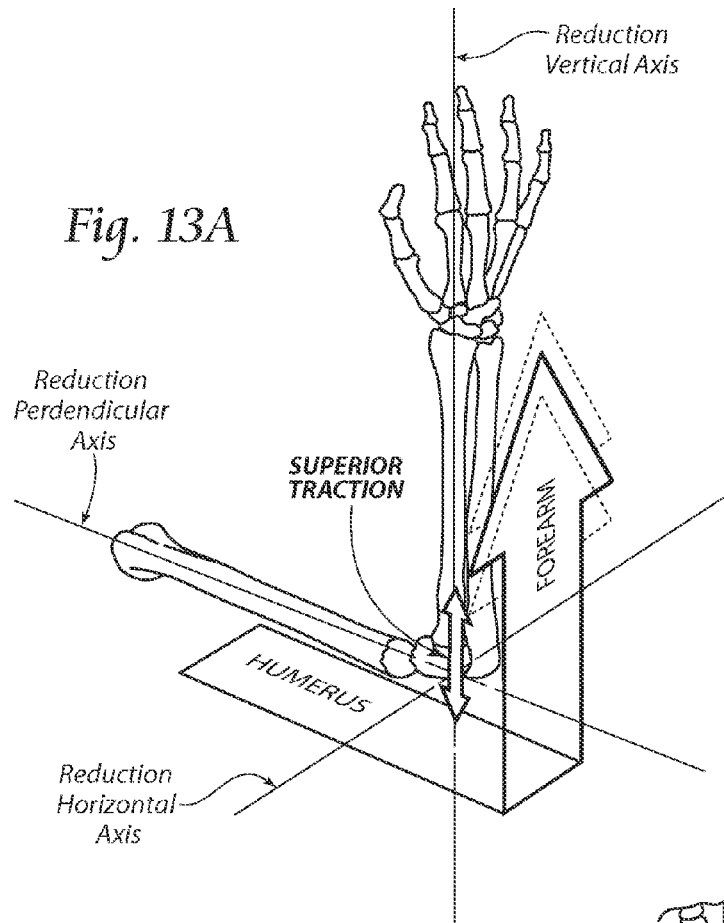
FIGS. 13A to 13D are anatomic and partially schematic views of a right human arm with a supracondylar fracture, demonstrating the application of a force reduction vector comprising superior traction.
Figure 13B:
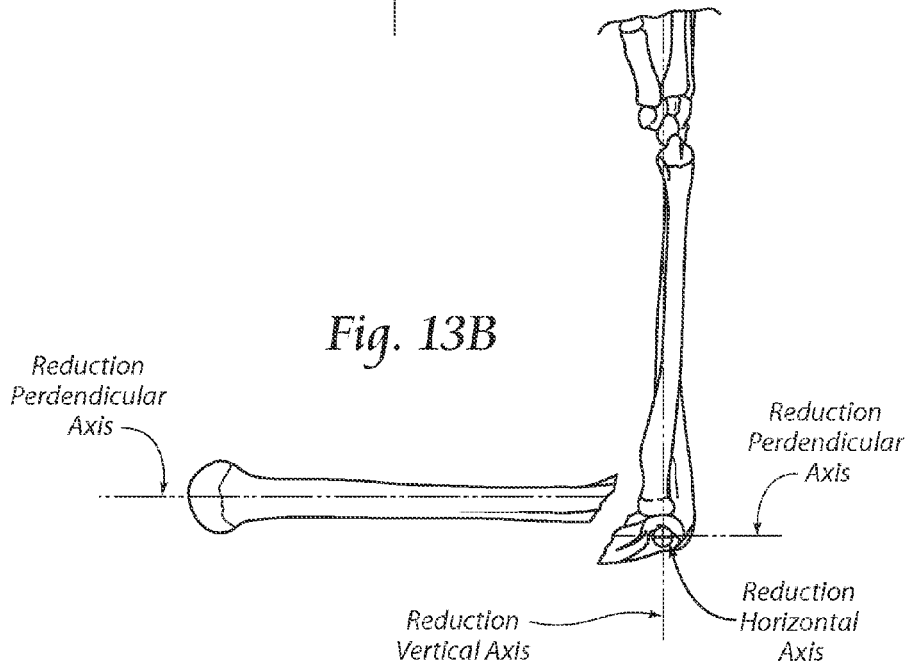
Figure 13C:
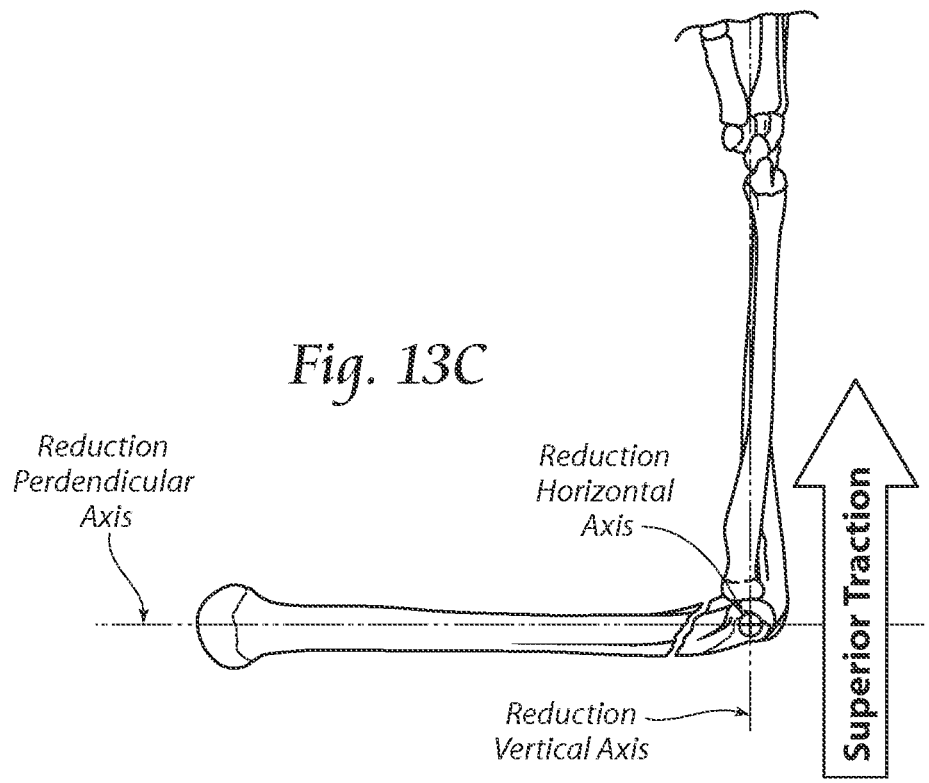
Figure 13D:
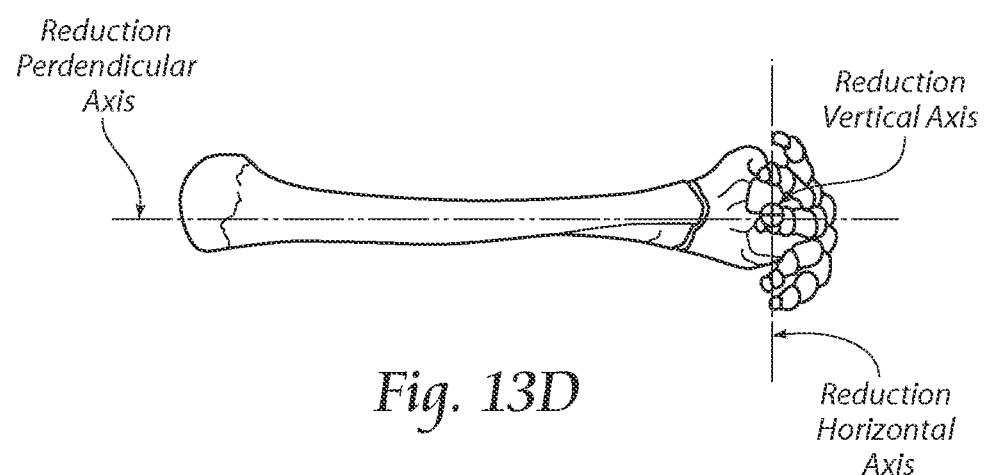

FIG. 13A illustrates a second force reduction vector called superior traction. Superior traction comprises a force vector applied along the ARVA. As shown in FIGS. 13B, 13C, and 13D, superior traction along the ARVA lifts (or, in reserve, lowers) the distal bone region as a unit relative to the proximal bone region. Superior traction returns proximal and distal bone regions that have been displaced due to the fracture forward or backwards (as shown in FIG. 9) back toward the native state of alignment.

C. Lateral Translation

Figure 14A:
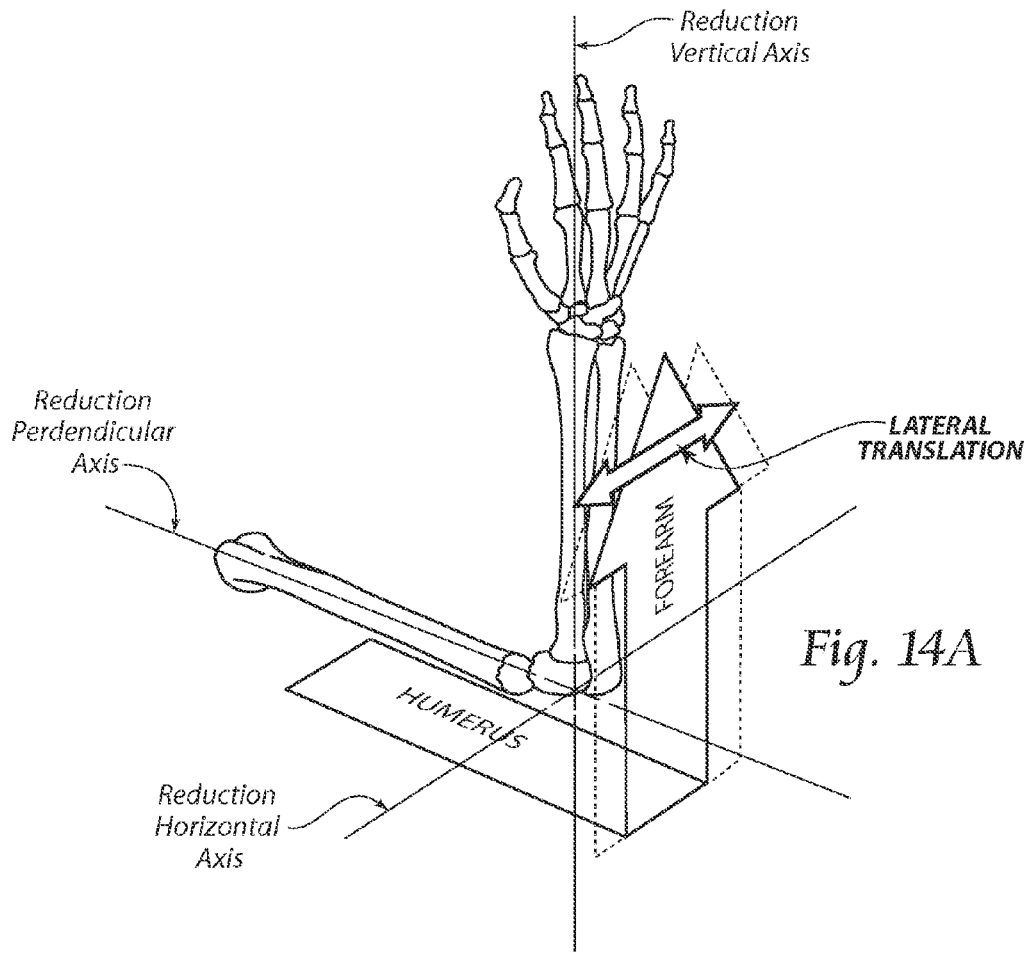
FIGS. 14A to 14D are anatomic and partially schematic views of a right human arm with a supracondylar fracture, demonstrating the application of a force reduction vector comprising lateral translation or traction.
Figure 14B:
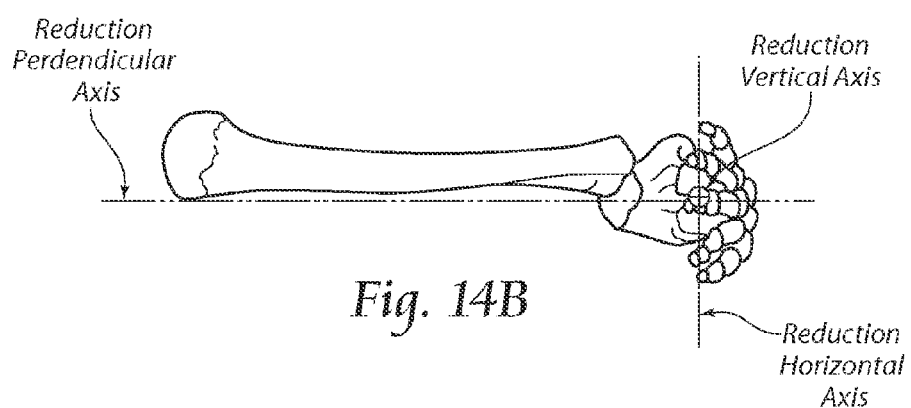
Figure 14C:
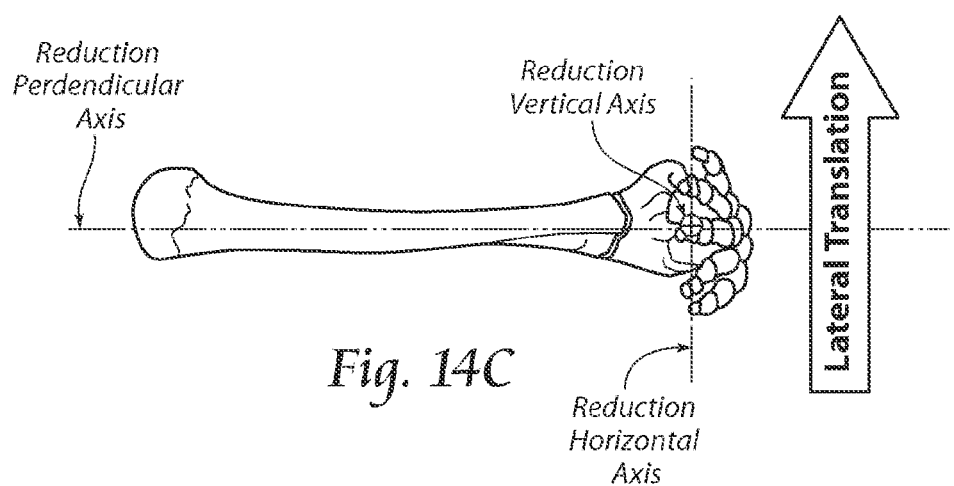
Figure 14D:
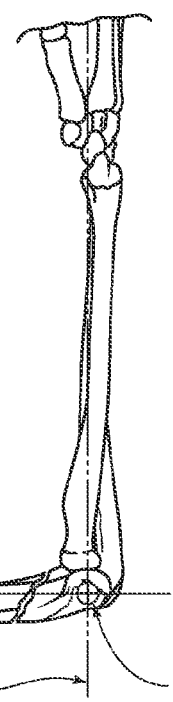

FIG. 14A illustrates a third force reduction vector called lateral translation. Lateral translation comprises a force vector applied along the ARHA. As shown in FIGS. 14B, 14C, and 14D, lateral translation along the ARHA moves the fractured end of the distal bone regions across the fractured end of the proximal bone region. Lateral translation returns proximal and distal bone regions that have been medially displaced left or right due to the fracture (as shown in FIGS. 7 and 8) back toward the native state of alignment.

D. Varus/Valgus Rotation

Figure 15A:
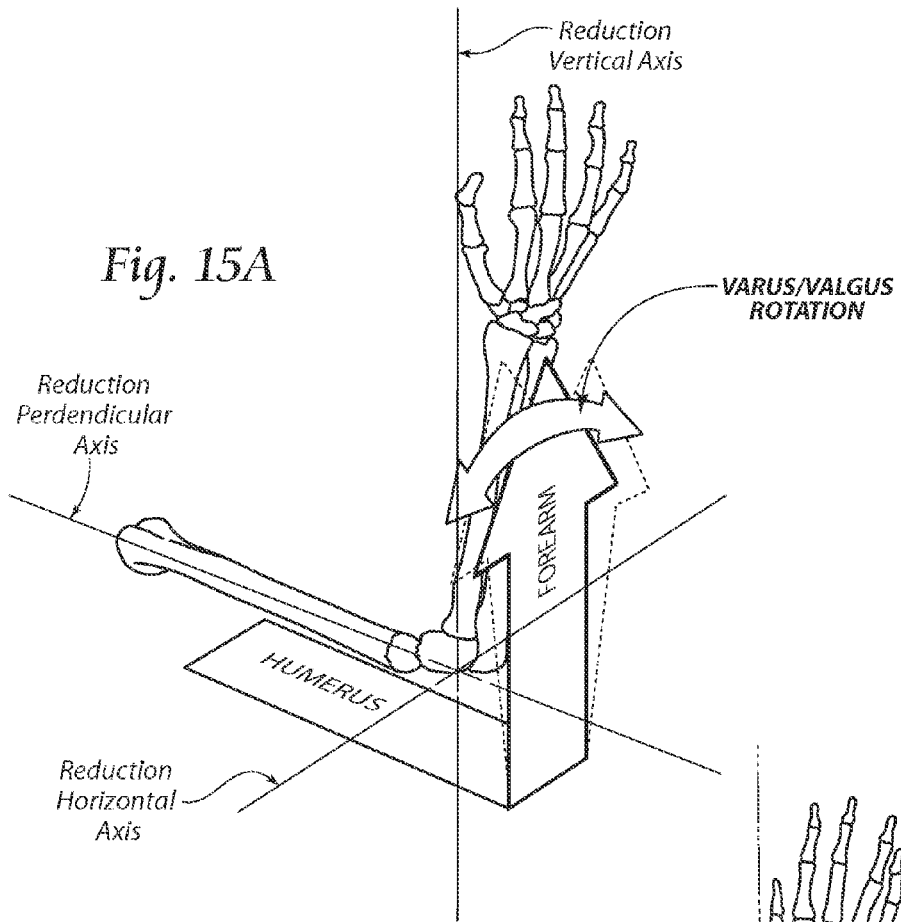
FIGS. 15A to 15D are anatomic and partially schematic views of a right human arm with a supracondylar fracture, demonstrating the application of a force reduction vector comprising varus/valgus rotation.
Figure 15B:
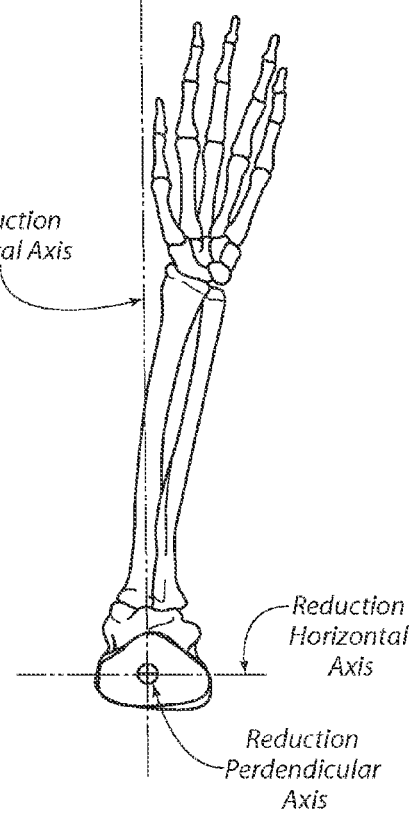
Figure 15C:
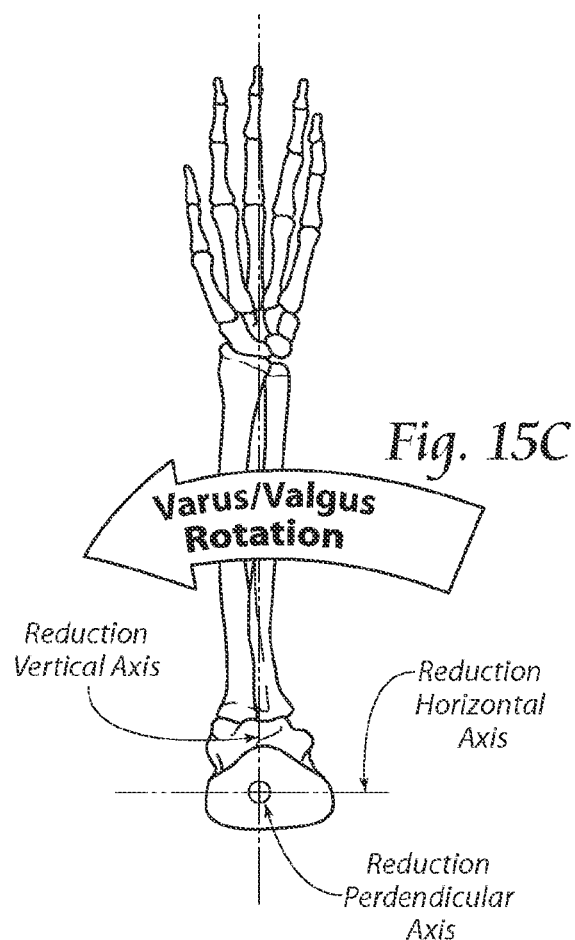
Figure 15D:
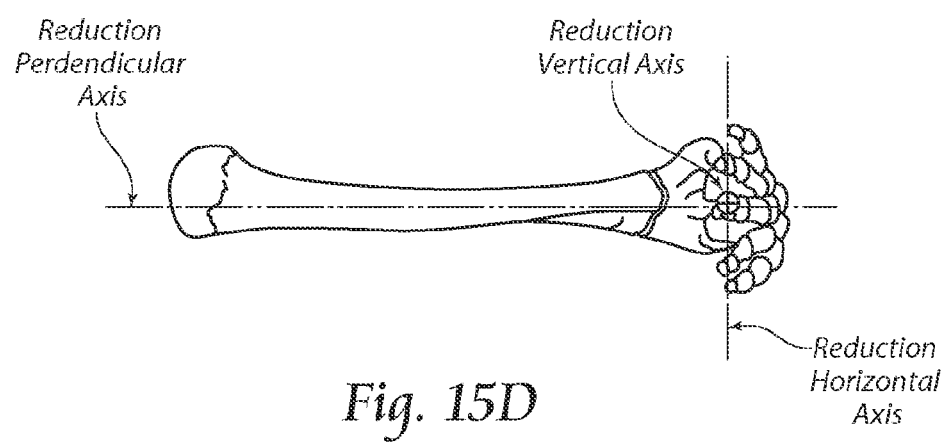

FIG. 15A illustrates a fourth force reduction vector called varus/valgus rotation. Varus/valgus rotation comprises a rotational force vector (torque) applied about the ARPA. As shown in FIGS. 15B, 15C, and 15D, varus/valgus rotation about the ARPA pivots the fractured end of the distal bone region about the longitudinal axis of the proximal bone region. Varus/valgus rotation returns proximal and distal bone regions that have been rotationally displaced due to the fracture (as shown in FIG. 10) back toward the native state of alignment. Varus/valgus rotation serves to bring back into native alignment the posterior, anterior, and medial cortical surfaces along the fracture line.

E. Pronation/Supination Rotation

Figure 16A:
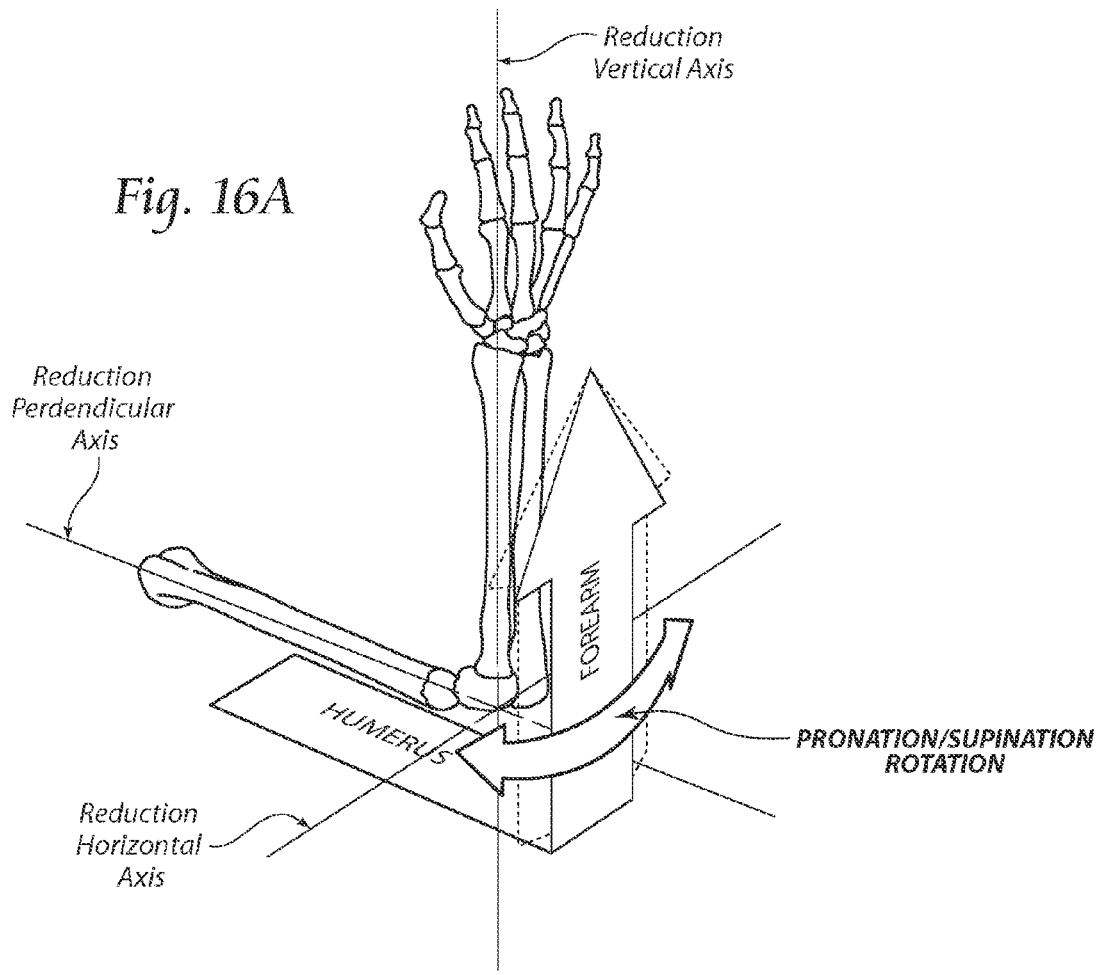
FIGS. 16A to 16D are anatomic and partially schematic views of a right human arm with a supracondylar fracture, demonstrating the application of a force reduction vector comprising pronation/supination rotation
Figure 16B:
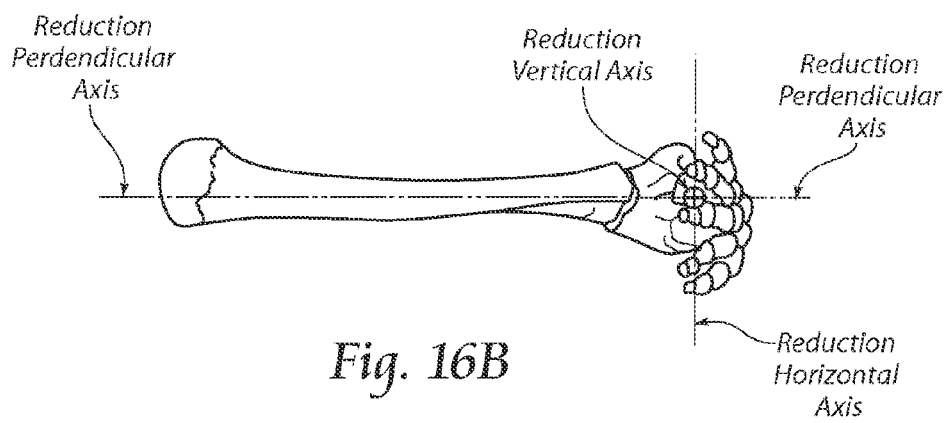
Figure 16C:
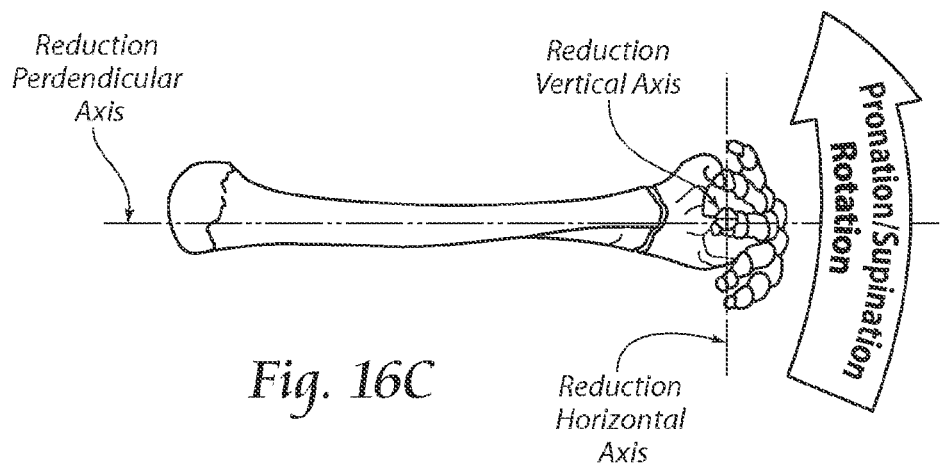
Figure 16D:
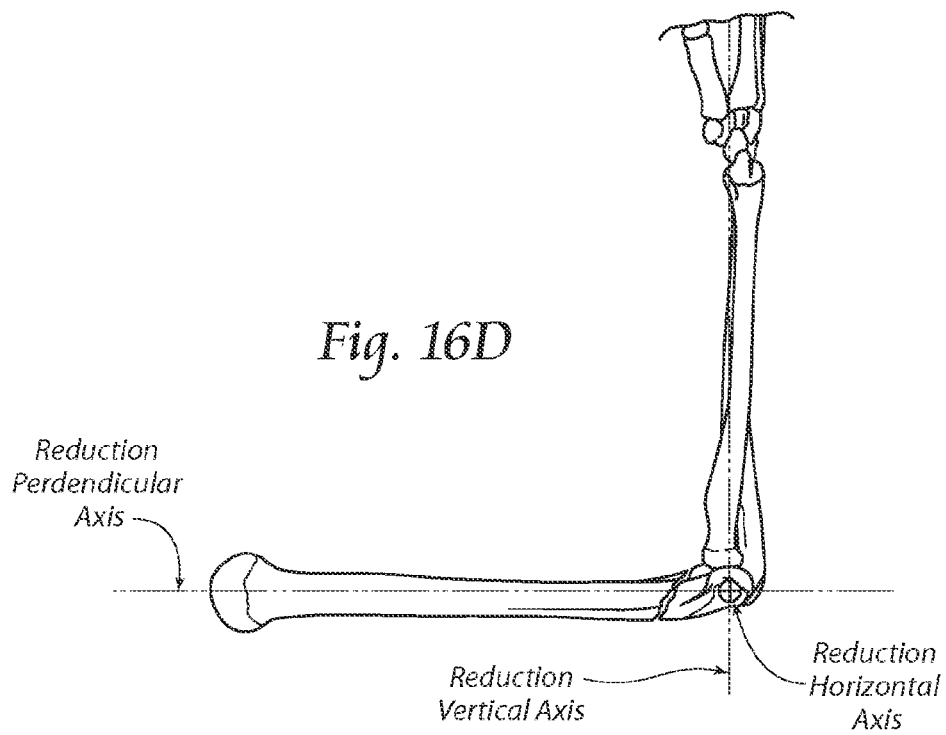

FIG. 16A illustrates a fifth force reduction vector called pronation/supination rotation. Pronation/supination rotation comprises a rotational force vector (torque) applied about the ARVA. As shown in FIGS. 16B, 16C, and 16D, pronation/supination rotation about the ARVA pivots the fractured end of the distal bone region about the longitudinal axis of distal bone. Like varus/valgus rotation, pronation/supination rotation returns proximal and distal bone regions that have been rotationally displaced due to the fracture (as shown in FIG. 10) back toward the native state of alignment. Pronation/supination rotation also serves to bring back into native alignment the posterior, anterior, and medial cortical surfaces along the fracture line.

F. Flexion/Extension Rotation

Figure 17A:
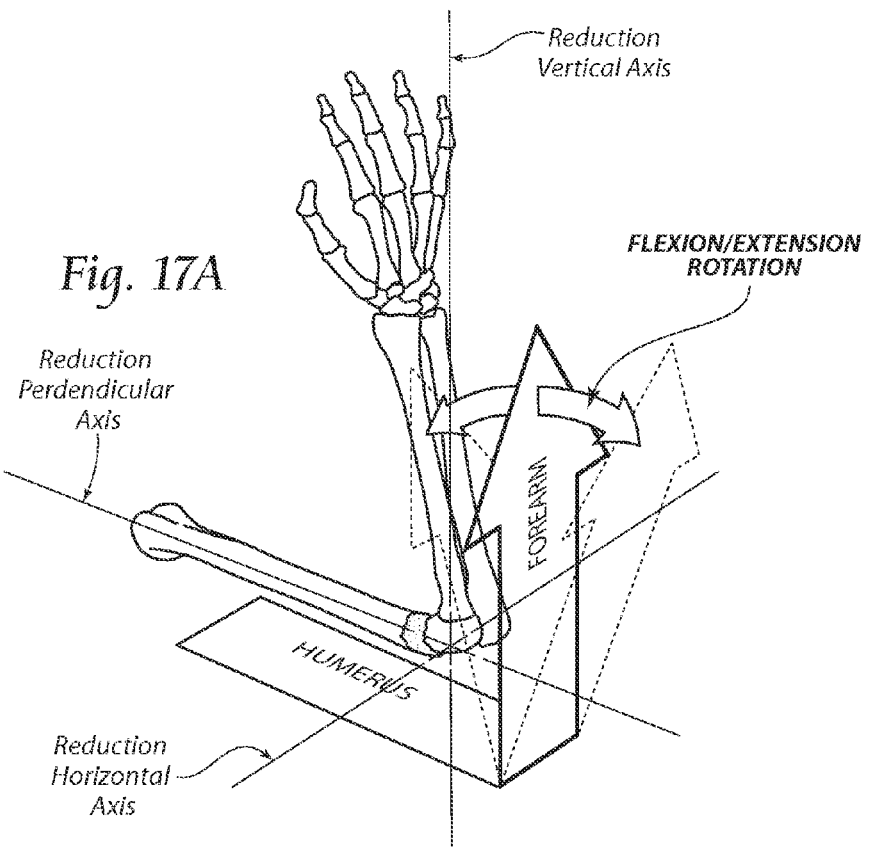
FIGS. 17A to 17D are anatomic and partially schematic views of a right human arm with a supracondylar fracture, demonstrating the application of a force reduction vector comprising flexion/extension rotation.
Figure 17B:
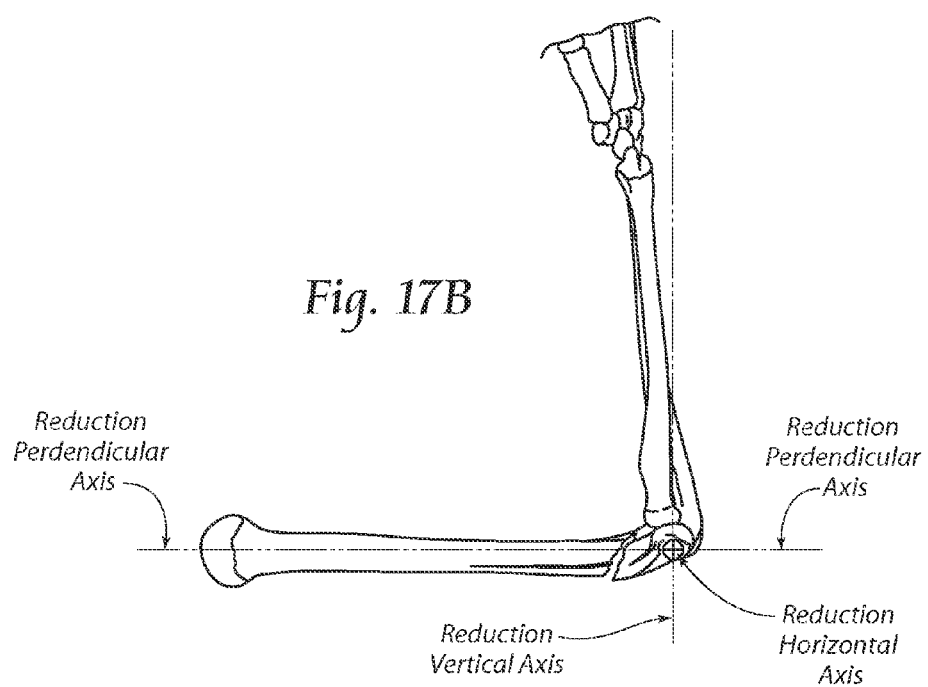
Figure 17C:
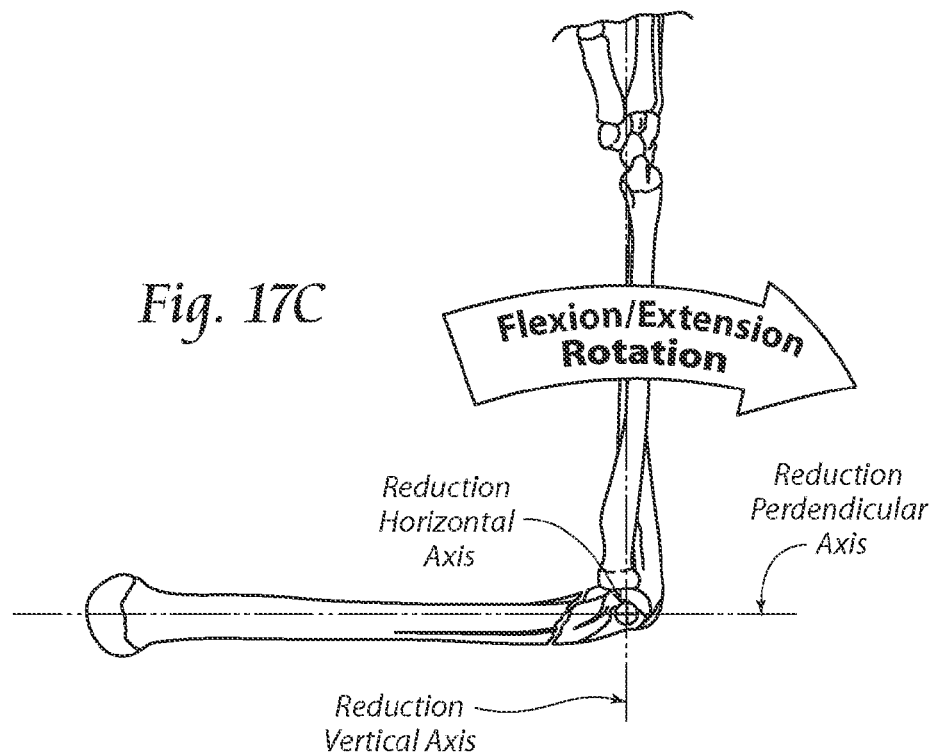
Figure 17D:
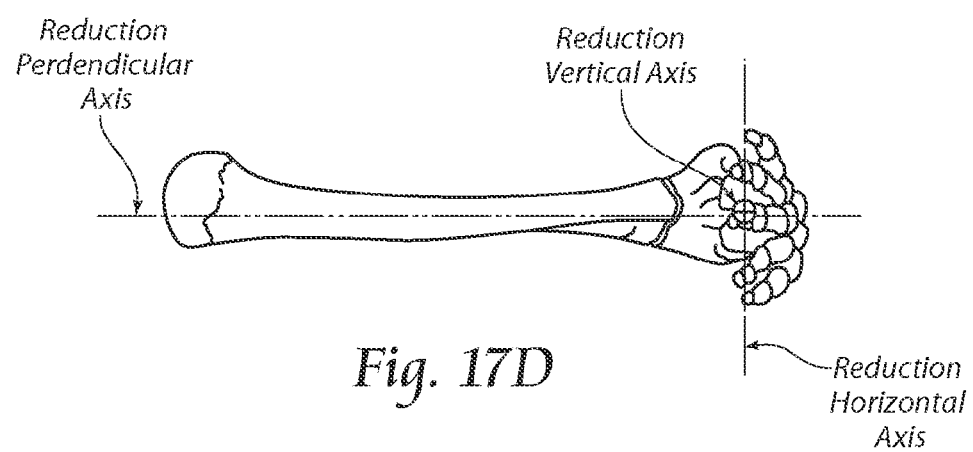

FIG. 17A illustrates a sixth force reduction vector called flexion/extension rotation. Flexion/extension rotation comprises a rotational force vector (torque) applied about the ARHA. As shown in FIGS. 17B, 17C, and 17D, flexion/extension rotation about the ARHA pivots the fractured end of the distal bone region toward the fractured end of the proximal bone region. Flexion/extension rotation returns the fractured ends of the proximal and distal bone regions that have been separated due to the fracture back toward the native state of alignment.

IV. Systems and Devices for Mechanically Reducing a Bone Fracture

A. Overview

The rationale of systematically identifying force reduction vectors, although previously described in the context of reducing supracondylar fractures, provides the context for achieving, in a systematic way, a reduction of any bone fracture. Still, in this context, systemic problems can still exist.

Force reduction vectors, once identified, are inherently different in terms of their therapeutic objectives and results. For example, in the context of reduction of a supracondylar fracture, the force reduction vectors independently operate along or about three different axes; namely the ARPA, ARVA, and ARHA. Achieving a desired therapeutic result along or about one axis can be lost or compromised when an attempt is made to achieve a therapeutic result along or about another axis. For example, the therapeutic objectives of distal traction can be lost or compromised when a different force reduction vector is next applied along another axis. The loss of distal traction can, in turn, obstruct the application of another force vector. Further, the application of superior traction can alter the therapeutic results of a previously achieved lateral traction, or vice versa, or the application of varus/valgus rotation can alter the results of a previously achieved pronation/supination rotation or flexion/extension rotation, and so on. Force reduction vectors for whatever facture operate in a dynamic interdependent physical environment. This dynamic interdependent physical environment thwarts achievement of a complete reduction by the application of independent force reduction vectors along or about different axes.

B. Mechanical Force Reduction

Figure 18A:
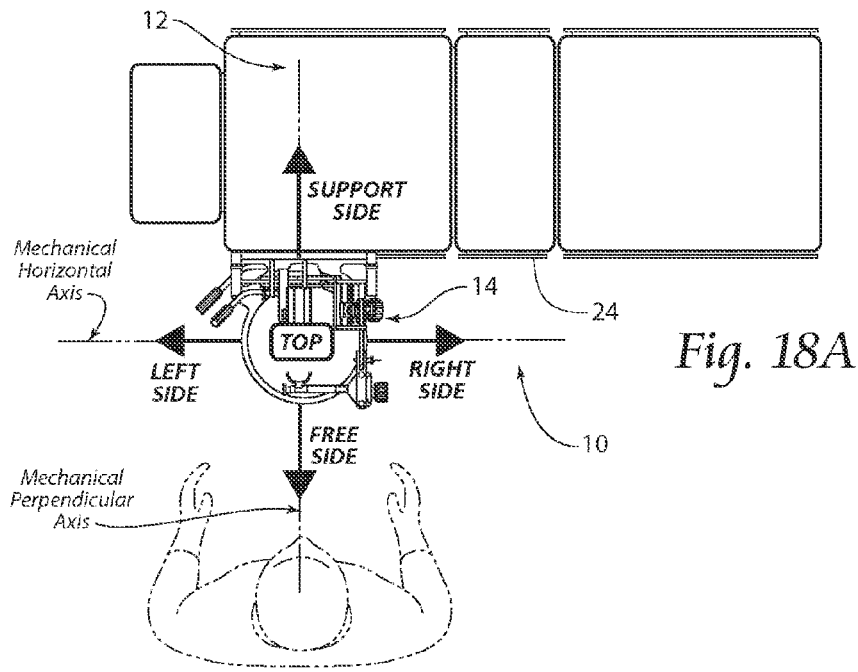
FIGS. 18A and 18B show, respectively, top and side views of an exemplary system sized and configured for achieving a complete, composite reduction of a bone fracture, comprising a patient support platform and a mechanical bone reduction fixture that can be mounted for use on the patient support platform, and also illustrating the principal mechanical axes of the mechanical bone reduction fixture.
Figure 18B:
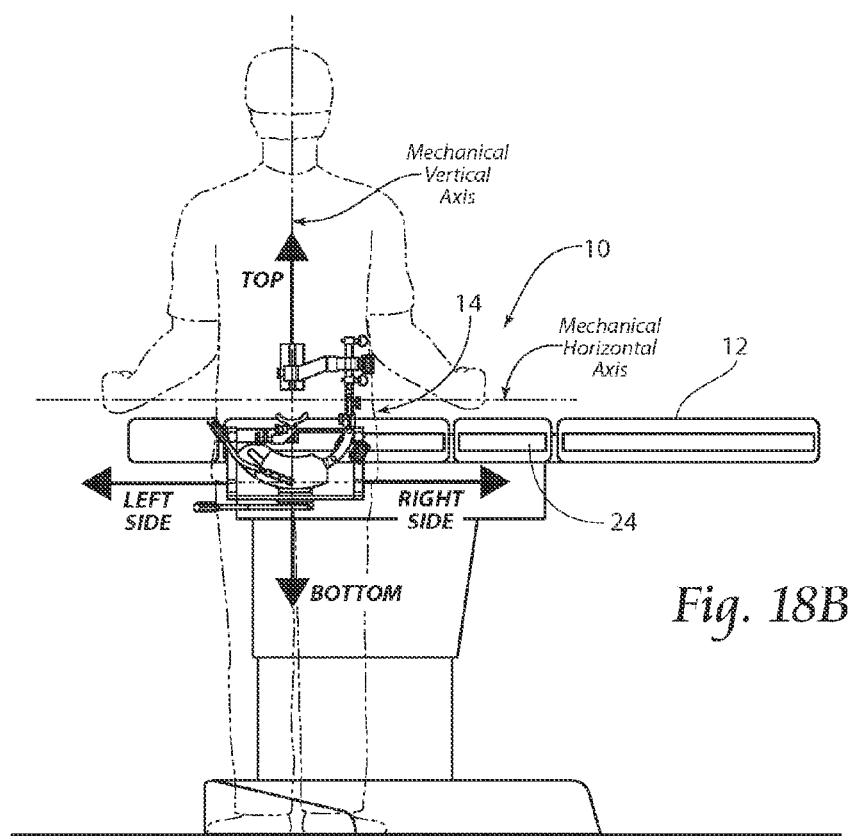

FIGS. 18A and 18B show, respectively, top and side views of an exemplary system 10 sized and configured for achieving a complete, composite reduction of a bone fracture. The system 10 overcomes the problems presented by the dynamic interdependent physical environment of reducing a fracture—which has before now thwarted achievement of a complete composite reduction—by independently applying and maintaining a plurality of disparate mechanical force reduction vectors concurrently along disparate axes. The technical features and benefits of the system 10 will be described in the context of reducing a supracondylar fracture, but the technical features that will be described are applicable to reducing bone fractures, simple or complex, of all bone types, in children or adults.

The system 10 achieves a mechanical force reduction of the fracture. The term "mechanical force reduction" means a reduction of a bone fracture by the application of mechanical force, which will also sometimes be called a "mechanical force vector" or a "force reduction vector."

As used herein, the terms "mechanical" and "mechanism" broadly connote the presence of one or more tools or instruments that generate and transform the direction or magnitude of a force to reduce a bone fracture by applying kinetic energy and/or electrical energy and/or pneumatic energy and/or hydraulic energy and/or chemical energy, and/or thermal energy, and/or elastic energy, and combinations thereof. In this respect, the terms "mechanical" and "mechanism" as used herein apply not only to the use of "machines" in the traditional sense (e.g., with components such as axles, bearings, gears, linkages, springs, wheels, pulleys, motors, engines, compressors, pumps, pistons, and the like, interacting alone or in combination to generate and apply kinetic force), but also to any tool or instrument that generates/applies force to reduce a bone fracture that includes, e.g., electrical and/or electro-mechanical components, and/or pneumatic components, and/or hydraulic components, and/or electronic components, and/or mechatronic components, and/or nanotechnology components, and can also incorporate, e.g., robotics, automation, and/or computer control.

Mechanical force reduction achieves, for the first time, a complete, composite reduction of a bone fracture by independently applying and maintaining force reduction vectors in a mechanical way concurrently along different axes.

As an overview, in a representative implementation, the system 10 applies at least two external, mechanically generated forces to a bone fracture. One of the external mechanically generated forces comprises a first mechanical force vector that moves a bone fracture into alignment in a first anatomic orientation. The system 10 further mechanically maintains a desired alignment in the first anatomic orientation. The system 10 applies another external, mechanically generated force, independent of the first mechanical force vector, comprising a second mechanical force vector. The second mechanical force vector moves the bone fracture into alignment in a second anatomic orientation different than the first anatomic orientation. Because the system 10 mechanically maintains a desired alignment in the first anatomic orientation while applying the second mechanical force vector, alignment in a second anatomic orientation is achieved without altering the desired alignment in the first desired orientation.

In this way, the system 10 mechanically applies a given mechanical force vector to achieve alignment in a first anatomic orientation, and while mechanically maintaining the alignment achieved in the first anatomic orientation, proceeds to apply another mechanical force vector to achieve alignment in another anatomic orientation, and then mechanically maintains that alignment, and so on, until all desired alignments in all identified anatomic orientations are made, to form a composite reduction. At that time, the system 10 can provide systematic mechanical bone fixing of the composite reduction, as will be described in greater detail later.

In the context of treating a supracondylar fracture, and as will be described in greater detail, the system 10 is capable of applying mechanical force reduction in all six possible anatomic reduction orientations. As previously described, the six mechanical force reductions for a supracondylar fracture comprise reduction by (i) distal traction (previously exemplified in FIGS. 12A to 12D); (ii) superior traction (previously exemplified in FIGS. 13A to 13D); (iii) lateral translation (previously exemplified in FIGS. 14A to 14D); (iv) varus/valgus rotation (previously exemplified in FIGS. 15A to 15D); (v) pronation/supination rotation (previously exemplified in FIGS. 16A to 16D); and (vi) flexion/extension rotation (previously exemplified in FIGS. 17A to 17D). In this way, the system 10 makes possible, for the first time, a mechanically-achieved complete composite reduction of a supracondylar fracture.

The system 10 can be variously constructed to achieve this objective. Exemplary structural embodiments will now be described.

C. An Exemplary System for Reduction of a Supracondylar Fracture

1. Overview

As shown in FIGS. 18A and 18B, the system 10 comprises a patient support platform 12 and a mechanical bone fracture reduction fixture 14 mounted on the patient support platform 12. As will be described in greater detail later, the patient platform 12 is sized and configured to support an individual having a bone fracture. The mechanical bone fracture reduction fixture 14 includes at least one fracture reduction mechanism 16 that is sized and configured to apply to the bone fracture at least one mechanical force vector that moves the bone fracture into at least one desired anatomic orientation. The fracture reduction mechanism 16 includes a mechanism that is sized and configured to mechanically maintain the desired anatomic orientation, In a representative embodiment, the mechanical bone fracture reduction fixture 14 is sized and configured to be conveyed separate from the patient platform 12. In this arrangement, the mechanical bone fracture reduction fixture 14 includes a mount 20 to join the fixture 14 to the patient platform 12 to support the bone fracture for reduction by the mechanical bone fracture reduction fixture 14 and, after a reduction of the fracture is achieved, to separate the fixture 14 from the patient platform 12.

As will also be described in greater detail later, the system 10 can further include a mechanical guidance mechanism 18 that is sized and configured to guide placement of one or more bone fixing devices to fix the reduction of the fracture.

In a representative embodiment, the mechanical bone fracture reduction fixture 14 and the mechanical guidance mechanism 18 share a common frame 22. In this arrangement, the mount 20 joins the common frame 22 to the patient platform 12 for fracture reduction by the mechanical bone fracture reduction fixture 14 and fixing by the mechanical guidance mechanism 18 and, after fracture reduction and fixing are achieved, to separate the common frame 22 from the patient platform 12.

More particularly, the patient platform 12 is sized and configured to place an individual having a supracondylar fracture in a comfortable, stable position in proximity to the fracture reduction fixture 14. The patient platform 12 can be, e.g., a chair; or a generally use horizontal resting surface, bed, or table suited for supporting the body of an individual in a supine or prone position conducive for reducing a fracture; or a general use, but more specialized surgical table or gurney, like those found in an emergency room or an operating room; or an even-more customized fracture reduction table or fixture customized for the needs orthopedic surgery (capable, e.g., of controlling the position, articulation, and manipulation of a patient's lower and/or upper extremities). The fracture reduction fixture 14 supplements and customizes the technical features of the patient platform 12 to the reduction of the particular fracture of interest. In all arrangements, the fracture reduction fixture 14 comprises a temporary appendage to the patient platform 12, providing it with the functionality customized for reducing the particular bone fracture, in this case, a supracondylar fracture. It should be appreciated however, that, if desired, the patient platform 12 and the fracture reduction fixture 14 can be provided as integrated unit.

Figure 19A:
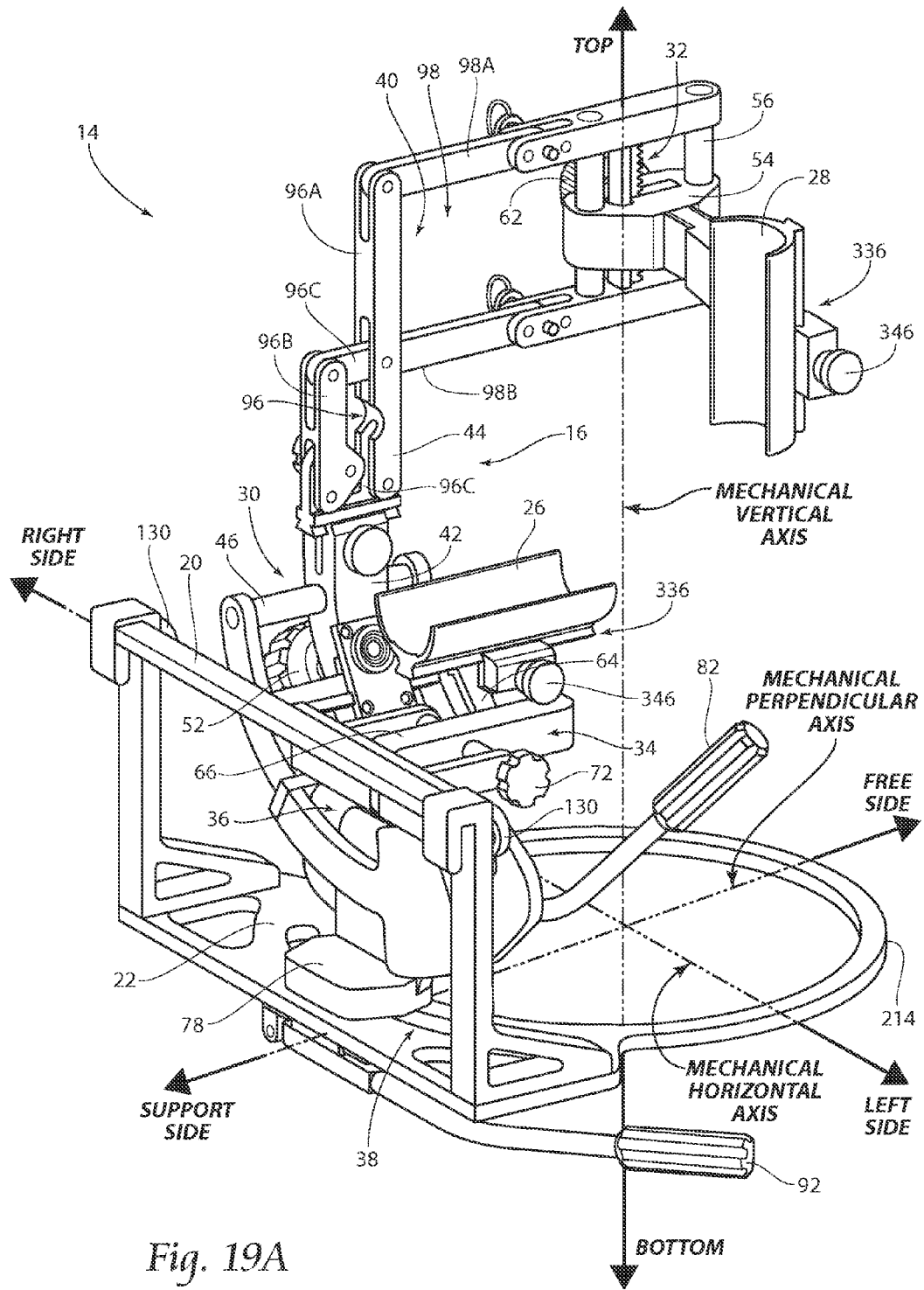
FIGS. 19A to 19F are views of the mechanical bone reduction fixture shown in FIGS. 18A and 18B, showing in greater detail the mechanical components for applying force vectors for reducing a supracondylar fracture comprising distal traction, superior traction, lateral translation, varus/valgus rotation, pronation/suprination rotation, and flexion/extension, and also identifying directional points of reference and the principal mechanical axes of movement.

In the exemplary embodiment shown in FIGS. 18A and 18B the system 10 contemplates a modular-type construction. The fracture reduction fixture 14 comprises a frame 22 having a support mount 20, which is sized and configured for temporary mounting to a patient platform 12 selected to carry the individual being treated. The support mount 20 allows for the fracture reduction fixture 14 to be attached as a preassembled unit at the instance of use to the selected patient platform 12 prior to use (see FIGS. 18A and 18B), to thereby form the system 10 at the instance of use. The support mount 20 also allows the fracture reduction fixture 14 to be removed as a preassembled assembly from the patient platform 12 after use for storage and subsequent reuse on a different selected patient platform 12. Further details of the exemplary mount 20 are shown in FIG. 19A.

Figure 19B:
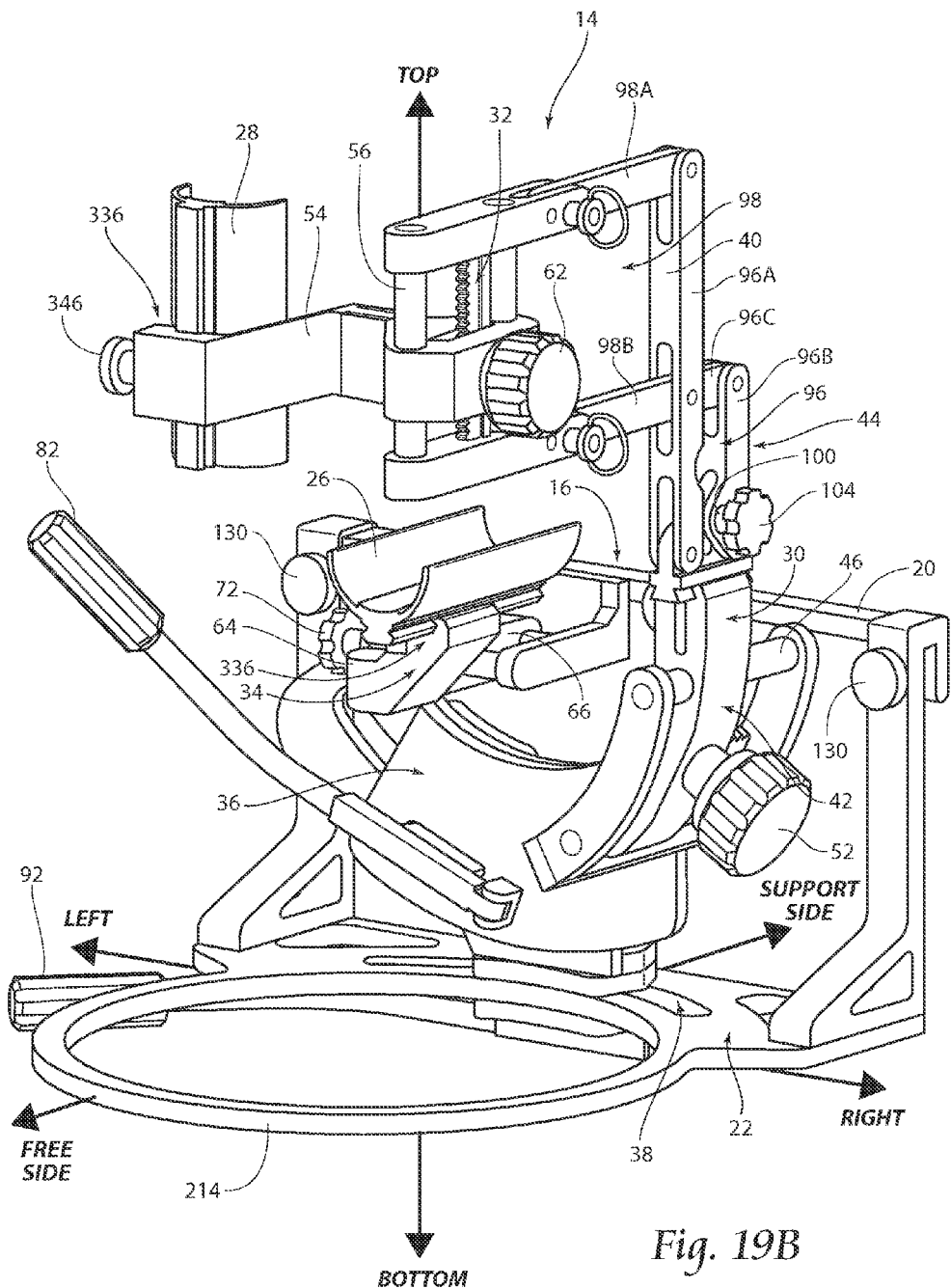
Figure 19C:
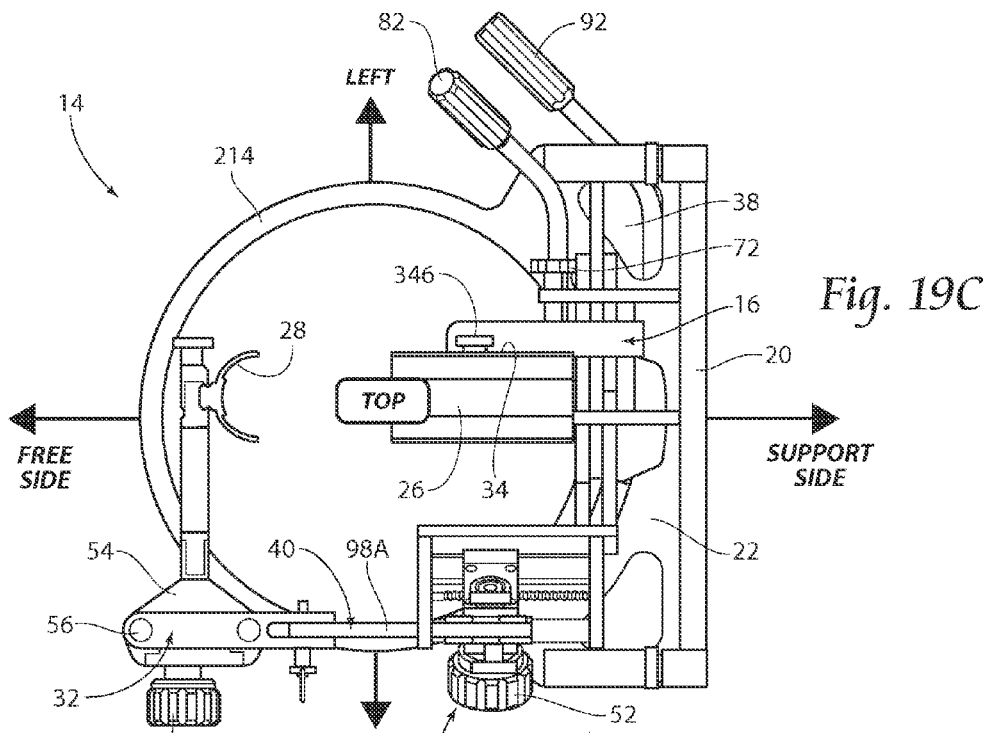
Figure 19D:
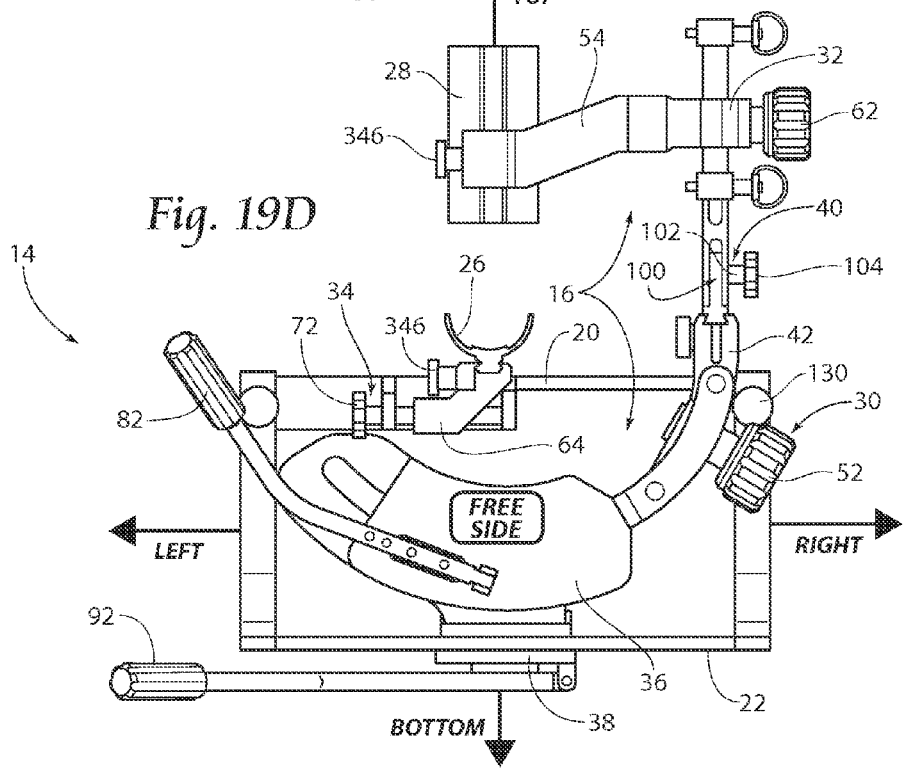
Figure 19E:
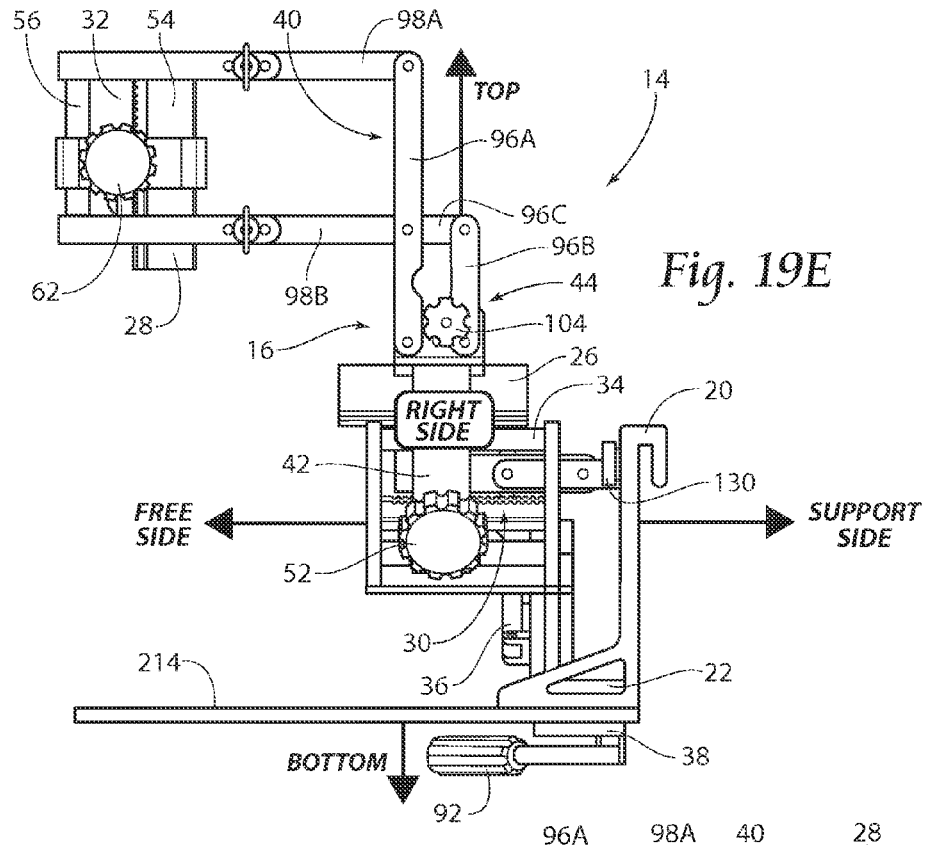
Figure 19F:
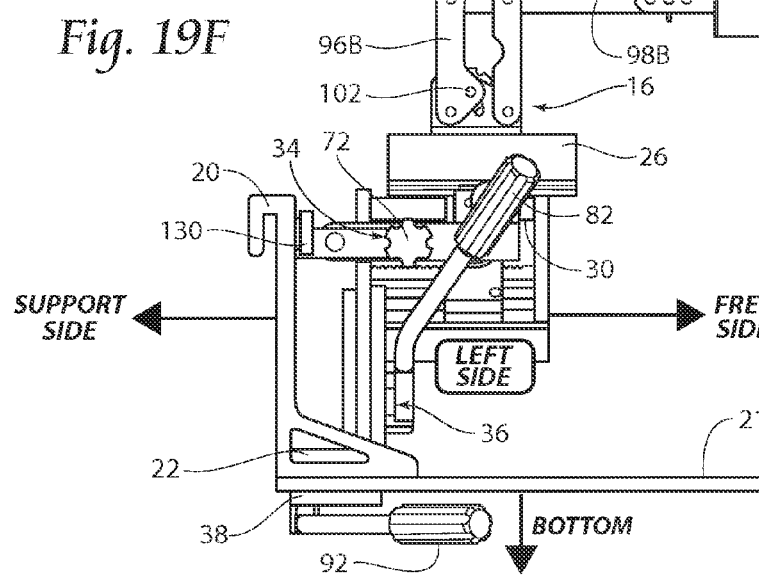
Figure 19G:
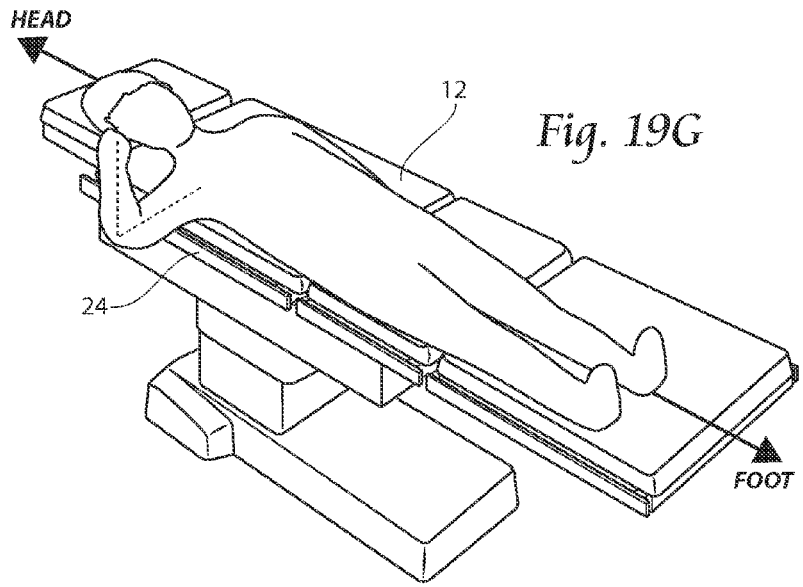
FIG. 19G is a perspective view of an individual having a supracondylar fracture of a right arm laying in a prone position on a patient support platform, with the humerus and forearm of the individual orientated in a manner conducive for reducing a typical supracondylar fracture of the right arm, Figures.
Figure 19H:
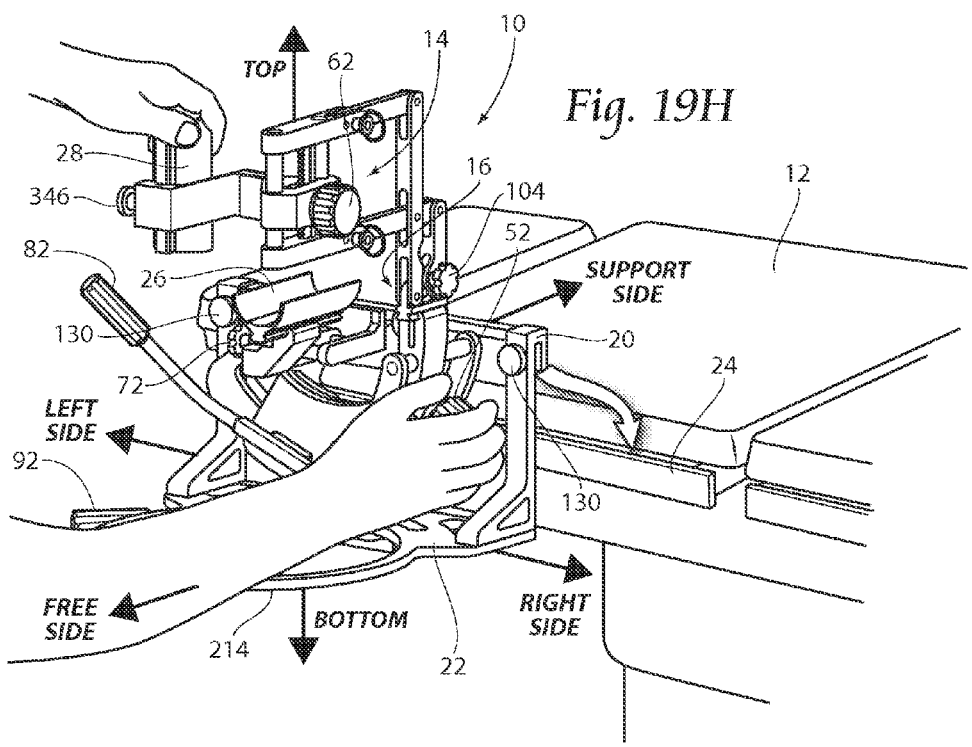
FIG. 19H is a perspective view showing the mounting of a mechanical bone reduction fixture as shown in FIGS. 19A to 19F to a side rail of a patient support platform as shown in FIG. 19G for use.

The provision of a support mount 20 on the fracture reduction fixture 14 makes the fracture reduction fixture portable for placement on a side rail 24 that is typically part of a conventional operating table or gurney (also see FIGS. 19G and 19H). Other forms of support mounts can be sized and configured to accommodate the particular structure of other patient platforms, such as customized fracture reduction tables or fixtures customized for the needs orthopedic surgery.

Attached to the patient platform 12, the fracture reduction fixture 14 in the exemplary embodiment is supported at waist level for use in a cantilevered orientation from a side of the patient platform 12, which is an orientation that is conducive for the reduction of a supracondylar fracture. Reduction of another type of fracture may call for a different orientation for the respective fracture reduction fixture 14, i.e., one that is not cantilevered from and/or not supported on a side of the patient platform 12, but is instead oriented above or below the patient platform 12, and/or supported at or from another region of the patient platform 12, because that particular orientation is conducive to the reduction of that particular fracture.

FIGS. 18A and 18B have been annotated to establish baseline directional points of reference for the exemplary embodiment of the fracture reduction fixture 14 and the system 10 from a structural standpoint, which will be referred to in subsequent more detailed descriptions and drawings. FIGS. 18A and 18B establish, for the fracture reduction fixture 14 and system 10, the baseline direction points of reference called a Support Side, a Free Side, Left, Right, Top and Bottom, as based upon the structural orientation of fracture reduction fixture 14 as shown in FIGS. 18A and 18B. That is, the Support Side, Free Side, Left Side, Right Side, Top, and Bottom directional points of reference are relative to the view of a surgeon or caregiver when facing the patient platform 12 and holding the fracture reduction fixture 14 to place the support mount 20 on a support rail of the patient support platform 12. From this point of view, the surgeon faces the side rail 24 of the patient support platform 12, holding the fracture reduction fixture 14 on the side opposite to the Support Side (i.e., the Free Side) to present the Support Side to the side rail 24 for placement on the side rail 24. From this perspective (viewed by the surgeon from the Free Side), the fracture reduction fixture 14 has a Left Side (to the surgeon's left), a Right Side (to the surgeon's right), a Top (toward the surgeon's head) and a Bottom (toward the surgeon's feet).

Figure 18C:
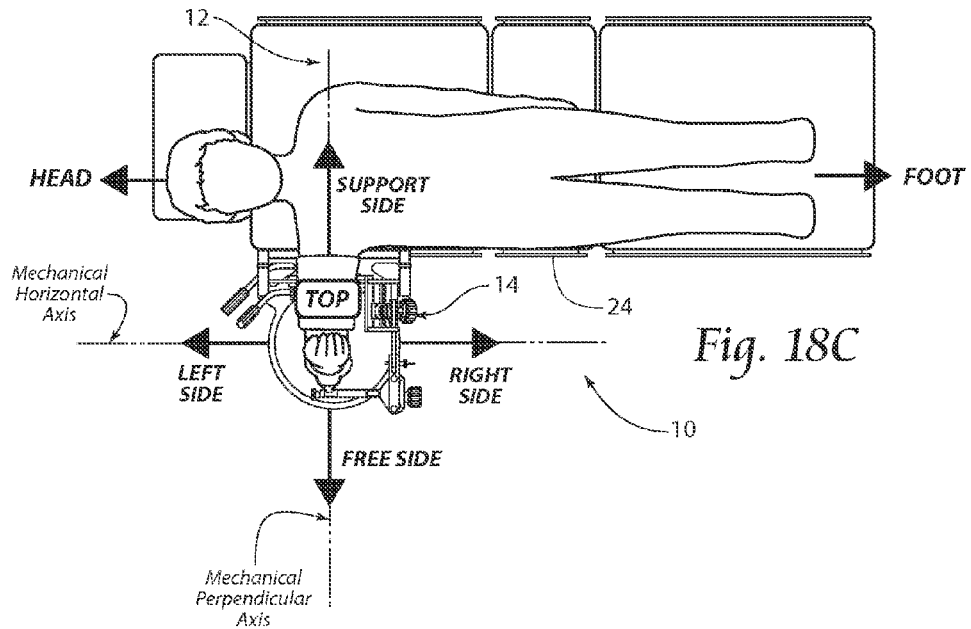
FIG. 18C is a top view of the system shown in FIGS. 18A and 18B in use, with an individual having a supracondylar fracture of a right arm laying in a prone position on the patient support platform, and the mechanical bone reduction fixture supporting the humerus and forearm of the individual in a manner conducive for reducing the supracondylar fracture of the right arm.
Figure 18D:
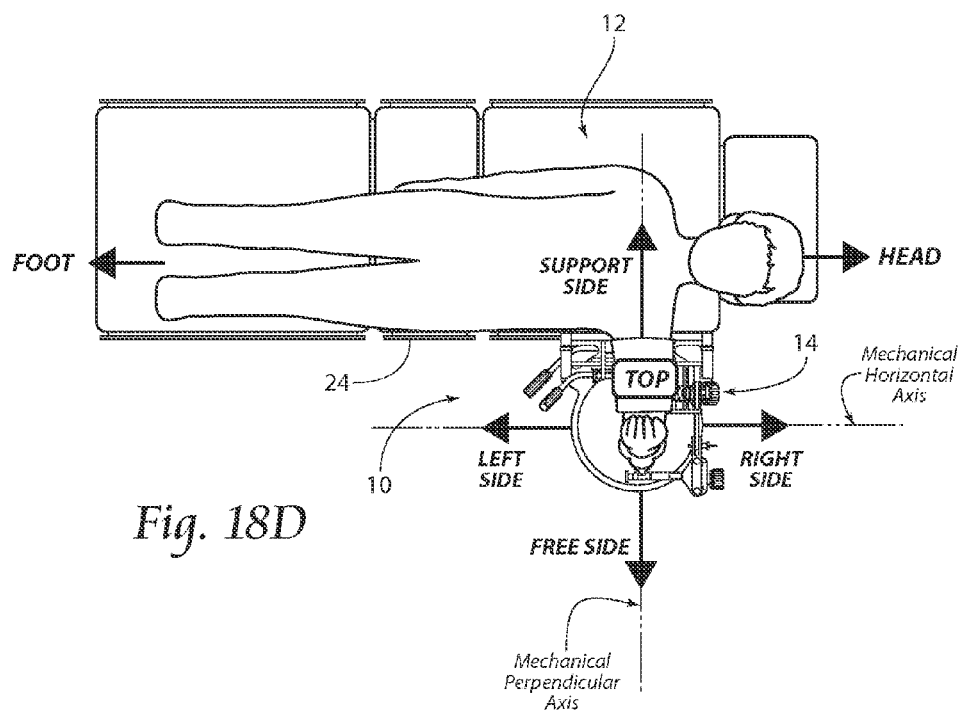
FIG. 18D is a top view of the system shown in FIGS. 18A and 18B in use, with an individual having a supracondylar fracture of a left arm laying in a prone position on the patient support platform, and the mechanical bone reduction fixture supporting the humerus and forearm of the individual in a manner conducive for reducing the supracondylar fracture of the left arm.

The orientation of the Left and Right Sides of the fracture reduction fixture 14 relative to head and feet of the patient when in use will vary depending upon whether the supracondylar fracture is in the patient's right arm (FIG. 18C) or in the patient's left arm (FIG. 18D). For a right arm fracture, the Left Side of the fracture reduction fixture 14 faces the patient's head (FIG. 18C). For a left arm fracture, the Right Side of the fracture reduction fixture 14 faces the patient's head (FIG. 18D).

The mechanical axes of the fracture reduction fixture 14 relative to these directional points of reference are also identified in FIGS. 18A to 18D. The mechanical axes comprise a Mechanical Horizontal Axis, which extends between the Right and Left Sides; a Mechanical Vertical Axis, which extends between the Top and Bottom; and a Mechanical Perpendicular Axis, which extends between the Support Side and the Free Side.

These directional points of reference established for FIGS. 18A to 18D are also carried into the companion FIGS. 19A to 19H, which show the details of an exemplary fracture reduction fixture 14 prior to placement on the patient platform 12. The mechanical axes established in FIGS. 18A to 18D are further identified in FIG. 19A.

FIG. 19A is a perspective view of an exemplary fracture reduction fixture 14 (prior to placement on the patient platform 12) from the Support Side. FIG. 19B is a perspective view of the fracture reduction fixture 14 from the Right Ride. FIG. 19C shows the fracture reduction fixture 14 in a top plane view from the Top of FIGS. 19A and 19B; FIG. 19D shows the fracture reduction fixture 14 in an elevation view from the Free Side. FIG. 19E is an elevation view of the fracture reduction fixture 14 from the Right Side, and FIG. 19F is an elevation view of the fracture reduction fixture 14 from the Left Side.

In the embodiment shown in FIGS. 19G and 19H, the support mount 20 comprises a flange or bracket projecting from the Support Side, which is sized and configured to be hung on a conventional side rail 24 or edge of an operating table or gurney (which then comprises the patient support platform 12). For example, FIG. 19H shows the flange or bracket 20 being situated on the side rail 24, with the side rail 24 providing general support for the fracture reduction fixture 14 cantilevered from the patient platform 12 at generally the waist level of the surgeon or caregiver (see FIG. 18B). The support mount 20 also desirably includes one or more suitable securing elements 130 (see FIG. 19B), e.g. a friction screw device, for providing a rigid point of attachment of the fracture reduction fixture 14 to the patient platform 12, thereby forming the system 10 ready for use.

The support mount 20 can be fabricated from durable machined or molded metal parts, which can be shaped in conventional fashion, e.g., by molding, fasteners, and/or welding. Likewise the design of the securing element can be of any arrangement that will allow the fracture reduction fixture 14 to be securely and rigidly attached to a patient platform 12, or other selected surface that a patient will lie upon, as demonstrated in FIG. 19G.

The design and positioning of the support mount 20 allows for horizontal stabilization of the patient on the patient platform 12, in an orientation that is conducive for reduction and (desirably) fixing of the patient's fracture. Particularly, the orientation of the fracture reduction fixture 14 relative to the patient platform 12 orients the patient's humerus and radius/ulna in the fracture reduction fixture 14 for reduction and (desirably) fixing of the fracture.

2. Orienting the Fracture for Reduction

In the illustrated embodiment (see, e.g., FIGS. 18C, 18D, and 19G), the patient platform 12 is sized and configured to comfortably support the upper torso of the individual to be treated, at rest in a supine (on the back) position. The patient platform 12 can be sized and configured to support an adult's upper torso and/or a child's upper torso. In the illustrated embodiment, the patient platform 12 is intended to support at least the torso of a child. Stabilization for the individual's torso can be provided, as desired, by straps across the supine torso fitted to the patient platform 12.

In the illustrated embodiment (see FIGS. 18C and 18D), the fracture reduction fixture 14 is sized and configured to comfortably support the appendage of the individual having the fracture that is to be reduced while lying on the patient platform 12. In the illustrated embodiment, the appendage is an arm having a supracondylar fracture. The fracture reduction fixture 14 orients the fracture along the desired fracture reduction coordinate system, which, for a supracondylar fracture, is shown in FIGS. 11A and 11B.

The fracture reduction fixture 14 is sized and configured to support an adult's arm or a child's arm, depending upon who the individual to be treated is. In the illustrated embodiment, the fracture reduction fixture 14 is sized and configured for treatment of a child. This is also shown later, e.g., in FIG. 48.

In this arrangement (see FIG. 19A), the fracture reduction fixture 14 includes a humeral support carriage 26, which extends parallel to the Mechanical Perpendicular Axis between the Support Side and the Frees Side of the fracture reduction fixture 14. In use, the humeral support carriage 26 is secured to the humerus, to hold the humerus in a laterally extended position from the shoulder, as FIGS. 18C and 18D show.

The fracture reduction fixture 14 also includes (see FIG. 19A) a radius/ulna support carriage 28, which extends parallel to the Mechanical Vertical Axis between the Top and the Bottom of the fracture reduction fixture 14. In use, the radius/ulna support carriage 28 is secured to the radius/ulna, to hold the radius/ulna while flexed at the elbow to point the hand in a superior direction facing the shoulder, as FIGS. 18C and 18D show.

3. Mechanical Force Reduction Assemblies

The fracture reduction mechanism 16 carried by the fracture reduction fixture 14 comprises a plurality of mechanical force reduction assemblies 30, 32, 34, 36, 38, 40. The mechanical force reduction assemblies 30, 32, 34, 36, 38, and 40 are carried by the frame 22 of the fracture reduction fixture 14 in a prescribed mechanical association with the humeral support carriage 26 and the radius/ulna support carriage 28.

Each of the mechanical force reduction assemblies 30, 32, 34, 36, 38, and 40 is sized and configured to independently mechanically manipulate the arm resting in the humeral support carriage 26 and the radius/ulna support carriage 28, guided by conventional radiation imaging techniques. Each mechanical force reduction assembly 30, 32, 34, 36, 38, and 40 functions independently of the other mechanical force reduction assemblies, to independently apply and maintain one of the prescribed mechanical reduction forces to the fracture. Concurrently, the mechanical force reduction assemblies 30, 32, 34, 36, 38, and 40 mechanically apply and maintain a plurality of independent mechanical reduction forces, to thereby mechanically reduce the fracture in the desired reduction planes.

Because the proximal and distal fracture regions held by the fracture reduction fixture 14 are mechanically manipulated with the aid of conventional radiation imaging techniques, the mechanical force reduction assemblies 30, 32, 34, 36, 38, and 40 and companion components of the fixture 14 are desirably made from metallic and/or non-metallic materials that do not block x-ray visualization. In this way, mechanical reduction can be performed using the fixture 14 without interfering with the radiologic visualization of the fracture site as reduction occurs. For example, Delrin® Plastic (DuPont) can be used, since it is possible to image through it.

In the context of reducing a supracondylar fracture, there are six mechanical force reduction assemblies 30, 32, 34, 36, 38, and 40. The six mechanical force reduction assemblies correspond to six mechanical force reductions identified for a supracondylar fracture. In this context, the mechanical force reduction assemblies carried by the fracture reduction fixture 14 comprise (i) a distal traction mechanical force reduction assembly 30; (ii) a superior traction mechanical force reduction assembly 32; (iii) a lateral translation mechanical force reduction assembly 34; (iv) a varus/valgus rotation mechanical force reduction assembly 36; (v) a pronation/supination rotation mechanical force reduction assembly 38; and (vi) a flexion/extension rotation mechanical force reduction assembly 40. Concurrently, the six mechanical force reduction assemblies 30, 32, 34, 36, 38, and 40 carried by the fracture reduction fixture 14 make possible a mechanically-achieved complete composite reduction of a supracondylar fracture.

Further details of each mechanical force reduction assembly 30, 32, 34, 36, 38, and 40 will now be described, with reference to the exemplary embodiment shown in FIGS. 19A to 19F.

i. Distal Traction Mechanical Force Reduction Assembly

The distal traction mechanical force reduction assembly 30 mechanically applies and maintains distal traction to the fracture. As before described, and as earlier shown in FIGS. 12A to 12D, distal traction comprises a force vector applied along the Anatomical Reduction Perpendicular Axis of the fracture reduction coordinate system of the supracondylar region. Distal traction along the Anatomical Reduction Perpendicular Axis separates the distal bone region and the proximal fracture region so that subsequent force reduction vectors can be applied to return the proximal and distal bone regions separated and displaced by the fracture back toward the native state of alignment.

a. Mechanically Achieving Distal Traction

In the exemplary embodiment (initially, referring to FIG. 19A) the distal traction mechanical force reduction assembly 30 comprises a horizontal traction carriage 42. The horizontal traction carriage 42 is structurally coupled to the radius/ulna support carriage 28 by a linkage system 44, the components of which will be more fully described in greater detail later. The horizontal traction carriage 42 and the linkage system 44 that mechanically couples it to the radius/ulna support carriage 28, shown in FIG. 19A, are further shaded for identification in FIG. 20A, which (like its companion FIGS. 20B and 20C) also incorporates the directional points of reference and the principal mechanical axis of movement for distal traction established in FIG. 19A.

Figure 20A:
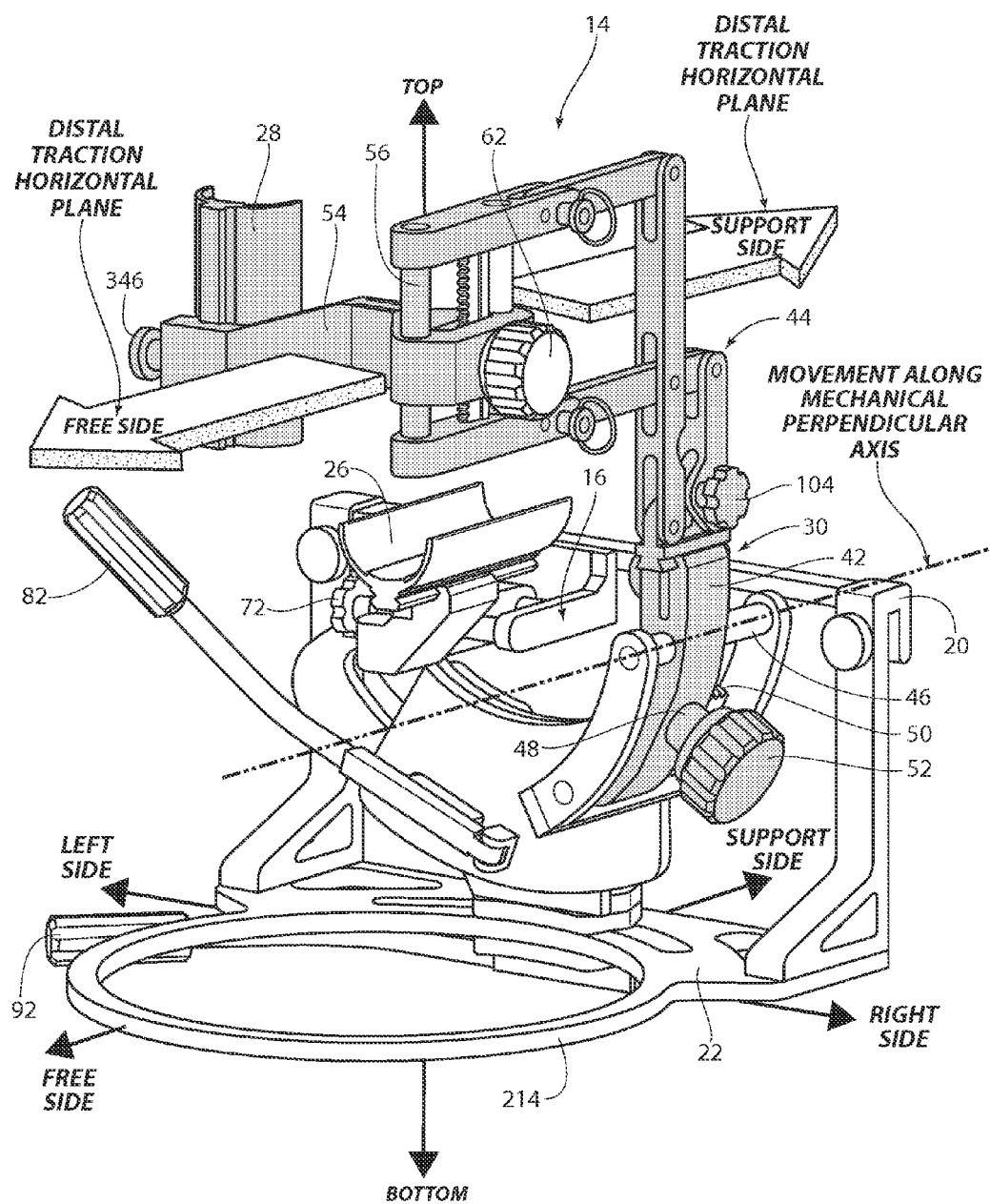
FIGS. 20A to 20C are, respectively, a Free Side perspective view and companion Right Side elevation views of the mechanical bone reduction fixture shown in FIGS. 19A to 19F, with the principal components that function to achieve distal traction shaded for identification, and also identifying the directional points of reference and the principal mechanical axis of movement for distal traction, consistent with FIG. 19A.

With reference to FIG. 20A, it can be seen that the horizontal traction carriage 42 is movable in a linear path in a distal traction horizontal plane along the Mechanical Perpendicular Axis (that is, between the Free Side and the Support Side). In the exemplary embodiment, the horizontal traction carriage 42 moves on a horizontal rail 46, which is supported on a u-shape frame on the Right Side of the fracture reduction fixture 14.

Figure 20B:
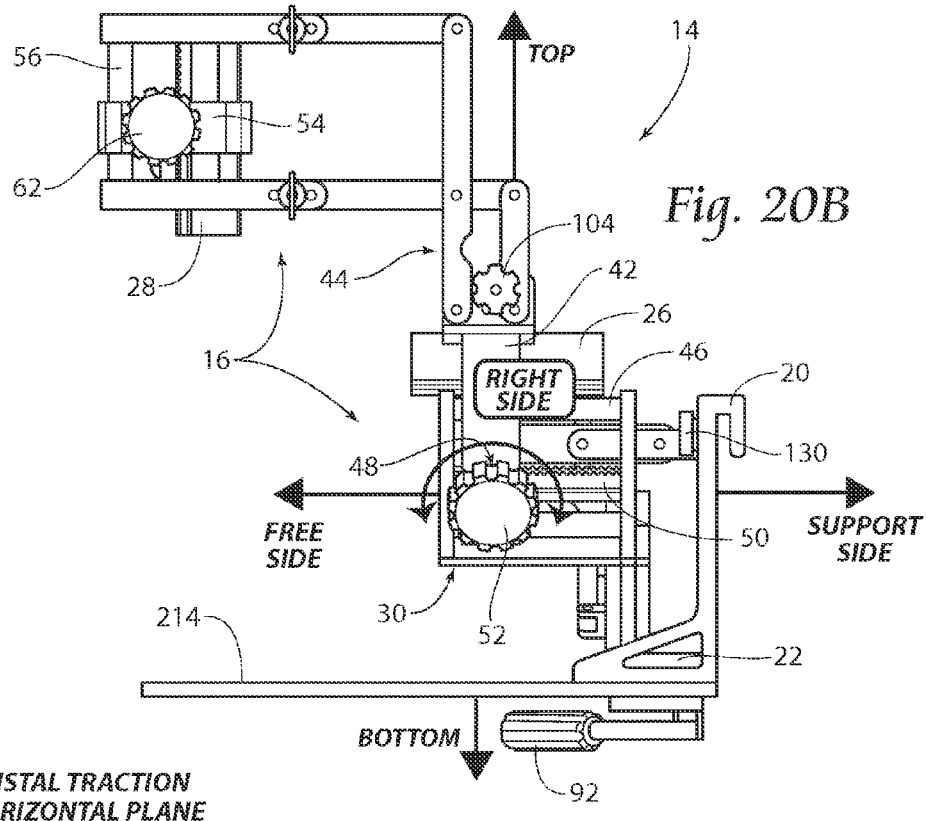
Figure 20C:
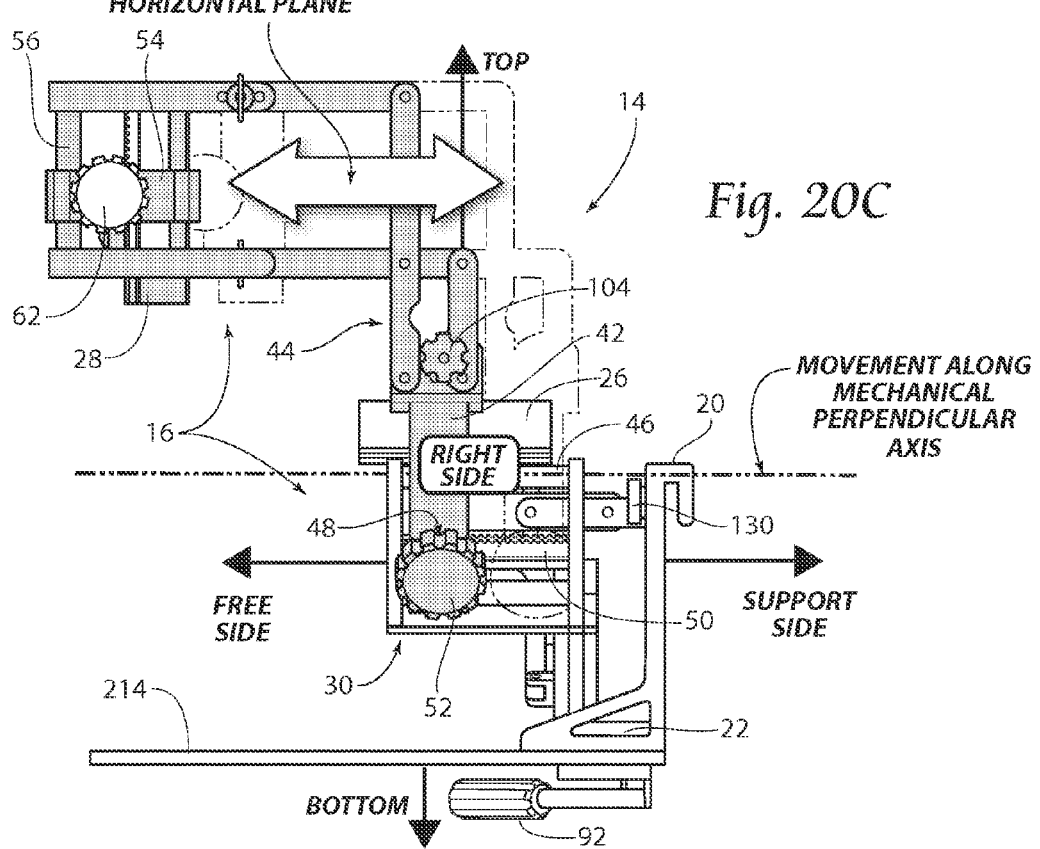

Referring to FIGS. 20A and 20C, the radius/ulna support carriage 28 is structurally coupled by a linkage system 44 to the horizontal traction carriage 42, so that linear movement of the horizontal traction carriage 42 along the horizontal rail 46 likewise linearly moves the radius/ulna support carriage 28 in a parallel path along the Mechanical Perpendicular Axis between the Support Side and the Free Side of the fracture reduction fixture 14. This linear movement can also be considered to be a "translation." This linear movement of the radius/ulna support carriage 28 in tandem with movement of the horizontal traction carriage 42 along the Mechanical Perpendicular Axis of the fracture reduction fixture 14 is also shown from a Right Side perspective in FIG. 20C.

As shown in FIGS. 20A and 20C, the humeral support carriage 26 is not coupled to the horizontal traction carriage 42. Thus, the humeral support carriage 26 remains stationary during linear movement of the horizontal traction carriage 42 along the Mechanical Perpendicular Axis. As a result, linear movement of the horizontal traction carriage 42 also moves the radius/ulna support carriage 28 along the Mechanical Perpendicular Axis laterally closer to or farther from the humeral support carriage 26 (as FIGS. 20B and 20C show).

The distal traction mechanical force reduction assembly 30 moves the horizontal traction carriage 42 in a horizontal plane along the Mechanical Perpendicular Axis toward the Free Side of the fracture reduction fixture 14 to mechanically achieve distal traction of the supracondylar fracture along the Anatomical Reduction Perpendicular Axis of the fracture reduction coordinate system of the supracondylar region (see FIG. 12A) (see FIGS. 20B and 20C). This is because moving the horizontal traction carriage 42 toward the Free Side along the Perpendicular Mechanical Axis also moves the radius/ulna support carriage 28, which holds the distal bone region, in a linear path toward the Free Side farther away from the then-stationary humeral support carriage 26, which holds the proximal bone region, thereby separating the distal bone region and the proximal bone region along the Anatomical Reduction Perpendicular Axis (as FIG. 12C shows).

b. Mechanically Adjusting and Maintaining Distal Traction

In the exemplary embodiment, the distal traction mechanical force reduction assembly 30 includes a distal traction spur gear 48, which rides along a horizontal rack 50. The distal traction spur gear 48 and horizontal rack 50 can be seen in FIG. 20B, 20C, and in a perspective enlarged view in FIGS. 26A and 26B. In this implementation, the distal traction spur gear 48 is advanced along the horizontal rack 50 by rotation of a distal traction control knob 52 on the Right Side of the fracture reduction fixture 14 in a clockwise or counterclockwise direction (see FIGS. 20B and 26A), to reach a desired degree of distal reduction. Advancement of the distal traction spur gear 48 along the horizontal rack 50 in response to rotation of the distal traction control knob 52 allows for micro-control of the distal traction mechanical force assembly. The design of the distal traction spur gear 48 and the horizontal rack 50 maintains the distal traction mechanical force assembly in a fixed position in the absence of rotation of the distal traction control knob. As a further arrangement, the distal traction control knob 52 may be designed to include a locking mechanism so that it can be extended outwardly or pushed inwardly to frictionally resist rotation of the distal traction control knob.

Figure 26A:
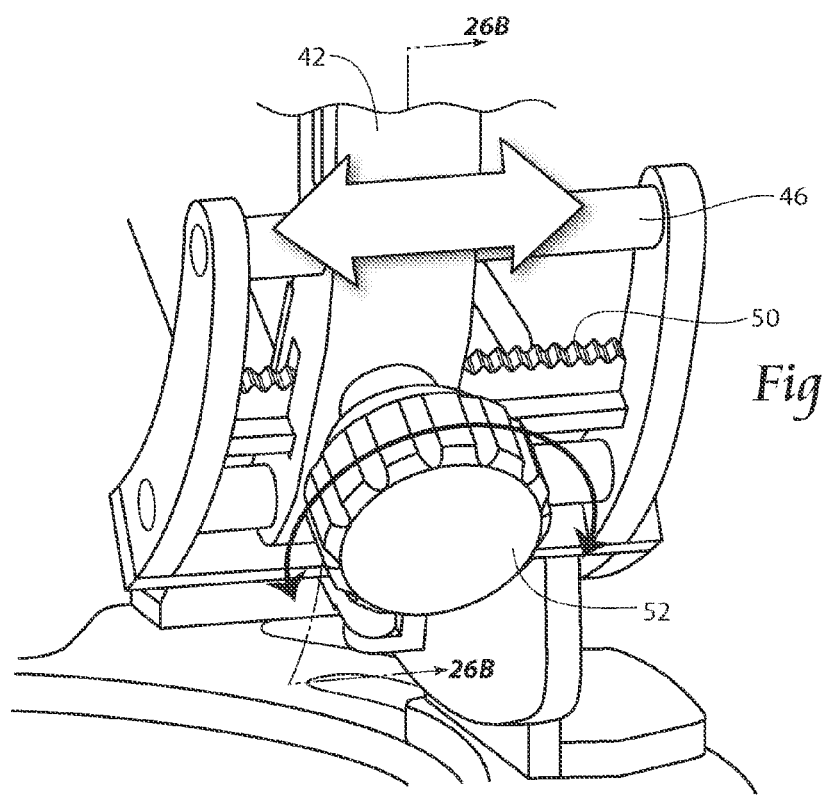
FIGS. 26A and 26B are enlarged Right Side perspective views (with FIG. 26B partially cut away and in section), showing the distal traction spur gear and companion horizontal rack that form a part of the mechanical bone reduction fixture shown in FIGS. 19A to 19F, which function to apply distal traction.
Figure 26B:
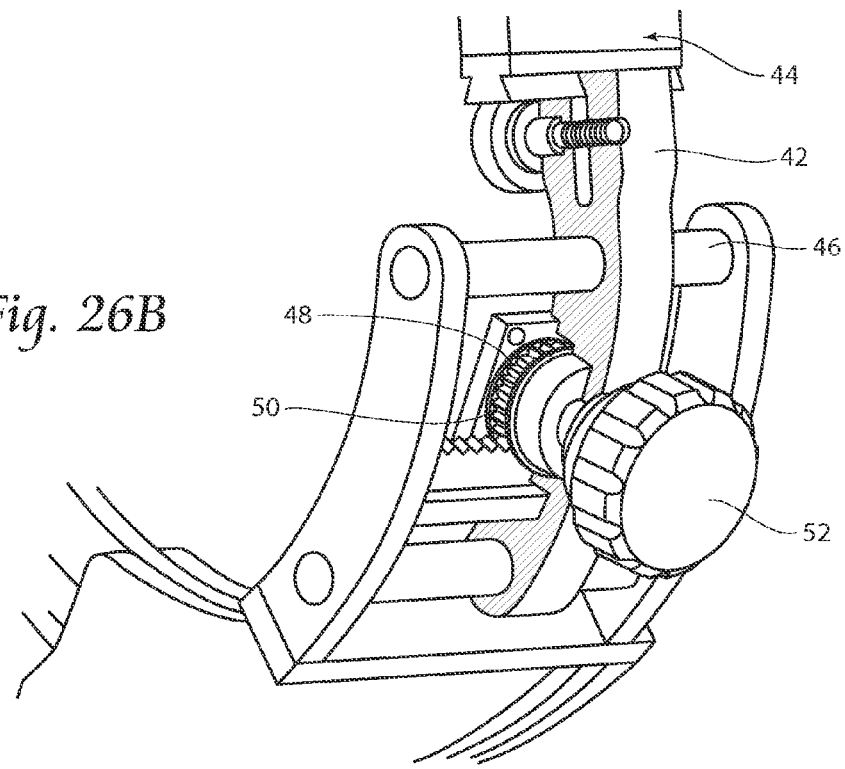

As shown in FIGS. 26A and 26B, rotation of the distal traction control knob 52 results in rotation of the distal traction spur gear 48 and its advancement along the horizontal rack 50. Rotation of the distal traction spur gear 48 along the horizontal rack 50 advances the horizontal traction carriage 42 along the mechanical horizontal axis in precise linear increments in response to rotation of the distal traction spur gear clockwise or counterclockwise, depending on the direction and speed of rotation of the knob 52.

As will be exemplified in greater detail later, the distal traction mechanical force reduction assembly 30 applies mechanical force reduction to achieve distal traction, which can be maintained or locked while other, different mechanical reduction forces are applied by the system 10.

ii. Superior Traction Mechanical Force Reduction Assembly

The superior traction mechanical force reduction assembly 32 mechanically applies and maintains superior traction to the fracture. As before described, and as earlier shown in FIGS. 13A to 13D, superior traction comprises a force vector applied along the Anatomical Reduction Vertical Axis of the fracture reduction coordinate system of the supracondylar region. Superior traction along the Anatomical Reduction Vertical Axis lifts (or, in reverse, lowers) the distal bone region as a unit relative to the proximal bone region, to return proximal and distal bone regions that have been displaced due to the fracture forward or backwards back (as shown in FIG. 9) toward the native state of alignment.

a. Mechanically Achieving Superior Traction

In the exemplary embodiment (initially, referring to FIG. 19A), the superior traction mechanical force reduction assembly 32 comprises a vertical traction carriage 54 structurally coupled to the radius/ulna support carriage 28 by the same linkage system 44 that couples the horizontal traction carriage 42 to the radius/ulna support carriage 28. The vertical traction carriage 54 and the linkage system 44 by which it is mechanically coupled to the radius/ulna support carriage 28, shown in FIG. 19A, are further shaded for identification in FIG. 21A, which (like its companion FIGS. 21B and 21C) also incorporates the directional points of reference and the principal mechanical axis for superior traction established in FIG. 19A.

Figure 21A:
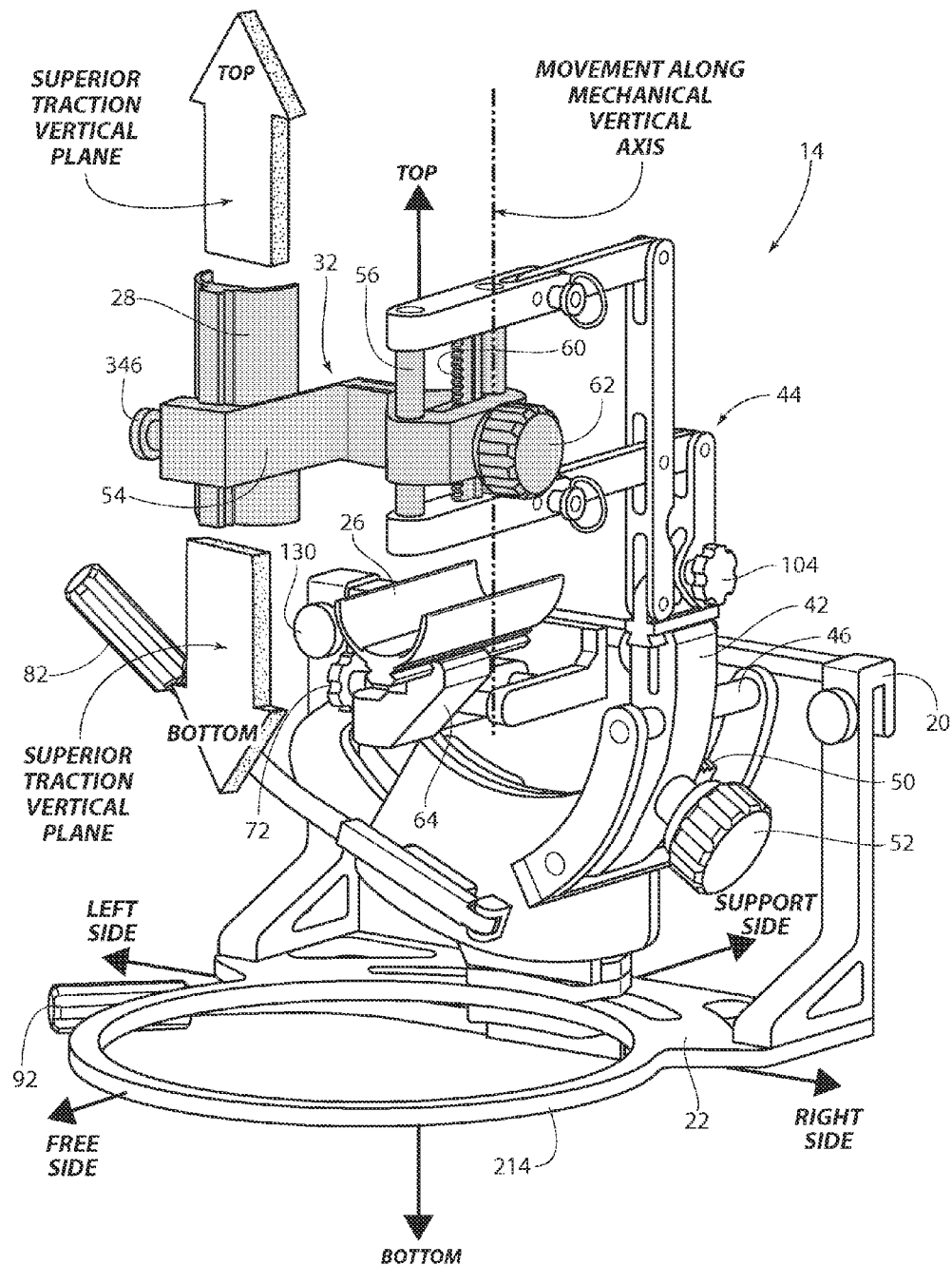
FIGS. 21A to 21C are, respectively, a Free Side perspective view and companion Right Side elevation views of the mechanical bone reduction fixture shown in FIGS. 19A to 19F, with the principal components that function to achieve superior traction shaded for identification, and also identifying the directional points of reference and the principal mechanical axis of movement for superior traction, consistent with FIG. 19A.

With reference to FIG. 21A, it can be seen that the vertical traction carriage 54 is movable in a linear path in a superior traction vertical plane along the Mechanical Vertical Axis (that is, toward the Top and/or toward the Bottom of the fracture reduction fixture 14). The vertical traction carriage 54 moves on a vertical rail 56, which is supported on the linkage system 44 on the Right Side of the fracture reduction frame 22 above the horizontal traction carriage 42.

Figure 21B:
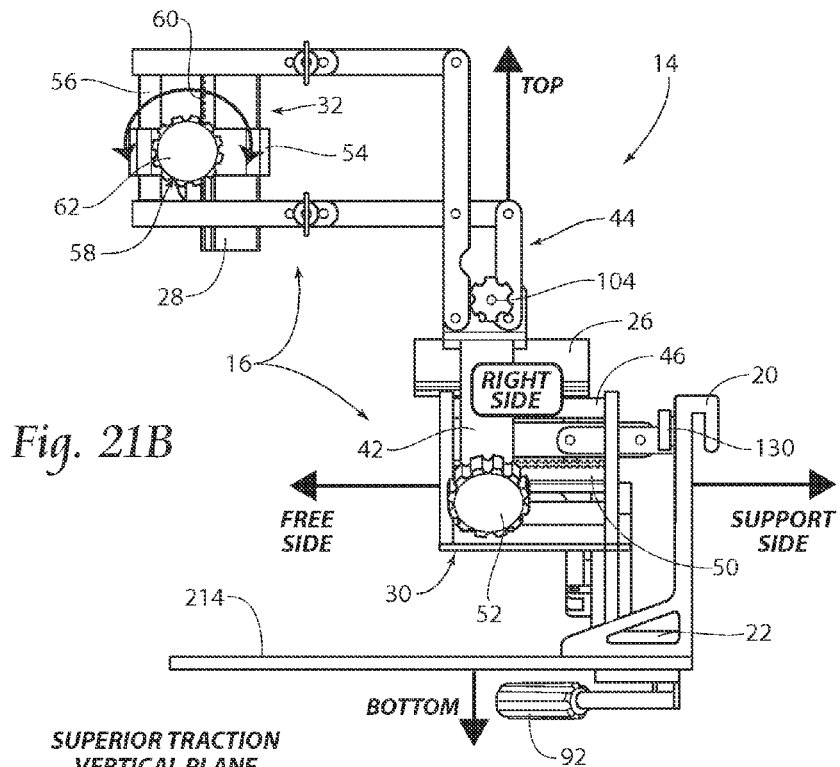
Figure 21C:
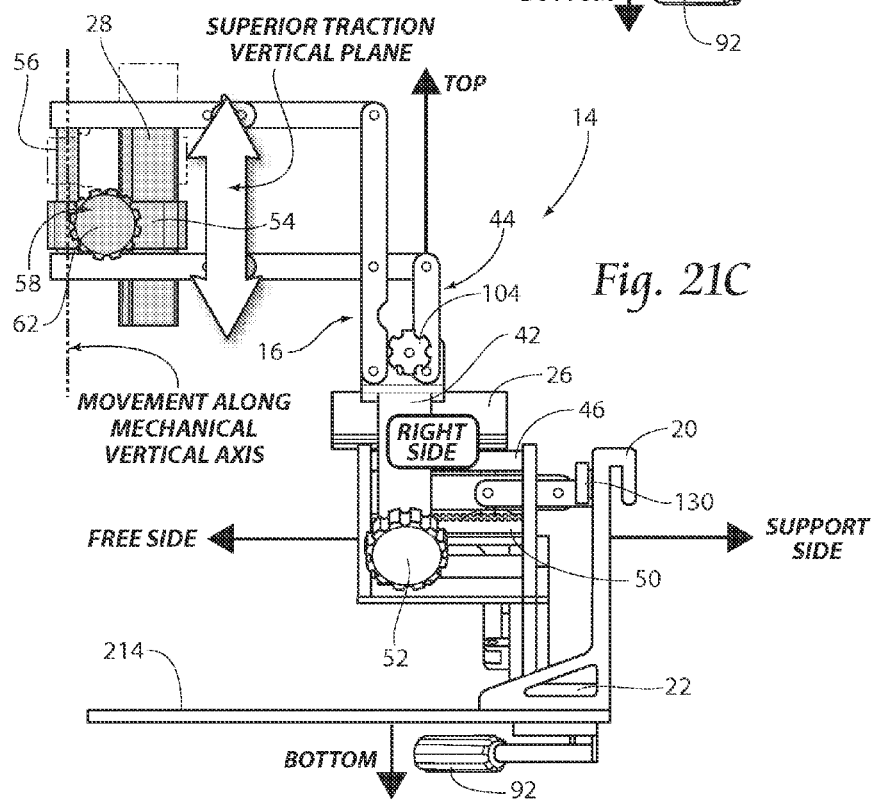

Referring to FIGS. 21A and 21C, the radius/ulna support carriage 28 is structurally coupled to the vertical traction carriage 54, so that linear movement of the vertical traction carriage 54 along the vertical rail 56 likewise moves the radius/ulna support carriage 28 in a parallel path along the Mechanical Vertical Axis between the Top and Bottom of the fracture reduction fixture 14. The linear movement can also be considered to be a "translation." This linear movement of the radius/ulna support carriage 28 in tandem with the vertical traction carriage 54 along the mechanical vertical axis of the fracture reduction fixture 14 is also shown from a Right Side perspective in FIG. 21C).

As shown in FIGS. 21A and 21C, the humeral support carriage 26 is not coupled to the movable vertical traction carriage 54. The humeral support carriage 26 remains stationary during linear movement of the vertical traction carriage 54 along the Mechanical Vertical Axis. As a result, linear movement of the vertical traction carriage 54 along the Mechanical Vertical Axis likewise moves the radius/ulna support carriage 28 along the Mechanical Vertical Axis in a superior traction vertical plane farther from or closer to the humeral support carriage 26 (as FIGS. 21B and 21C show).

The superior traction mechanical force reduction assembly 32 moves the vertical traction carriage 54 in a vertical plane along the Mechanical Vertical Axis toward the Top of the fracture reduction fixture 14 to mechanically achieve superior traction along the Anatomical Reduction Vertical Axis of the fracture reduction coordinate system of the supracondylar region (see FIG. 13A). This is because moving the vertical traction carriage 54 along the Mechanical Vertical Axis toward the Top also moves the radius/ulna support carriage 28 (holding the distal bone region) toward the Top (i.e., superior direction) away from then-stationary humeral support carriage 26 (holding the proximal fracture region), thereby separating the distal bone region and the proximal fracture region along the Anatomical Reduction Vertical Axis (as FIG. 13C shows).

b. Mechanically Adjusting and Maintaining Superior Traction

Figure 22C:
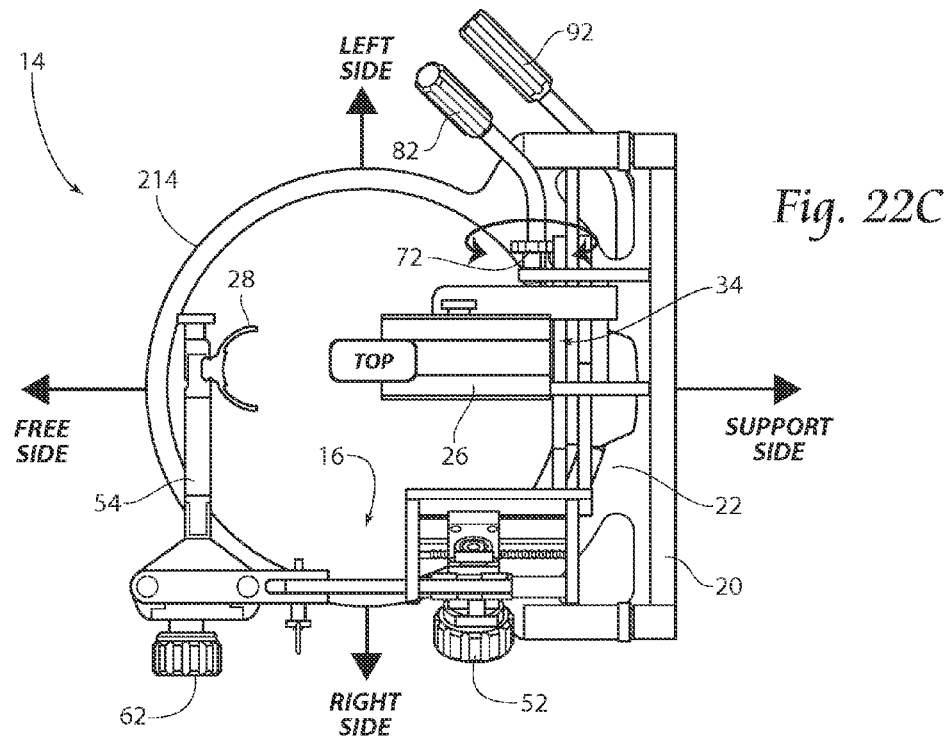

In the exemplary embodiment, the superior traction mechanical force reduction assembly 32 includes a superior traction spur gear 58, which rides along a vertical rack 60, as shown in FIGS. 22B and 22C. The superior traction spur gear 58 and vertical rack 60 of the superior traction mechanical force reduction assembly 32 has the same generally mechanical construction and operation as the distal traction spur gear 48 and companion horizontal rack 50 described in connection with the distal traction mechanical force reduction assembly 30 (shown in FIGS. 26A and 26B).

In this implementation, the superior traction spur gear 58 is advanced along the vertical rack 60 by rotation of a superior traction control knob 62 on the Right Side of the fracture reduction fixture 14 in clockwise or counterclockwise direction, to reach a desired degree of superior traction reduction. The superior traction spur gear 58 and the vertical rack 60 allows for micro-control of the distal traction mechanical force reduction assembly 30. The design of the superior traction spur gear 58 and the vertical rack 60 maintains the distal traction mechanical force reduction assembly 30 in a fixed position in the absence of rotation of the superior traction control knob 62. As a further arrangement, the superior traction control knob 62 may be designed to include a locking mechanism so that it can be extended outwardly or pushed inwardly to frictionally resist rotation of the superior traction control knob 62.

The rotation of the superior traction control knob 62 results in rotation of the superior traction spur gear and its advancement along the vertical rack 60. Rotation of the superior traction spur gear 58 along the rack advances the vertical traction carriage 54 in precise linear increments along the Mechanical Vertical Axis in response to rotation of the superior traction spur gear 58 clockwise or counterclockwise, depending on the direction and speed of rotation of the superior traction control knob 62.

As will be exemplified in greater detail later, the superior traction mechanical force reduction assembly 32 applies mechanical force reduction to achieve superior traction, which can be maintained or locked while other, different mechanical reduction forces are applied by the system.

iii. Lateral Translation Mechanical Force Reduction Assembly

The lateral translation mechanical force reduction assembly 34 mechanically applies and maintains lateral translation or traction to the fracture. As before described, and as earlier shown in FIGS. 14A to 14D, lateral translation comprises a force vector applied along the Anatomical Reduction Horizontal Axis of the fracture reduction coordinate system of the supracondylar region. Lateral translation along the Anatomical Reduction Horizontal Axis moves the fractured end of the distal bone regions across the fractured end of the proximal bone region. Lateral translation returns proximal and distal bone regions that have been medially displaced left or right due to the fracture (as shown in FIGS. 7 and 8) back toward the native state of alignment.

a. Mechanically Achieving Lateral Translation

In the exemplary embodiment (initially, refer to FIGS. 19A and 19B), the lateral translation mechanical force reduction assembly 34 comprises a lateral translation carriage 64. The lateral translation carriage 64 supports the humeral support carriage 26. The lateral translation carriage 64 is best shown in FIGS. 19A and 19B, and is further shaded for identification in FIG. 22A, which (like its companion FIGS. 22C and 22D) also incorporates the directional points of reference and the principal mechanical axis for lateral translation established in FIG. 19A.

With reference to FIG. 22A, it can be seen that the lateral translation carriage 64 comprises a support bed 66 that is carried for movement along the Mechanical Horizontal Axis by a cross bar 68 and a parallel companion threaded cross bolt 70 (see also FIG. 22B), which are mutually coupled between a pair of Left and Right supports cantilevered on the Support Side toward the Free Side of the support mount 20. The humeral support carriage 26 is supported on the support bed 66 (as FIG. 22A shows). The support bed 66 and humeral support carriage 26 are movable along the cross bar 68 and parallel threaded cross bolt 70 in a linear path in a lateral translation horizontal plane along the Mechanical Horizontal Axis (that is, between the Left Side and the Right Side) of the fracture reduction fixture 14.

Figure 22D:
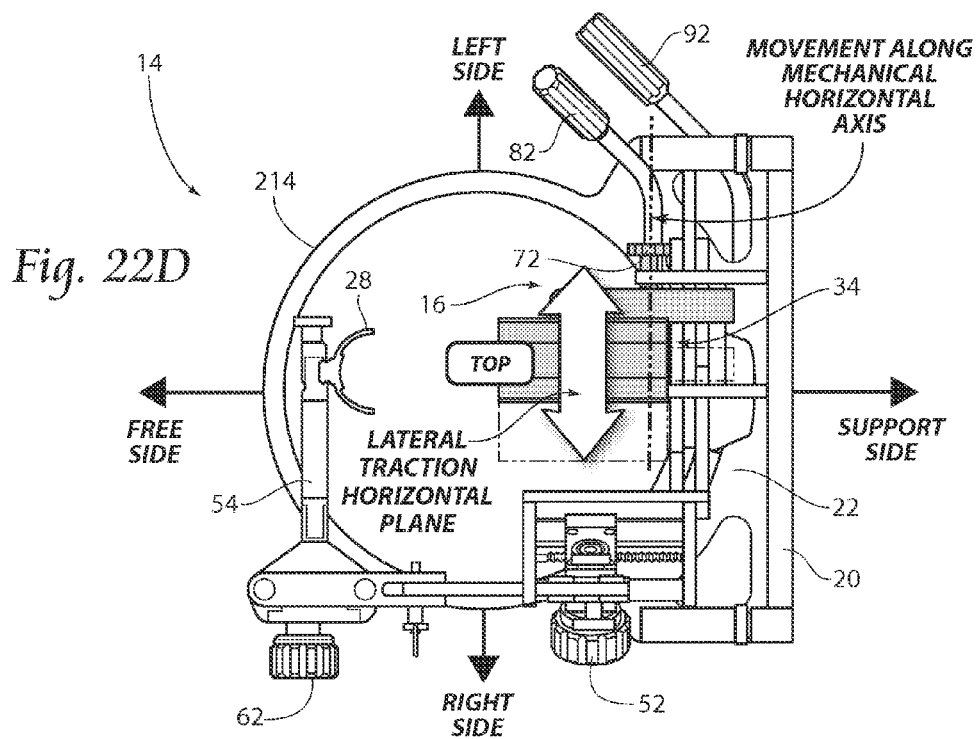

Referring to FIGS. 22A and 22D, the radius/ulna support carriage 28 is not coupled to the lateral translation carriage 64. The radius/ulna support carriage remains stationary during linear movement of the lateral translation carriage 64 along the Mechanical Horizontal Axis. As a result, linear movement of the lateral translation carriage 64 likewise moves the humeral support carriage 26 along the Mechanical Horizontal Axis relative to the radius/ulna support carriage 28 (as FIGS. 22B and 22D show).

The lateral translation mechanical force reduction assembly 34 moves the lateral translation carriage 64 in a horizontal plane along the Mechanical Horizontal Axis between the Left Side and Right Side of the fracture reduction fixture 14 to mechanically achieve lateral translation along the Anatomical Reduction Horizontal Axis of the fracture reduction coordinate system of the supracondylar region (see FIG. 15A), as mechanically shown in FIGS. 22B and 22D. This is because the proximal bone region, which is held by the humeral support carried by the Right and Left moving lateral translation carriage 64, is moved, respectively, to the Right and to the Left along the Anatomical Reduction Horizontal Axis relative to the distal fracture region, which is held in the then-stationary radius/ulna support carriage 28. The lateral translation mechanical force reduction assembly 34 thereby mechanically returns proximal and distal bone regions that have been medially displaced along Anatomical Reduction Horizontal Axis back toward the native state of alignment (as FIG. 14C shows).

b. Mechanically Adjusting and Maintaining Lateral Translation

In the exemplary embodiment, the pace and direction of linear movement of the lateral translation carriage 64 along the mechanical horizontal axis are incrementally controlled by a lateral translation control knob 72 on the Left Side of the fracture reduction assembly 34. The lateral translation control knob 72 is coupled to the threaded cross bolt 70, such that rotation of the lateral translation control knob 72 in a clockwise or counterclockwise direction rotates the threaded cross bolt 70 in a corresponding direction. The region of the support bed 66 that rides along the threaded cross bolt 70 is itself helically threaded to mate with the helical threads of the threaded cross bolt 70 to advance the support bed 66 of the lateral translation carriage 64 along the Mechanical Horizontal Axis in precise linear increments in response to rotation of the threaded cross bolt 70 (see FIGS. 22C and 22D). The design of the threaded interface between the threaded cross bolt 70 and support bed 66 maintains the lateral translation force reduction assembly in a fixed position in the absence of rotation of the lateral translation control knob 72. As a further arrangement, the lateral translation control knob 72 may be designed to include a locking mechanism so that it can be extended outwardly or pushed inwardly to frictionally resist rotation of the lateral translation control knob 72.

As will be exemplified in greater detail later, the lateral translation mechanical force reduction assembly 34 applies mechanical force reduction to achieve lateral translation, which can be maintained or locked while other, different mechanical reduction forces are applied by the system.

iv. Varus/Valgus Rotation Mechanical Force Reduction Assembly

The varus/valgus rotation mechanical force reduction assembly 36 mechanically applies and maintains varus/valgus rotation to the fracture. As before described, and as earlier shown in FIGS. 15A to 15D, varus/valgus rotation comprises a rotational force vector (torque) applied about the Anatomic Reduction Perpendicular Axis of the fracture reduction coordinate system of the supracondylar region. Varus/valgus rotation about the Anatomic Reduction Perpendicular Axis pivots the fractured end of the distal bone region about the longitudinal axis of the proximal bone region. Varus/valgus rotation returns proximal and distal bone regions that have been rotationally displaced due to the fracture (as shown in FIG. 10) back toward the native state of alignment.

Varus/valgus rotation serves to bring back into native alignment the posterior, anterior, and medial cortical surfaces along the fracture line.

a. Mechanically Achieving Varus/Valgus Rotation

In the exemplary embodiment (initially, refer to FIGS. 19A and 19D), the varus/valgus rotation mechanical force reduction assembly 36 comprises a rocking carriage 74 that is structurally coupled to the radius/ulna support carriage 28 by the same linkage system 44 that couples the horizontal traction carriage 42 to the radius/ulna support carriage 28. The rocking carriage 74 and the linkage system 44 by which it is coupled to the radius/ulna support carriage 28 are best shown in FIG. 19D, and are further shaded for identification in FIG. 23A. Like its companion FIGS. 23C and 23D, FIG. 23A also incorporates the directional points of reference and the principal mechanical axis for varus/valgus rotation established in FIG. 19A.

With reference first to FIGS. 19A and 19B, in the exemplary embodiment, it can be seen that the rocking carriage 74 is carried for movement along a curvilinear track 76. The curvilinear track 76 is formed on a support base 78 that carries the rocking carriage 74 on the frame 22 of the fracture reduction fixture 14. As the rocking carriage 74 is moved along this curvilinear track 76, the radius/ulna support carriage 28 (which is coupled to the rocking carriage 74 by the linkage system 44 shaded in FIG. 23A) correspondingly rotates in a rocking motion relative to the Mechanical Perpendicular Axis in a Leftward or Rightward path (see FIGS. 23A and 23D). The rocking movement of the radius/ulna support carriage 28 along this path can also be considered to be "pivoting" about the Mechanical Perpendicular Axis. The rocking movement of the radius/ulna support carriage 28 along this path about the Mechanical Perpendicular Axis in tandem with the rocking carriage 74 is also shown from a Free Side perspective in FIG. 23D.

Figure 23C:
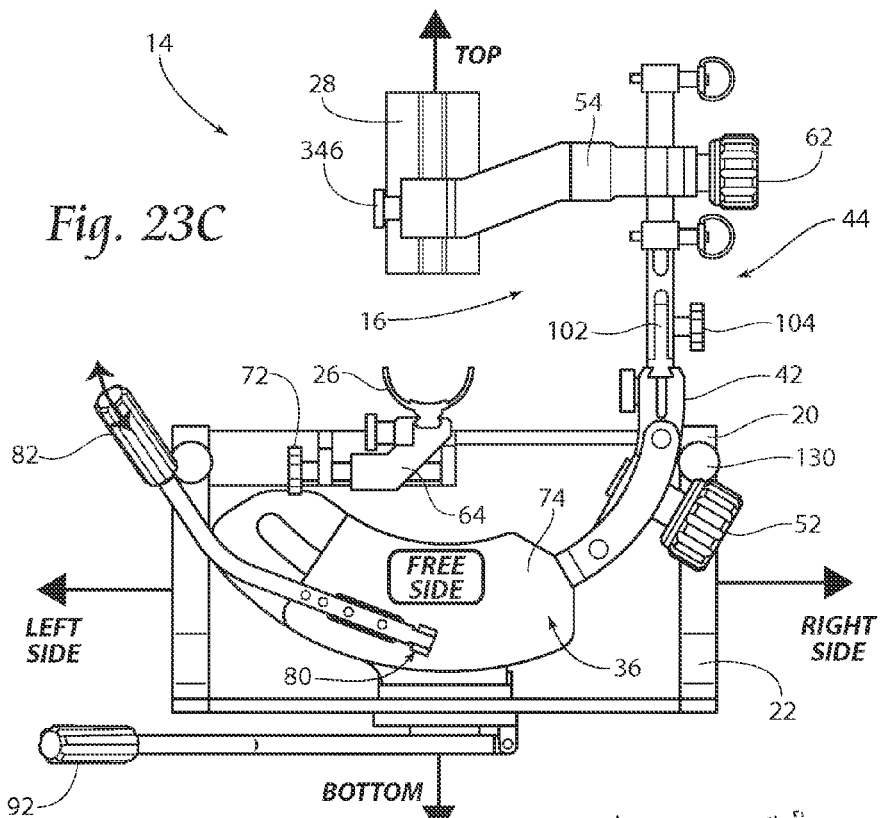
Figure 23D:
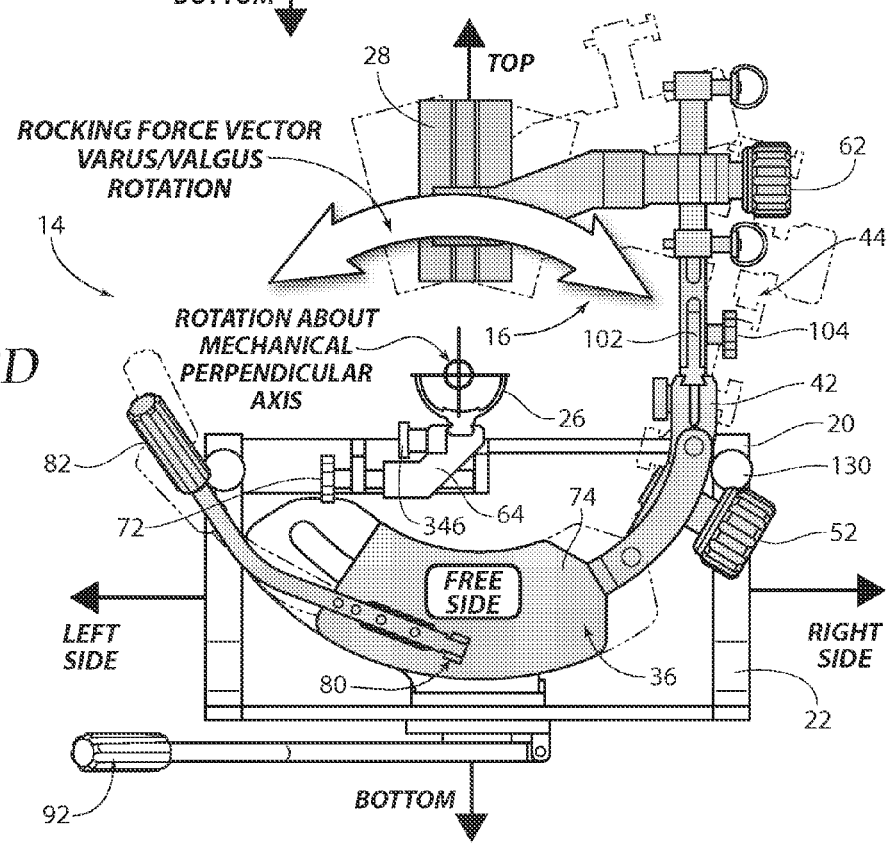

As companion FIG. 23D shows, the varus/valgus rotational mechanical force reduction assembly rocks the radius/ulna support carriage 28 relative to the Mechanical Perpendicular Axis in a Left direction (Leftward) and Right direction (Rightward).

As FIGS. 23A, 23C, and 23D show, the humeral support carriage 26 is not coupled to the rocking carriage 74 or to the linkage system 44 that is structurally coupled it to the radius/ulna support carriage 28. The humeral support carriage 26 remains stationary as the rocking carriage 74 (and, with it, the radius/ulna support carriage 28) rock Leftward and Rightward relative to the Mechanical Perpendicular Axis. As a result, the radius/ulna support carriage 28 rocks Rightward and Leftward relative to the stationary humeral support carriage 26 (as FIG. 23D shows).

The varus/valgus rotation mechanical force reduction assembly 36 rocks the radius/ulna support carriage 28 Leftward and Rightward relative to the Mechanical Perpendicular Axis to mechanically achieve varus/valgus rotation about the Anatomic Perpendicular Axis of the fracture reduction coordinate system of the supracondylar region (see FIG. 15A). By rocking the radius/ulna support carriage 28 Rightward and Leftward about the Mechanical Perpendicular Axis relative to the stationary humeral support carriage 26, a rotational force vector (torque) is applied about the Mechanical Perpendicular Axis to the fractured end of the distal bone region (held in the radius/ulna support carriage 28). The varus/valgus rotation force, mechanically applied by the varus/valgus rotation mechanical force reduction assembly 36, pivots the fractured end of the distal bone region about the Anatomical Perpendicular Axis, to return the proximal and distal bone regions, which have been rotationally displaced due to the fracture (as shown in FIG. 10), back toward the native state of alignment (as FIG. 15C shows).

b. Mechanically Adjusting and Maintaining Varus/Valgus Rotation

In the exemplary embodiment (see FIG. 23A), the pace and direction of movement of the rocking carriage 74 of the varus/valgus rotation mechanical force reduction assembly 36 along the track are controlled by a varus/valgus control mechanism 80 on the Free Side of the rocking carriage 74.

In the exemplary embodiment, the varus/valgus control mechanism 80 (also see FIG. 23B) includes a control handle 82 and a frictional brake 84 carried by the control handle 82. The control handle 82 is pivotally attached to the rocking carriage 74 for manual movement away from the rocking carriage 74 into an unlocked position (i.e., toward the Free Side, as shown in solid lines in FIG. 23B) and toward the rocking carriage 74 into a locked position (i.e., toward the Support Side, as shown in phantom lines in FIG. 23B).

When the control handle 82 is in the locked position, the frictional brake 84 makes frictional contact with a side of the support base 78, to fractionally resist movement of the rocking carriage 74 along the track 76. Conversely, when the control handle 82 is in the unlocked position, the frictional brake 84 is free from frictional contact with a side of the support base 78, movement of the rocking carriage 74 along the track 76 by external manual force applied by the caregiver or surgeon to the control handle 82 is permitted. The control handle 82 may be elongated, as the exemplary embodiment shows, to provide the caregiver or surgeon with a lever arm and a mechanical advantage in controlling movement of the rocking carriage 74.

By moving the control handle 82 into the unlocked position, the brake 84 is disengaged, thereby allowing rocking movement of the radius/ulna support carriage 28 Leftward and Rightward relative to the Mechanical Perpendicular Axis by applying a Leftward or Rightward force to the control handle. This provides the previously described rocking movement, which allows the caregiver or surgeon to rock the radius/ulna support carrier Left-ward and Right-ward by the application a manual rocking force upon the rocking carriage 74. When the desired degree of varus/valgus rotation is achieved, the caregiver or surgeon moves the control handle 82 into the locked position, thereby engaging the friction brake 84, to secure the rocking carriage 74 in the desired position. The control handle 82 can include a over-center locking mechanism to resist movement of the control handle 82 out of the locked position until a requisite unlocking force is applied to the control handle 82.

In the exemplary embodiment, the pace of varus/valgus rotation is incrementally controlled by manual force applied by the surgeon or caregiver (see FIG. 68) in a macro-condition. In the exemplary embodiment, there is no micro-condition of varus/valgus rotation, as reducing in this plane typically does not require micro-incremental alignment.

As will be exemplified in greater detail later, the varus/valgus rotation mechanical force reduction assembly applies mechanical force reduction to achieve varus/valgus rotational alignment, which can be maintained by the varus/valgus control handle mechanism, while other, different mechanical reduction forces are applied by the system 10.

v. Pronation/Supination Rotation Mechanical Force Reduction Assembly

The pronation/supination rotation mechanical force reduction assembly 38 mechanically applies and maintains pronation/supination rotation to the fracture. As before described, and as earlier shown in FIGS. 16A to 16D, pronation/supination rotation comprises a rotational force vector (torque) applied about the Anatomical Reduction Vertical Axis of the fracture reduction coordinate system of the supracondylar region. Pronation/supination rotation about the Anatomical Reduction Vertical Axis pivots the fractured end of the distal bone region about the longitudinal axis of distal bone region. Like varus/valgus rotation, pronation/supination rotation returns proximal and distal bone regions that have been rotationally displaced due to the fracture (as shown in FIG. 10) back toward the native state of alignment. Pronation/supination rotation also serves to bring back into native alignment the posterior, anterior, and medial cortical surfaces along the fracture line.

a. Mechanically Achieving Pronation/Supination Rotation

Figure 24C:
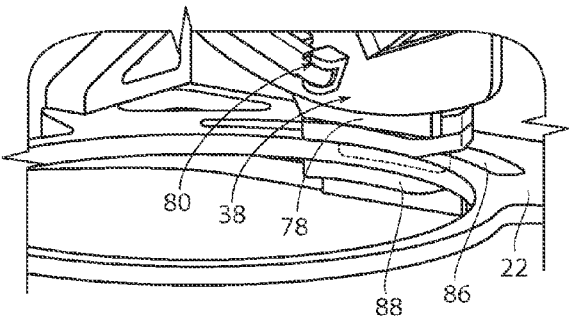

In the exemplary embodiment (initially, referring to FIGS. 19B and 19D), the pronation/supination rotation mechanical force reduction assembly 38 comprises a horizontal curvilinear slot 86 on the frame 22 of the fracture reduction fixture 14, along which a guide 88 depending from the support base 78 rides (see also FIG. 24C). As the guide 88 follows the path of the slot 86, the support base 78 itself travels along the curvilinear path of the slot 86. As the support base 78 travels along the slot 86, the radius/ulna support carriage 28 (which is coupled via the rocking carriage 74 and linkage system to the support base 78) is itself caused to rotate in a swinging motion about an axis that is generally parallel to the Mechanical Vertical Axis. The geometric center of the slot 86 defines a virtual center of rotation for the pronation/supination rotation mechanical force reduction assembly 38, about which the radius/ulna support carriage 28 swings.

The assemblage of components of the pronation/supination rotation mechanical force reduction assembly 38, as just described, is best shown in FIG. 19B. They are further shaded for identification in FIG. 23A. FIG. 23A, like its companion FIGS. 24D and 24E, also incorporate the directional points of reference and identify the principal mechanical axis for pronation/supination rotation established in FIG. 19A.

Figure 24D:
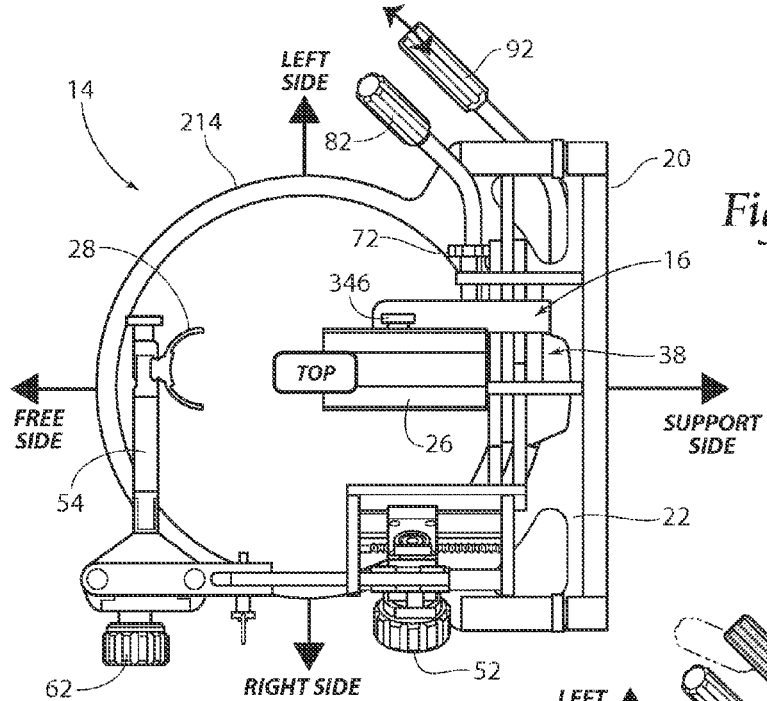
Figure 24E:
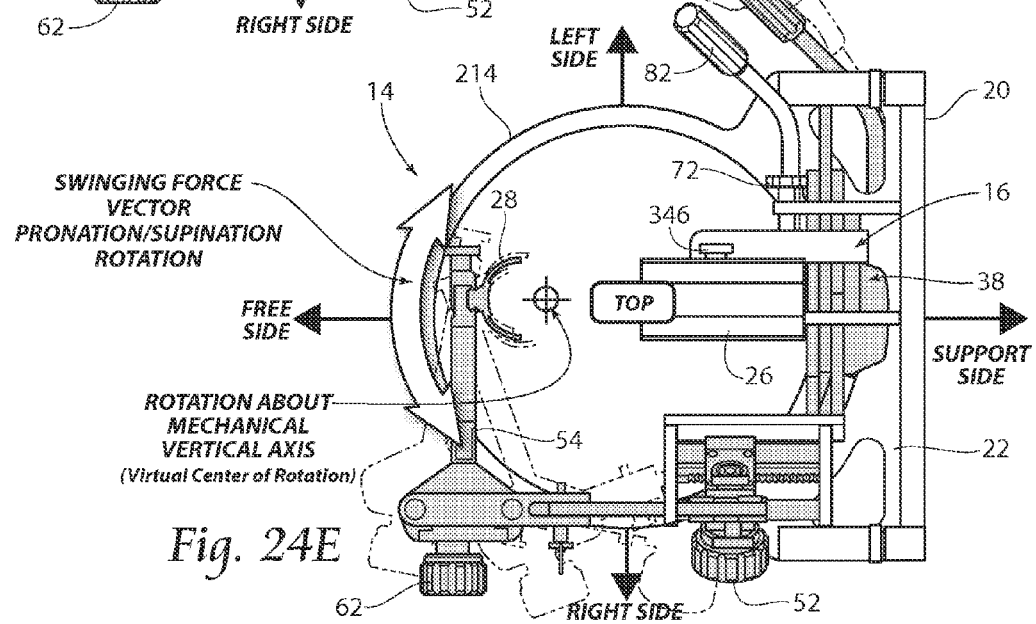

As a comparison of FIG. 24E and FIG. 23D show, the pronation/supination rotation mechanical force reduction assembly 38 (FIG. 24E) causes the radius/ulna support carriage 28 to rotate about an axis that is different than the rocking axis of the radius/ulna support carriage 28 brought about by the varus/valgus rotation mechanical force reduction assembly 36 (FIG. 23D). Whereas the varus/valgus rotation mechanical force reduction assembly 36 causes the radius/ulna support carriage 28 to rock relative to an axis generally parallel to the Mechanical Perpendicular Axis, the pronation/supination rotation mechanical force reduction assembly 38 causes the radius/ulna support carriage 28 to rotate about an axis that is generally parallel to the Mechanical Vertical Axis. The pronation/supination rotation mechanical force reduction assembly 38 establishes a virtual center of rotation for the radius/ulna support carriage 28 (see FIGS. 24A and 24D) that extends generally parallel to the Mechanical Vertical Axis.

The result is the application of rotational force vectors (torques) to the fracture that substantially differ. The varus/vulgas rotation (rocking relative to the Mechanical Perpendicular Axis) applies a rocking force vector to the radius/ulna support carriage 28. The pronation/supination rotation (rotating relative to the Mechanical Vertical Axis) applies a rotating or swinging force vector to the radius/ulna support carriage 28.

The humeral support carriage 26 is not coupled to the support base 78 or the linkage system 44 that structurally couples it to the radius/ulna support carriage 28. The humeral support carriage 26 remains stationary as the radius/ulna support carriage 28 rotates or swings in the horizontal plane Leftward and Rightward about the Mechanical Vertical Axis. As a result, the radius/ulna carriage swings Leftward and Rightward relative to the stationary humeral support carriage 26 (as FIG. 24D shows).

The pronation/supination rotation mechanical force reduction assembly 38 rotates or swings the radius/ulna support carriage 28 about an axis parallel to the Mechanical Vertical Axis to mechanically achieve pronation/supination rotation about the Anatomic Vertical Axis of the fracture reduction coordinate system of the supracondylar region (see FIG. 16A). By rotating or swinging the radius/ulna support carriage 28 Rightward and Leftward about the Mechanical Vertical Axis relative to the stationary humeral support carriage 26, a rotational force vector (torque) is applied about the Mechanical Vertical Axis to the fractured end of the distal bone region (held in the radius/ulna support carriage 28). The pronation/supination rotation force, mechanically applied by the pronation/supination rotation mechanical force reduction assembly 38, pivots the fractured end of the distal bone region about the longitudinal axis of distal bone region.

b. Mechanically Adjusting and Maintaining Pronation/Supination Rotation

In the exemplary embodiment (see, in particular, FIGS. 24A, 24B and 24C), the pace and direction of advancement of the support base along the slot 86 are controlled by a pronation/supination control mechanism 90 on the Left Side/Bottom of the support base.

In the exemplary example, the pronation/supination control mechanism 90 includes a control handle 92 and a frictional brake 94 carried by the control handle 92 (see FIG. 24B). The control handle 92 is pivotally attached to the support base 78 for manual movement away from the support base 78 into an unlocked position (i.e., toward the Support Side, as shown in solid lines in FIG. 24B) and toward the support base 78 into a locked position (i.e., toward the Free Side, as shown in phantom lines in FIG. 24B).

The support base 78 includes a Bottom side that projects below the guide 88 (see FIG. 24C). When the control handle 92 is in the locked position, the frictional brake 94 on the Support side of the frame 22 makes frictional contact with the Bottom side of the support base 78 (shown in phantom lines see FIG. 24B), to resist movement of the support base 78 along the slot 86. Conversely, when the control handle 92 is in the unlocked position, the frictional brake 94 is free from frictional contact with the Bottom side of the support base 78, and movement of the support base 78 along the slot 86 by external manual force applied by the caregiver or surgeon to the control handle 92 is permitted. The control handle 92 may be elongated, as the exemplary embodiment shows, to provide the caregiver or surgeon with a lever arm and a mechanical advantage in controlling movement of the support base 78.

By moving the control handle 92 into the unlocked position, the brake 94 is disengaged, thereby allowing swinging movement of the radius/ulna support carriage 28 Leftward and Rightward freely about the Mechanical Vertical Axis by applying a Leftward or Rightward force to the control handle 92. This provides the previously described swinging movement, which allows the caregiver or surgeon to swing of the radius/ulna support carrier Leftward and Rightward by the application a manual swinging force upon the support base 78. When the desired degree of pronation/supination rotation is achieved, the caregiver or surgeon moves the control handle 92 into the locked position, thereby engaging the frictional brake 94, to secure the support base 78 in the desired position. The control handle 92 can include an over-center locking mechanism to resist movement of the control handle 92 out of the locked position until a requisite unlocking force is applied to the control handle 92.

In the exemplary embodiment, the pace of pronation/supination rotation is incrementally controlled by manual force applied by the surgeon or caregiver (see FIG. 72) in a macro-condition. In the exemplary embodiment, there is no micro-condition of pronation/suprination rotation, as reducing in this plane typically does not require micro-incremental alignment.

vi. Flexion/Extension Rotation Mechanical Force Reduction Assembly

The flexion/extension rotation mechanical force reduction assembly mechanically applies and maintains flexion/extension rotation to the fracture. As before described, and as earlier shown in FIGS. 17A to 17D, flexion/extension rotation comprises a rotational force vector (torque) applied about the Anatomical Reduction Horizontal Axis of the fracture reduction coordinate system of the supracondylar region. Flexion/extension rotation about the Anatomical Reduction Horizontal Axis pivots the fractured end of the distal bone region toward the fractured end of the proximal bone region. Flexion/extension rotation returns the fractures ends of the proximal and distal bone regions that have been separated due to the fracture back toward the native state of alignment.

a. Mechanically Achieving Flexion/Extension Rotation

In the exemplary embodiment (initially, refer to FIGS. 19A, 19B, 19E, and 19F), the flexion/extension rotation mechanical force reduction assembly 40 forms a part of the linkage system 44 that couples the radius/ulna support carriage 28 to the horizontal traction carriage 42, vertical traction carriage 54, and the rocking carriage 74.

In the exemplary embodiment (with reference principally to FIG. 19A), the flexion/extension rotation mechanical force reduction assembly 40 comprises a first linkage section 96 pivotally connected to the horizontal traction carriage 42. The first linkage section 96 comprises a vertical long bar 96A, a vertical short bar 96B, and pivotally coupled cross bars 96C, which together form a first articulating parallelogram.

With continued reference principally to FIG. 19A), the flexion/extension rotation mechanical force reduction assembly 40 further comprises a second linkage section 98 pivotally connected to the first linkage section 96. The second linkage section 98 comprises a horizontal top bar 98A and a horizontal bottom bar 98B. The horizontal top bar 98A and the horizontal bottom bar 98B are coupled on the Support Side to the vertical long bar 96A of the first linkage section 96, and on the Free Side to the vertical rail 56 supporting the vertical traction carriage 54. Together, the second linkage section 98 forms a second articulating parallelogram.

The first articulating parallelogram 96 and the second articulating parallelogram 98 couple the horizontal traction carriage 42 to the vertical traction carriage 54, and thereby link the radius/ulna support carriage 28 to the parallelograms 96 and 98 that comprise the flexion/extension rotation mechanical force reduction assembly 40.

Figure 25A:
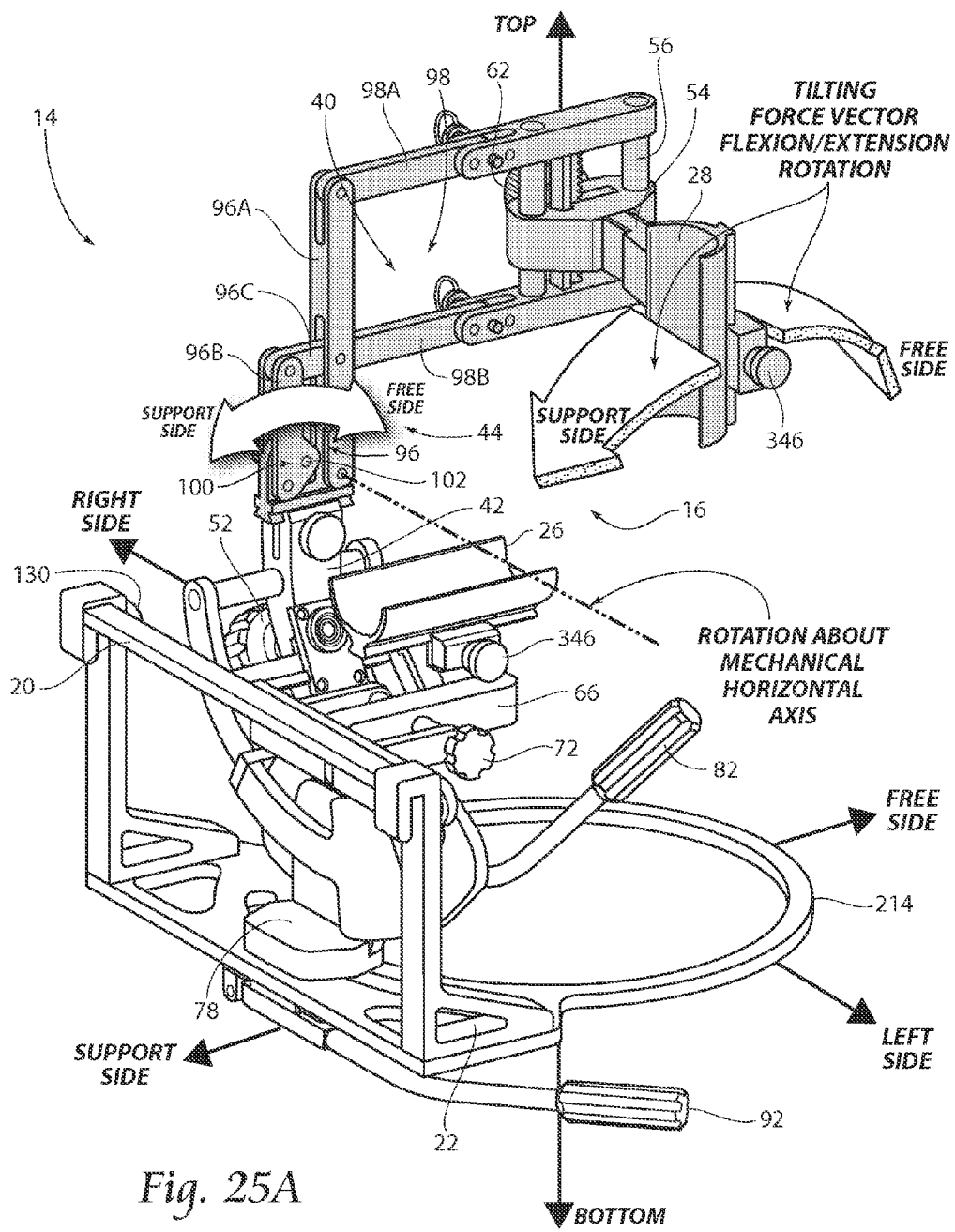
FIGS. 25A to 25C are, respectively, a Support Side perspective view, an enlarged partial Top view and companion Right Side elevation views of the mechanical bone reduction fixture shown in FIGS. 19A to 19F, with the principal components that function to achieve flexion/extension rotation shaded for identification, and also identifying the directional points of reference and the principal mechanical axis of movement for flexion/extension rotation, consistent with FIG. 19A.
Figure 25B:
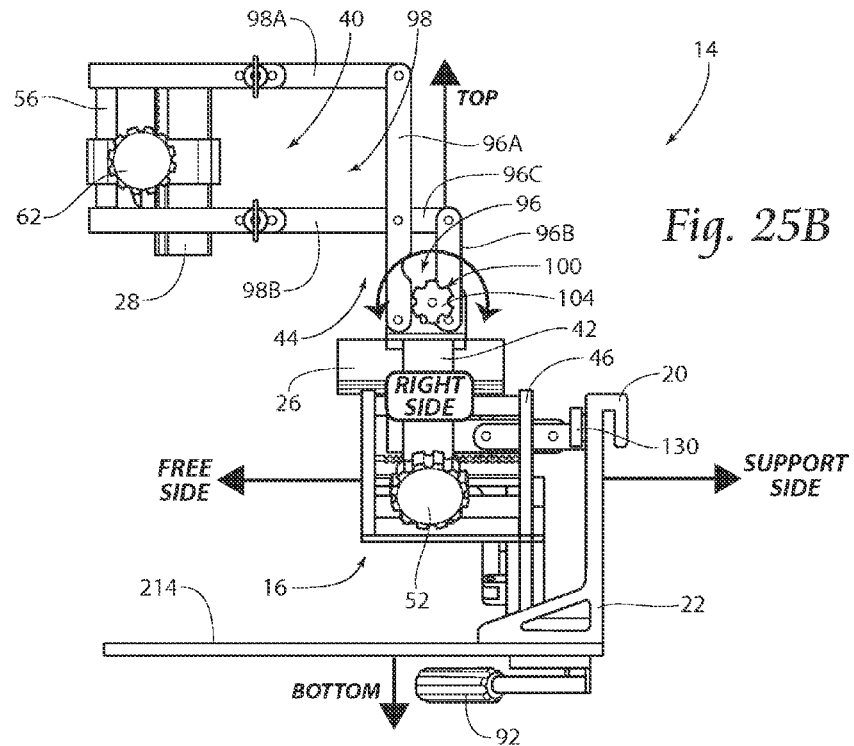

The assemblage of components of the flexion/extension rotation mechanical force reduction assembly 40, as just described, are shaded for identification in FIG. 25A. FIG. 25A, like its companion FIGS. 25B and 25C, also incorporate the directional points of reference and identify the principal mechanical axis for flexion/extension rotation established in FIG. 19A.

Figure 25C:
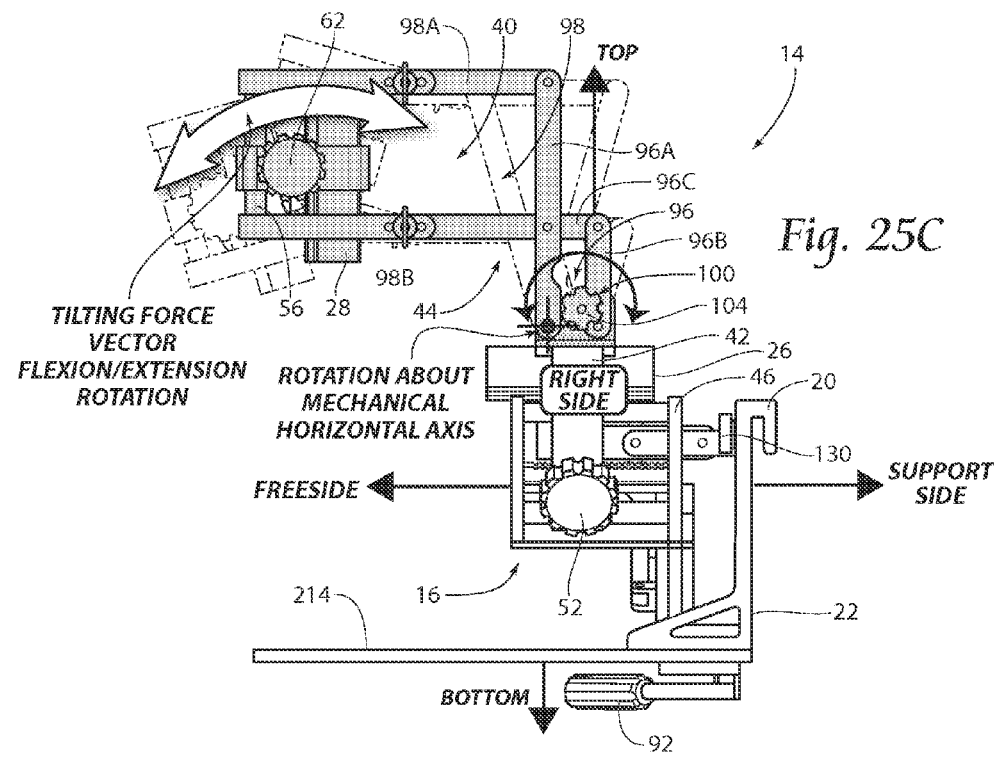

As shown in FIG. 25C, due to the interconnected first and second parallelograms 96 and 98 that form the flexion/extension rotation mechanical force reduction assembly 40, the radius/ulna support carriage 28 can be tilted about the Mechanical Horizontal Axis in the direction of the Free Side or in the direction of the Support Side of the fracture reduction fixture 14. More particularly, the radius/ulna support carriage 28 can be tilted from a normal, upright position (see FIG. 25B), toward the Free Side or toward the Support Side (see FIG. 25C).

As a comparison of FIGS. 25C, 24E, and 23D show, the flexion/extension rotation mechanical force reduction assembly 40 (FIG. 25C) causes the radius/ulna support carriage 28 to tilt about an axis that is different than the swinging axis of radius/ulna support carriage 28 brought about by the pronation/supination rotation mechanical force reduction assembly 38 (FIG. 24E), and that is different than the rocking axis of the radius/ulna support carriage 28 brought about by the varus/valgus rotation mechanical force reduction assembly 36 (FIG. 23D). Whereas the flexion/extension rotation mechanical force reduction assembly 40 causes the radius/ulna support carriage 28 to tilt relative to an axis generally parallel to the Mechanical Horizontal Axis, the pronation/supination rotation mechanical force reduction assembly 38 causes the radius/ulna support carriage 28 to swing about an axis that is generally parallel to the Mechanical Vertical Axis, and the varus/valgus rotation mechanical force reduction assembly 36 causes the radius/ulna support carriage 28 to rock relative to an axis generally parallel to the Mechanical Perpendicular Axis.

The result is the application of rotational force vectors (torques) to the fracture that substantially differ. The flexion/extension rotation mechanical force reduction assembly 40 (tilting relative to the Mechanical Horizontal Axis) applies a tilting force vector to the radius/ulna support carriage 28. The pronation/supination rotation (rotating relative to the Mechanical Vertical Axis) applies a rotating or swinging force vector to the radius/ulna support carriage 28. The varus/vulgas rotation (rocking relative to the Mechanical Perpendicular Axis) applies a rocking force vector to the radius/ulna support carriage 28.

The humeral support carriage 26 is not coupled to the linkage system 44 coupled to the radius/ulna support carriage 28. The humeral support carriage 26 remains stationary as the radius/ulna support carriage 28 tilts toward the Free Side or toward the Support Side. As a result, the radius/ulna support carriage 28 tilts relative to the stationary humeral support carriage 26 (as FIG. 25C shows).

The flexion/extension rotation mechanical force reduction assembly 40 tilts the radius/ulna support carriage 28 about an axis parallel to the Mechanical Horizontal Axis to mechanically achieve flexion/extension rotation about the Anatomical Reduction Horizontal Axis of the fracture reduction coordinate system of the supracondylar region (see FIG. 17A. By tilting the radius/ulna support carriage 28 relative to the stationary humeral support carriage 26, a rotational force vector (torque) is applied about the Mechanical Horizontal Axis to the fractured end of the distal bone region (held in the radius/ulna support carriage 28). The flexion/extension rotation force, mechanically applied by the flexion/extension rotation mechanical force reduction assembly 40, pivots the fractured end of the distal bone region toward the fractured end of the proximal bone region. Flexion/extension rotation returns the fractured ends of the proximal and distal bone regions that have been separated due to the fracture back toward the native state of alignment.

b. Mechanically Adjusting and Maintaining Flexion/Extension Rotation

In the exemplary embodiment (see FIG. 19B), flexion/extension achieved by tilting the radius/ulna support carriage 28 is controlled by a flexion/extension control mechanism 100 on the Right Side of the fracture reduction assembly 40.

In the exemplary embodiment, the flexion/extension control mechanism 100 includes a threaded locking pin 102 that can be advanced by rotation into the vertical short bar 96B and Bottom-most cross bar 96C of the first linkage section 96 of the flexion/extension mechanical force reduction assembly 40. A control knob 104 on the exposed end of the locking pin 102 allows the caregiver or surgeon to rotate the locking pin 102 clockwise or counterclockwise.

By rotating the locking pin 102 clockwise, the locking pin 102 causes the vertical short bar 96B and the Bottom-most cross bar 96C to frictionally interfere. The frictional interference prevents tilting articulation of the first and second parallelograms 96 and 98 of the flexion/extension mechanical force reduction assembly 40.

Conversely, by rotating the locking pin 102 counterclockwise, frictional interference between the vertical short bar 96B and the Bottom-most cross bar 96C is freed. The absence of frictional interference allows the caregiver or surgeon to tilt the first and second parallelograms 96 and 98 to achieve a desired amount of flexion/extension rotation, by applying force to the Free Side of the second parallelogram 98, e.g., by holding the vertical traction carriage 54 and applying force toward the Free Side or Support Side, as desired. This can be seen in FIG. 25C. When the desired amount of flexion/extension is achieved, the caregiver or surgeon can rotate the locking pin 102 clockwise, to maintain the desired flexion/extension. The frictional interference maintains the then-present tilted, torque-applying position of the radius/ulna support carriage 28, to maintain the then-present degree of flexion/extension rotation.

In the exemplary embodiment, the pace of flexion/extension rotation is incrementally controlled by manual force applied by the caregiver or surgeon (see FIG. 76) in a macro-condition. In the exemplary embodiment, there is no micro-condition of flexion/extension rotation, as reducing in this plane typically does not require micro-incremental alignment.

As will be exemplified in greater detail later, the flexion/extension rotation mechanical force reduction assembly 40 applies mechanical force reduction to achieve flexion/extension rotational alignment, which can be maintained by the flexion/extension control mechanism, while other, different mechanical reduction forces are applied by the system.

V. Systems and Devices for Mechanically Fixing a Bone Fracture Following Reduction A. Overview Illustrative devices and systems 10 for achieving a mechanical force reduction of a fracture have been described, for the purpose of illustration, in the context of reducing a supracondylar fracture. The devices and systems 10 mechanically reduce the fracture by the application of one or more mechanical force vectors to return bone regions separated and displaced by the fracture back toward a native state of alignment, i.e., that which existed prior to the fracture.

Next to be described are illustrative devices and systems 200 for mechanically "fixing" the fracture following its reduction. As used herein, the terms "mechanical" and "mechanism" broadly connote the presence of one or more tools or instruments that guide the insertion of a bone fixing device. In this respect, the terms "mechanical" and "mechanism" as used herein apply not only to the use of "machines" in the traditional sense (e.g., with components such as axles, bearings, gears, linkages, springs, wheels, pulleys, motors, engines, compressors, pumps, pistons, and the like, interacting alone or in combination to generate and apply kinetic force), but also to any tool or instrument that guides the insertion of a bone fixing device using, e.g., electrical and/or electro-mechanical components, and/or pneumatic components, and/or hydraulic components, and/or electronic components, and/or mechatronic components, and/or nanotechnology components, and can also incorporate, e.g., robotics, automation, and/or computer control.

The systems 200 mechanically "fix" a reduction by providing one or more bone fixing instruments or tools into the region of the reduced bone fracture. The bone fixing instruments or tools provide systematic mechanical guidance for the placement of bone fixing devices 202 such as pins or rods (see, e.g., FIG. 31B), which secure the bone regions together in the desired anatomic orientations achieved by reduction. The bone fixing devices 202 stabilize the anatomic orientations of the reduction, thereby preventing the reduced bone regions from moving out of reduction alignment as healing occurs.

The systems 200 and the mechanical instruments or tools and methods they incorporate for fixing a fracture reduction, as will be described, are applicable to all bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condylar fracture), e.g. at, in, or near the elbow, or at, in, or near the knee. Still, as before explained, the technical features of the systems 200 can be well exemplified and highlighted with respect to the fixing of supracondylar fractures of the elbow. For this reason, the systems 200 and the instruments, tools, systems, and methods they incorporate will be described in this context. Nevertheless, it is to be appreciated that the systems 200 are not restricted to supracondylar applications. It is to be appreciated that the disclosed instruments, the systems 200 and the devices, instruments, and methods they incorporate are readily applicable for use in treating all types of bone fractures, simple or complex, of any bone type, in children or adults, anywhere in the body.

In the illustrative embodiments, the systems 200 for mechanically fixing the reduced bone fracture are shown in association with the systems 10 for mechanically reducing the bone fracture in the first instance. For example, FIGS. 29, 30, 31A, 31B, and 32 show a bone fixing system 200 in association with the mechanical fracture reduction fixture 14 or s representative system 10.

The integration of devices and systems for mechanically reducing and fixing a bone fracture is desirable, but not essential. The systems and devices for mechanically reducing a bone fracture in the first instance, and then fixing the reduced bone fracture in the second instance can comprise separate, free-standing units, or, as will be shown, integrated into assemblies having complementing, dual functionality.

Figure 46A:
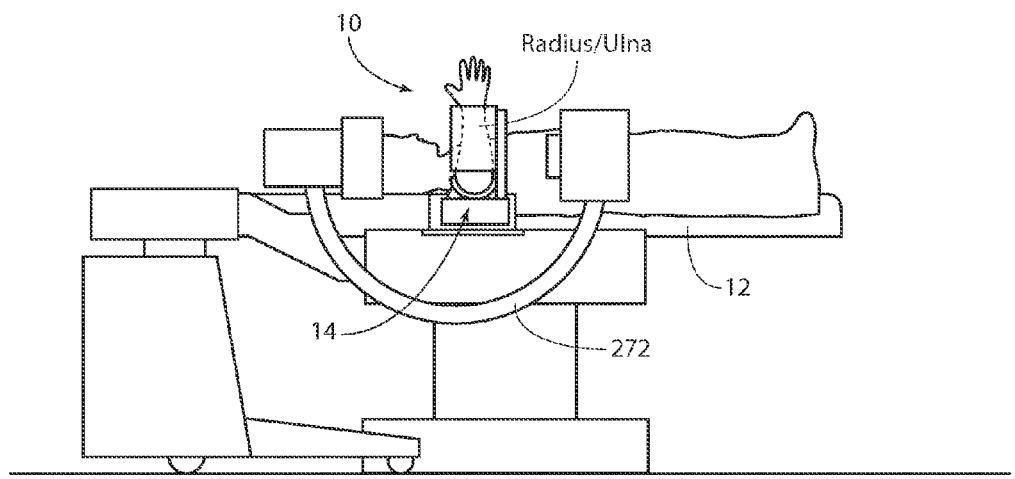
FIG. 46A is a side elevation view of the system shown in FIGS. 18A and 18B, with an individual having a supracondylar fracture of a right arm laying in a prone position on the patient support platform, and the mechanical bone reduction fixture supporting the humerus and forearm of the individual in a manner conducive for reducing the supracondylar fracture of the right arm, in association to a c-arm oriented to provide a lateral radiographic image of the fracture.

In use, both bone reduction and bone reduction fixing are desirably performed using conventional radiation imaging techniques. This is illustrated in FIGS. 46A/B and FIGS. 47A/B. FIG. 46A shows an individual having a supracondylar fracture lying in a supine position for treatment. For treatment of a supracondylar fracture, as has been previously described, the humerus of the individual is laterally extended from the shoulder and the radius/ulna is flexed at the elbow to point the hand in a superior direction facing the shoulder. The orientation of the individual's humerus and radius/ulna can be maintained, e.g., by the humeral support carriage 26 and the radius/ulna support carriage 28 of the mechanical fracture reduction fixture 14, as has been and will be described in greater detail later.

Figure 46B:
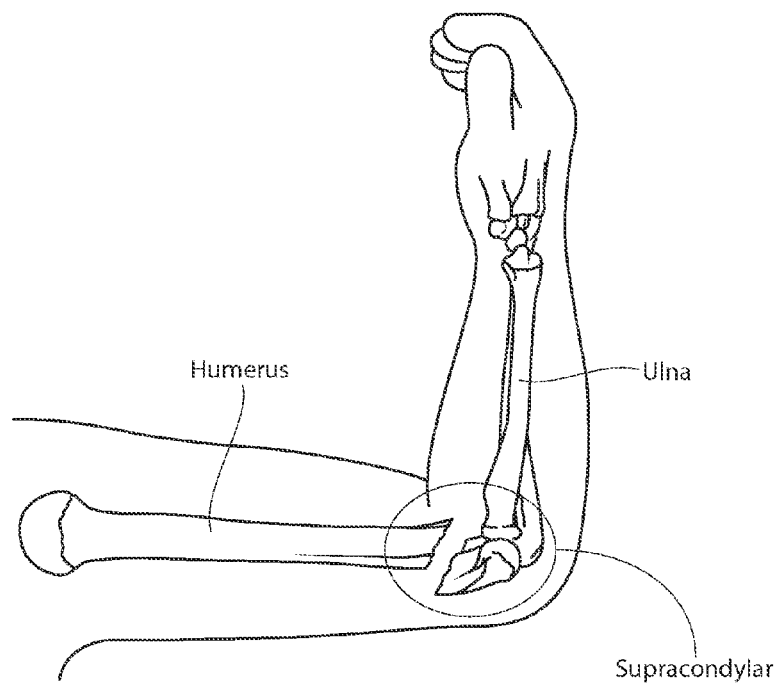
FIG. 46B is an illustration of a lateral radiographic image of the supracondylar fracture taken by the c-arm oriented in the manner shown in FIG. 46A.
Figure 47A:
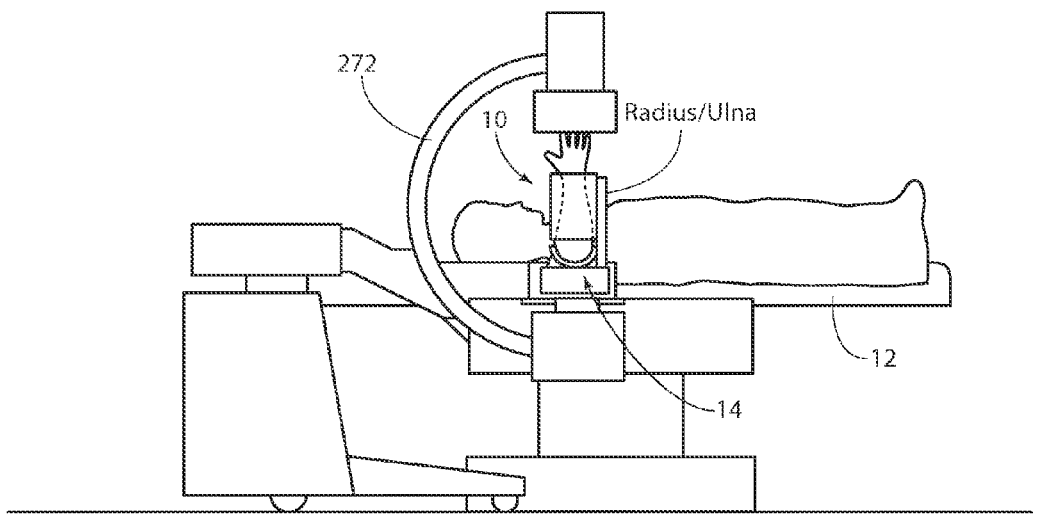
FIG. 47A is a side elevation view of the system shown in FIGS. 18A and 18B, with an individual having a supracondylar fracture of a right arm laying in a prone position on the patient support platform, and the mechanical bone reduction fixture supporting the humerus and forearm of the individual in a manner conducive for reducing the supracondylar fracture of the right arm, in association a c-arm oriented to provide an a-p radiographic image of the fracture.
Figure 47B:
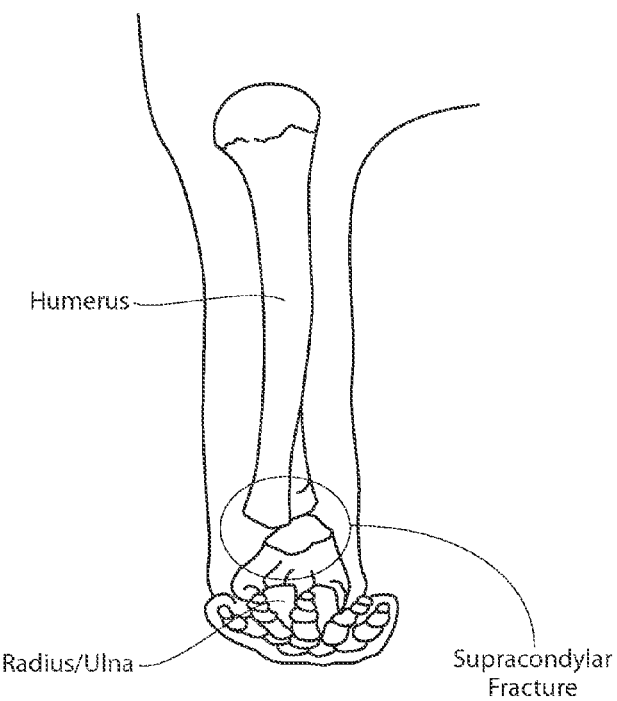
FIG. 47B is an illustration of an a-p radiographic image of the supracondylar fracture taken by the c-arm oriented in the manner shown in FIG. 47A.

Conventional radiation imaging techniques include a c-arm 272 that applies radiation through the fracture region to create a viewable radiographic image of the orientation of the bone structures. The c-arm 272 can be oriented relative to the fracture region in a horizontal plane (as shown in FIG. 46A), to provide a lateral view of the fracture region, which is shown in FIG. 46B. The c-arm 272 can also be swung into a generally vertical plane with respect to the fracture region (as shown in FIG. 47A) to provide an anterior-to-posterior (a-p) view of the fracture region, which is shown in FIG. 47B. The use of the radiographic lateral and a-p views during mechanical force reduction will be further described in greater detail later. First, there will be a description of the structural form and function of representative devices and systems for mechanically "fixing" the fracture following its reduction, which also relies upon use of the radiographic lateral and a-p views just described.

B. Pin Guide Assembly

As has been described, a system 200 is provided for fixing a reduced bone fracture. In a representative embodiment, the system 200 comprises a frame 204 that is sized and configured to support a reduced bone fracture of an individual. The system 200 also comprises a pin guide assembly 206 on the frame that includes a bone fixing device guide 208. The bone fixing device guide 208 defines a guide path along which a bone fixing device 202 can be advanced into a region of the reduced bone fracture. The pin guide assembly 206 includes a linkage system 212 that couples the bone fixing device guide 208 to the frame 14 for articulation of the guide path among a plurality of desired orientations with respect to the reduced bone fracture.

FIGS. 27 to 35 show an exemplary structural embodiment of a pin guide assembly 206 for fixing a fracture following its reduction. The pin guide assembly 206 establishes and maintains, by mechanical means, a desired path for advancement of a bone fixing device 202—independently in different planes—prior to advancement of the bone fixing device 202, e.g. pin, into a reduced bone fracture. The technical features and benefits of the pin guide assembly 206 will be described for the purpose of illustration in the context of fixing a reduced supracondylar fracture, but the technical features that will be described are applicable to fixing reduced bone fractures, simple or complex, of all bone types, in children or adults.

Figure 27:
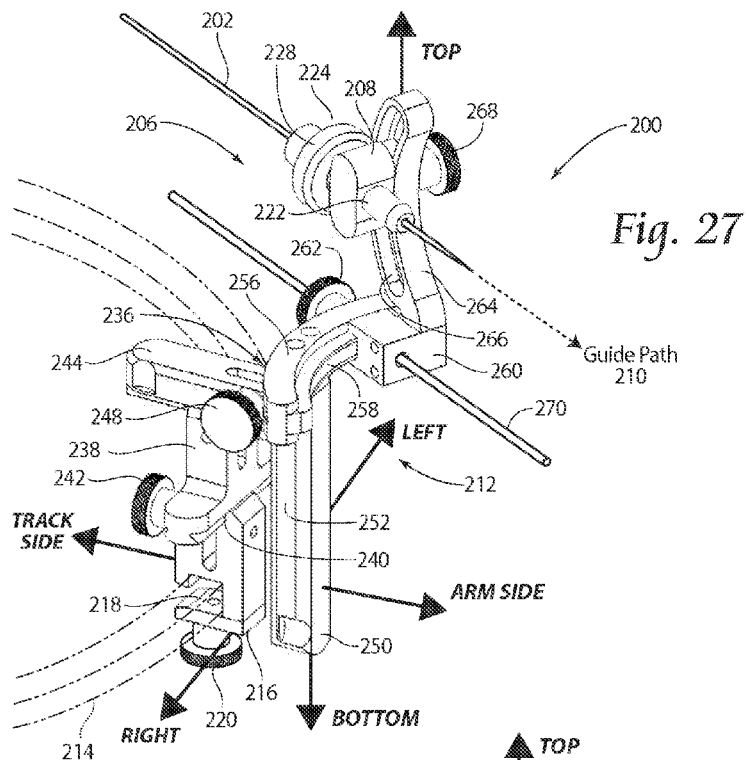
FIGS. 27 and 28 are, respectively, Right Side and Left Side perspective elevation views of an exemplary pin guide assembly for mechanically fixing a supracondylar fracture following reduction.
Figure 28:
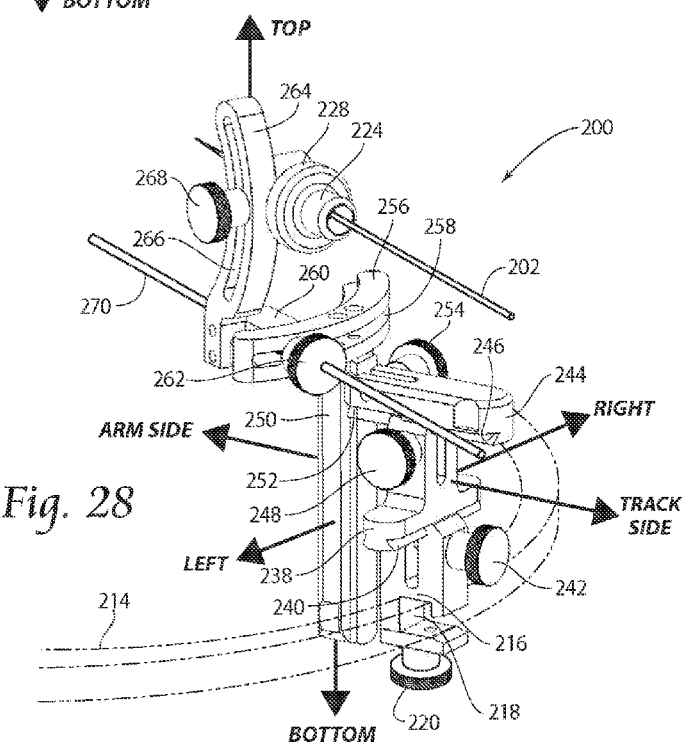
Figure 29:
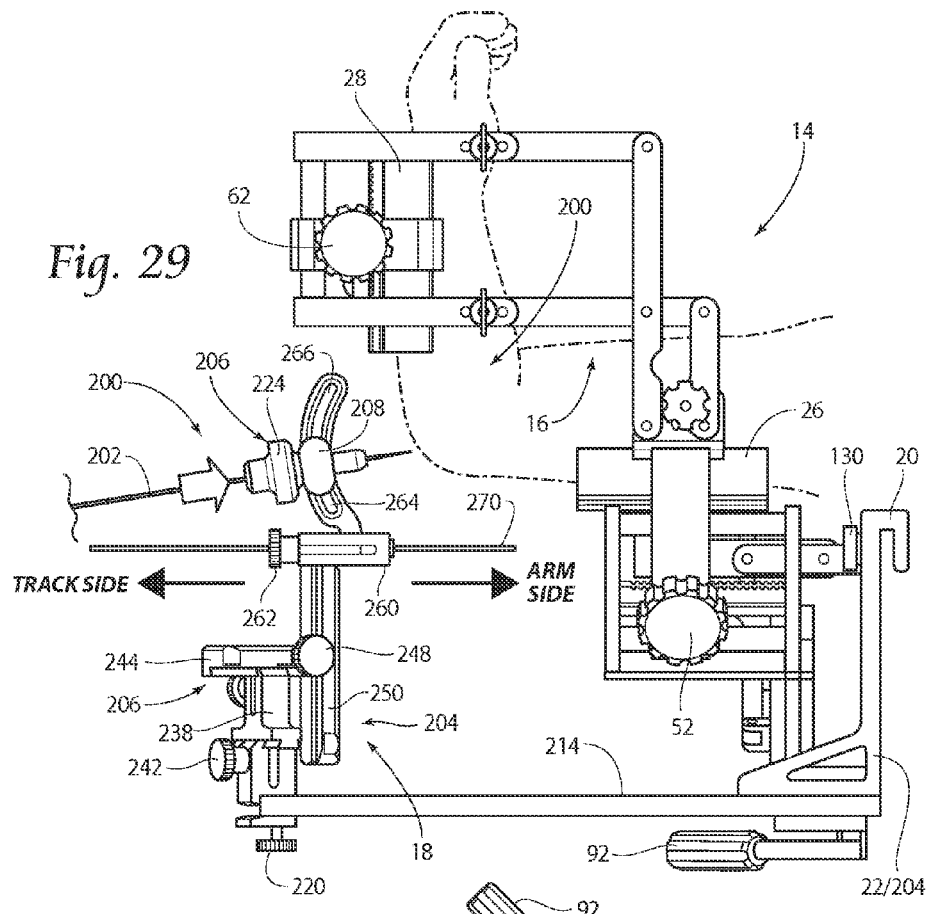
FIGS. 29 and 30A are, respectively, a Right Side elevation view and a Top view of the pin guide assembly shown in FIGS. 27 and 28 mounted for use an alignment rail in association with a mechanical bone reduction fixture as shown in FIGS. 19A to 19F, for mechanically orienting and guiding a bone fixing device for fixing a supracondylar fracture following reduction.

FIGS. 27 and 28 show the pin guide assembly 206 prior to its association with a fractured bone region. FIGS. 29 to 31A and 32 show the pin guide assembly 206 in association with a fracture reduction fixture 14 of the type previously described. In the exemplary embodiment, the fracture reduction fixture 14 includes a circular fixing alignment rail 214, on which the pin guide assembly 206 is mounted for use.

FIGS. 27 to 31A have been annotated to provide baseline directional points of reference for the purpose of describing the exemplary embodiment of the pin guide assembly 206. The baseline directional points of reference are from the point of view of a caregiver or surgeon facing the Free Side of the fracture reduction fixture 14 after mounting of the pin guide assembly 206 on the mid-point of the circular fixing alignment rail.

From this perspective, the pin guide assembly 206 can be seen to have a Track (i.e., Rail) Side, which, in use, faces in the direction of the circular fixing alignment rail on the Free Side of the fracture reduction fixture 14, and an Arm Side, which, in use, faces in the opposite direction toward the fractured arm held by the fracture reduction fixture 14. From this perspective, the baseline direction points of reference also include a Left Side, a Right Side, a Top, and a Bottom, relative to the view of the surgeon or caregiver facing the circular fixing alignment rail 214 on the Free Side of the fracture reduction fixture 14.

As was the case for the fracture reduction fixture 14, the orientation of the Left and Right Sides of the pin guide assembly 206 relative to the head and feet of the patient when in use will vary depending upon whether the supracondylar fracture is in the patient's the right arm or in the patient's left arm. For a right arm fracture, the Left Side of the pin guide assembly 206 faces the patient's head. For a left arm fracture, the Right Side of the pin guide assembly 206 faces the patient's head. FIGS. 29 to 31A are based upon a right arm fracture.

1. The Shuttle Body

The pin guide assembly 206 includes at its Bottom-most a shuttle body 216 (see also FIG. 32). The shuttle body 216 is sized and configured to be adjustably located relative to a bone region having a fracture that has been reduced. The shuttle body 216 includes a shuttle mount 218 that is sized and configured to slide or travel along the circular fixing alignment rail 214 provided on the fracture reduction fixture 14. The shuttle mount 218 of the shuttle body 216 permits the shuttle body 216 to be manually positioned at an infinite number of positions from Left Side to Right Side along the fixing alignment rail 214. As will be discussed later, the fixing alignment rail 214 assists in proper radiograph alignment when carrying out the described procedures.

A shuttle locking screw 220 can be tightened by rotation in one direction to establish frictional interference between the shuttle mount 218 and fixing alignment rail 214, thereby preventing travel along the fixing alignment rail 214 and preserving the then-established position of the shuttle body 216. The shuttle locking screw 220 can be loosened by rotation in an opposite direction to remove frictional interference between the shuttle mount 218 and the fixing alignment rail 214, thereby allowing free travel of the shuttle body 216 along the fixing alignment rail 214 for repositioning.

2. The Bone Fixing Device Guide

The pin guide assembly 206 includes at its Top-most the bone fixing device guide 208. The pin guide assembly 206 shown in FIGS. 27, 28, and 32 includes a guide channel 222 (see FIG. 35). The guide channel 222 defines a path along which a conventional bone fixing device 202 can be manually advanced through the pin guide assembly 206 by a caregiver or surgeon.

The bone fixing device 202 comprises a thin rod (or pin) having a sharpened leading tip for penetrating skin and bone during advancement. The bone fixing device 202 includes a radio-opaque material, so that the orientation of the bone fixation device relative to the reduced bone structures can be concurrently viewed by radiation imaging.

(i) Sterile Guide Bushing

In a representative embodiment, the system 200 comprises a guide bushing 224 that includes a bushing channel 226 for passing a bone fixing device 202. As will be described in greater detail later, the guide bushing 224 is sized and configured to be handled separate from the guide assembly for insertion into the guide channel 222 of the bone fixing device guide 208 at the instance of use and for separation from the guide path after use. In this arrangement, the system includes packaging that maintains the guide bushing 224 in a sterile condition prior to insertion into the guide path.

In the exemplary embodiment (see FIGS. 33A to 35), the bone fixing device guide 208 is sized and configured to receive during use the guide bushing 224 as a sterile, single use, disposable item. The guide bushing 224 is elongated to be inserted into the guide channel 222 of the bone fixing device guide 208 (see FIG. 35) at the instance of use. The guide bushing 224 also includes a collar 228 that allows the guide bushing 224 to be grasped at its periphery, away from the bushing channel 226, and also serves as a stop to limit the length of insertion of the guide bushing 224 through the guide channel 222.

The bushing channel 226 of the guide bushing 224 includes an entrance end 230 (see FIG. 33A) for receiving the bone fixing device 202 for passage. The entrance end 230 desirably comprising a funnel shaped entrance surface 232 that directs the bone fixing device 202 directly into the bushing channel 226. In this arrangement, the funnel shaped entrance surface 232 shields the bushing channel 226 from inadvertent contact and loss of sterility prior to use, e.g. by a caregiver or surgeon or a person setting up the pin guide assembly 206.

As FIG. 34 shows, the guide bushing 224 is intended to be supplied to the caregiver or surgeon separate from the pin guide assembly 206 in a sterilized condition within a sealed, sterile pouch or packaging 234. The caregiver or surgeon removes the guide bushing 224 from the packaging 234 when desired and mounts it in the guide channel 222 of the bone fixing device guide 208 as a sterile component. Its insertion can be delayed during set-up and pre-insertion manipulation of the pin guide assembly 206, up to the particular moment that insertion of the bone fixing device 202 is desired.

The guide bushing 224 can thereby remain in a sterile condition within the sterile pouch or packaging 234 right up to the instance of use. During use, the bone fixing device 202 comes into contact only with the inward facing tapered surface 232 (funnel) of the guide bushing 224, which protects the sterility of the bushing channel 226 and minimizes the chance that the bone fixing device 202 will contact a non-sterile environment prior to its inserting into the fracture site. After use, the guide bushing 224 can be removed from the pin guide assembly 206 and, if desired, disposed of. Alternatively, the guide bushing 224 can be re-sterilized and packaged again in a sterile condition for reuse in a later procedure.

The modular, sterile, and desirably single use guide bushing 224 makes possible the sterile insertion of a bone fixing device 202 using the pin guide assembly 206, without the need to sterilize the entire pin guide assembly 206. During use, the bone fixing device 202 need only contact the protected sterile receiving end 230 of the guide bushing 224. Sterilization requirements are thereby limited to the guide bushing 224, and not the overall pin guide assembly 206. After use, the guide bushing 224 can be removed from the pin guide assembly 206 and, as desired, disposed of or re-sterilized.

3. The Orientation Linkage System

Referring mostly to FIG. 32, the shuttle body 216, riding on the shuttle mount 218, is coupled to the bone fixing device guide 208 by a stacked array of additional mounts or links comprising a bone fixing linkage system 236. In a representative embodiment, the bone fixing linkage system 236 includes a first linkage that articulates the bone fixing device guide 208 in a first plane, and includes a mechanism that is sized and configured to mechanically interact with the first linkage to maintain a desired articulation in the first plane. The bone fixing linkage system 236 also desirably includes a second linkage that articulates the bone fixing device guide 208 in a second plane different than the first plane, and includes a mechanism that is sized and configured to mechanically interact with the second linkage to maintain a desired articulation in the second plane, without altering the desired articulation in the first plane. The bone fixing linkage system 236 can also include at least one additional linkage that articulate the bone fixing device guide 208 in a third plane that intersects one of the first and second planes at an angle, and includes a mechanism that is sized and configured to mechanically interact with the additional linkage to maintain a desired articulation in the third plane, without altering the desired articulations in the first and second planes.

The independent linkages of the of bone fixing linkage system 236 allows independent orientation of the bone fixing device guide 208 relative to the reduced fracture in different planes, including a horizontal plane (i.e., generally along the Mechanical Horizontal or Perpendicular Axes of the associated fracture reduction fixture 14), a vertical plane (i.e., generally along the Mechanical Vertical Axis of the associated fracture reduction fixture 14), and one or more planes that intersect a horizontal or vertical plane at an angle (which can also be called an "angular plane"). Within each plane, the bone fixing linkage system 236 allows the surgeon or caregiver or surgeon to hold stationary a desired orientation in one plane, and to proceed with orientation in another plane without altering any preceding orientation.

(i) Left and Right Translation Within the Horizontal Plane

In a representative structural implementation, the bone fixing linkage system 236 comprises a first link bar or mount 238. The first link bar 238 is coupled to the shuttle body 216 within a first channel 240 that extends parallel to the fixing alignment rail 214 in a Right-ward and Left-ward direction in the orientation shown in FIG. 32. The first channel guides lateral movement (i.e., translation) of the first link bar 238 relative to the mount in a Right-ward and Left-ward direction within the horizontal plane. The bone fixing linkage system 236 transmits this track of lateral movement or translation to the bone fixing device guide 208. The first channel 240 permits the first link bar 238 to be manually positioned at an infinite number of positions along the first channel 240. Frictional engagement between the first channel 240 and first link bar 238 can be established (e.g., by a set screw 242) that holds stationary the then-established position of the first link bar 238 within the first channel 240. Release of the frictional engagement allows repositioning by the further application of a translational force by the caregiver or surgeon.

(ii) Track Side and Arm Side Translation Within the Horizontal Plane

The bone fixing linkage system further comprises a second link bar or mount 244. The second link bar 244 is coupled to the first mount 218 within a second channel 246 in the first link bar 238 that extends perpendicular to the first channel 240 in a Track Side and Arm Side direction in the orientation shown in FIG. 32. The second channel 246 guides linear movement (i.e., translation) of the second link bar 244 relative to the mount in a Track Side and Arm Side direction within the horizontal plane. The bone fixing linkage system 236 transmits this track of linear movement to the bone fixing device guide 208. The second channel 246 permits the second link bar 244 to be manually positioned at an infinite number of positions along the second channel 246. Frictional engagement between the second channel 246 and the second link bar 244 can be established (e.g., by a set screw 248) that holds stationary the then-established position of the second link bar 244 within the second channel 246. Release of the frictional engagement allows repositioning by the further application of a translational force by the caregiver or surgeon.

If desired, the second link bar or mount 244 can be rigidly attached to the first link bar or mount 238, i.e., without accommodating Track Side and Arm Side translation. This is because the bone fixing device 202 itself can be translated in a Track Side to Arm Side direction for alignment purposes.

(iii) Top-Ward and Bottom-Ward Translation Within the Vertical Plane

The bone fixing linkage system 236 further comprises a third link bar or mount 250 that is coupled to the second link bar 244 within a third channel 252 in the second link bar 244 that extends perpendicular to the second channel 246 in a Top-ward and Bottom-ward direction in the orientation shown in FIG. 32. The third channel 252 guides linear movement (i.e., translation) of the third link bar 250 relative to the mount in a Top-ward and Bottom-ward direction within the vertical plane. The bone fixing linkage system 236 transmits this track of linear movement to the bone fixing device guide 208. The third channel 252 permits the third link bar 250 to be manually positioned at an infinite number of positions along the third channel 252. Frictional engagement between the third channel 252 and third link bar 250 can be established (e.g., by a set screw 254) that holds stationary the then-established position of the third link bar 250 within the third channel 252. Release of the frictional engagement allows repositioning by the further application of a translational force by the caregiver or surgeon.

(iv) Left-Ward and Right-Ward Rotation Within the Horizontal Plane

The bone fixing linkage system 236 further comprises a fourth link bar or mount 256. The fourth link bar 256 is rigidly coupled to the Top of the third link bar 250. The fourth link bar 256 secured to the Top of the third link bar 250 in a Right-ward and Left-ward orientation, as shown in FIG. 32. The fourth link bar 256 is curvilinear, having a curvature from Left to Right, in the orientation shown in FIG. 32, which generally coincides with the curvature of the fixing alignment rail 214. The curvilinear axis of the fourth link bar 256 also extends parallel to the linear axis of the first link bar 238. The fourth link bar 256 includes an elongated horizontal through slot 258, which extends in a curvilinear Free-ward and Left-ward direction in the orientation shown in FIG. 32. A follower 260 rides in the slot 258 in a curvilinear Right-ward and Left-ward direction in the orientation shown in FIG. 32. The slot 258 guides curvilinear movement (i.e., rotational) of the follower 260 along the fourth link bar 256 in a curved Right-ward and Left-ward trajectory within the horizontal plane. The bone fixing linkage system 236 transmits this track of rotational movement to the bone fixing device guide 208. The slot 258 permits the follower 260 to be manually positioned, within the horizontal confines of the slot 258, at an infinite number of positions along this trajectory. A follower locking screw 262 can be tightened by rotation in one direction to establish frictional interference between the slot 258 and the follower 260, thereby preventing travel along the slot 258 and preserving the then-established position of the follower 260. The follower locking screw 262 can be loosened by rotation in an opposite direction to remove frictional interference between the slot 258 and the follower 260, thereby allowing free travel of the follower 260 trajectory for repositioning the bone fixing device guide 208.

(v) Top-Ward and Bottom-Ward Rotation Within the Vertical Plane

The bone fixing linkage system 236 further comprises a fifth link bar or mount 264. The fifth link bar 264 is rigidly coupled to the Arm Side of the follower 260, extending in a Top-ward direction, in the orientation shown in FIG. 32. The fifth link bar 264 is curvilinear, having a curvature from Bottom to Top which generally matches the curvature of the fourth link bar 256 from Right to Left. The fifth link bar 264 includes an elongated vertical slot 266, which extends in a curvilinear Top-ward direction in the orientation shown in FIG. 32. The bone fixing device guide 208 rides in the slot 266 in a curvilinear Top-ward direction in the orientation shown in FIG. 32. The slot 266 guides curvilinear movement (i.e., rotational) of the bone fixing device guide 208 along the fifth link bar 264 in a Top-ward trajectory within the vertical plane. The Top-ward trajectory orients the guide channel 222 of the bone fixing device guide 208 along planes that intersect the horizontal or vertical plane at an angle (i.e., angular planes). The Top-ward trajectory (beginning that the Bottom of the slot 266 and moving to the Top of the slot 266) will orient the guide channel 222 of the bone fixing device guide 208 along angular planes that direct the bone fixing device 202 Top-ward, then horizontal, and then Bottom-ward. The slot 266 permits the bone fixing device guide 208 to be manually positioned, within the vertical confines of the slot 266, at an infinite number of positions along this trajectory. A guide locking screw 268 can be tightened by rotation in one direction to establish frictional interference between the slot 266 and the bone fixing device guide 208, thereby preventing travel along the slot 266 and preserving the then-established position of the bone fixing device guide 208. The guide locking screw 268 can be loosened by rotation in an opposite direction to remove frictional interference between the slot 266 and the bone fixing device guide 208, thereby allowing free travel of the bone fixing device guide 208 along the trajectory for repositioning the guide 208.

As FIG. 32 shows, the vertical distance (Top-ward and Bottom-ward) between the bone fixing device guide 208 and the shuttle body 216 (and the fixing alignment rail 214 itself) can be manually adjusted in both vertical translational and vertical rotational tracks. By moving the third link bar 250 Top-ward and Bottom-Ward, vertical translation can be achieved and maintained. By moving the bone fixing device guide 208 along the slot 266 within the fifth link bar 264 in a Top-ward direction, a vertical rotation (trajectory) can be achieved and maintained.

As FIG. 32 also shows, the horizontal distance (Track-ward and Arm-ward) between the bone fixing device guide 208 and the shuttle body 216 (and the fixing alignment rail 214 itself) can be manually adjusted in a horizontal translational track. By moving the second link bar 244 Track-ward and Arm-Ward, horizontal translation can be achieved and maintained.

As FIG. 32 also shows, the horizontal offset (lateral) distance (Right-ward and Left-ward) between the bone fixing device guide 208 and the shuttle body 216 (and the fixing alignment rail 214 itself) can be manually adjusted in both lateral translational and lateral rotational tracks. By moving the first link bar 238 Right-ward and Left-ward, lateral translation can be achieved and maintained. By moving the shuttle body 216 along the fixing alignment rail 214, a macro-degree of lateral rotation (trajectory) can be achieved and maintained. By moving the follower 260 along the slot 258 within the fourth link bar 256, a micro-degree of horizontal rotation (trajectory), finer than the macro-degree, can also be achieved and maintained.

(vi) A-P Guide Pin

The follower 260 of the fourth link bar 256 also accommodates an a-p guide pin 270 positioned in a stationary position vertically below the bone fixing device guide 208 (i.e., vertically Bottom-ward of the guide 208, through which the bone fixing device 202 is advanced) (see FIGS. 27, 28, 29, and 32). In this exemplary embodiment, the a-p guide pin 270 is also positioned outside the body region vertically above the shuttle body 216 (i.e., vertically Top-ward of the shuttle body 216). The a-p guide pin 270 includes a radio-opaque material, so that the orientation of the a-p guide pin 270 can be visualized by radiographic imaging (see FIGS. 30A and 30B). The a-p guide pin 270 extends along a horizontal axis that is parallel to and axially aligned with (i.e., in the same vertical plane as) the axis of the path along which the bone fixing device 202 is manually advanced by a caregiver or surgeon.

Figure 30A:
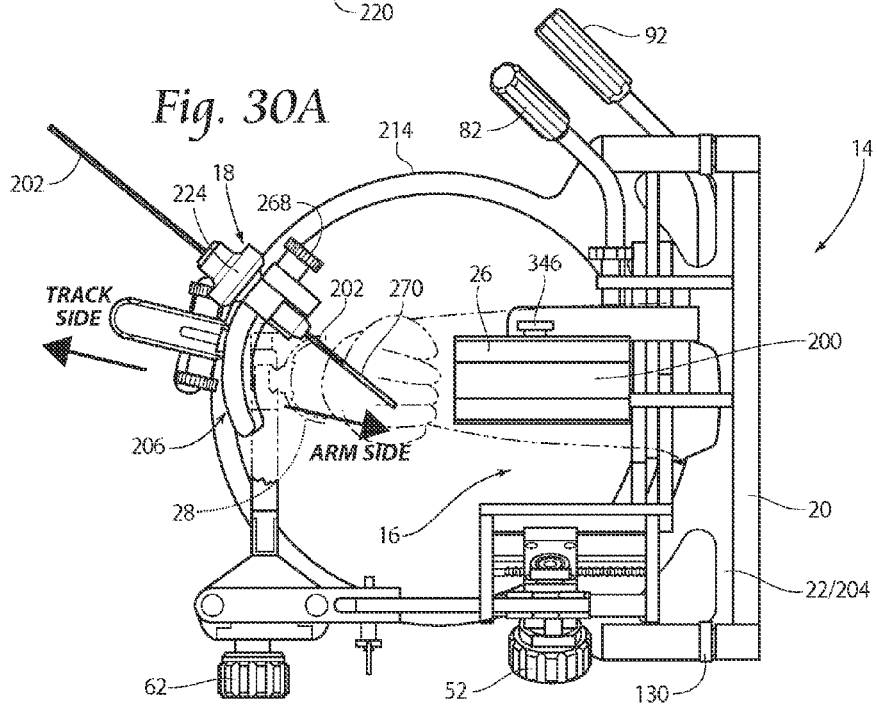

Due to this purposeful alignment, when the c-arm 272 is oriented in a vertical plane (shown in FIGS. 30A and 30B), the radiographic a-p view will include the image of the a-p guide pin 270 (see FIGS. 30A and 30B). As the bone fixing device 202 is manually advanced by a caregiver or surgeon into the view, the image of the bone fixing device 202 will coincide with the image of the a-p guide pin 270, as FIG. 30B shows. Translational and rotational adjustment of the guide pin 270 establishes a desired path of placement for the bone fixing device 202, prior to actual insertion of the bone fixing device 202, aided by a-p radiographic monitoring of the position of a-p guide pin 270.

VI. The Orthotic Brace

Figure 36:
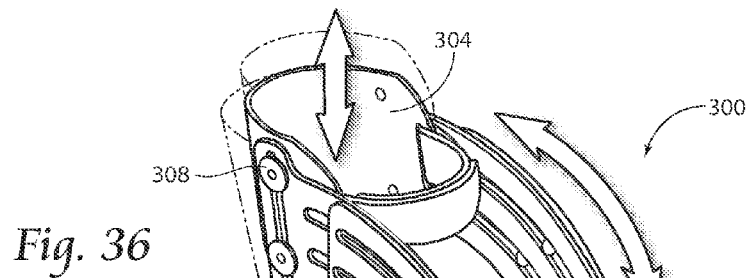
FIG. 36 is a perspective view of an exemplary orthotic brace that can be assembled to stabilize a fixed bone reduction for healing.

FIG. 36 shows an exemplary embodiment of an orthotic brace 300, which is sized and configured to be fully or partially assembled and fitted to a region or regions of a bone fracture prior to, during, or after fracture reduction and/or fixing. The orthotic brace 300 helps to maintain and/or improve the reduction, after fixing, while healing occurs. The orthotic brace 300 performs this function by controlling, guiding, limiting and/or immobilizing the reduction after fixing; and/or restricting movement in a given direction; and/or reducing weight bearing forces; and/or otherwise maintain the orientation of the bone structures after reduction and fixing.

The orthotic brace 300 can be made from various types of materials known in the orthotics field, e.g., plastic, elastic, metal, or a combination of similar materials.

The orthotic brace 300 can be sized and configured to be integrated into mechanical fracture reduction and fixing systems and methods, e.g., by accommodating temporary securing of the orthotic brace 300 to a humeral support carriage 26 and a radius/ulna support carriage 28 associated with a mechanical bone reduction fixture 14, either fully or partially assembled to the region of fractured bone, to thereby reside on the fixture 14 while mechanical reduction is achieved and/or reside on the fixture 14 while mechanical reduction fixing is achieved. After reduction and fixing, the orthotic brace 300 is sized and configured to be removed from the system, to be thereafter worn by the individual, fully assembled to the fixed reduction, to maintain and/or improve the fixed reduction while healing occurs.

The orthotic brace 300 and associated systems and methods that will be described are applicable to all bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condular fracture), e.g. at, in, or near the elbow, or at, in, or near the knee. Still, as before explained in the context of previous descriptions, the technical features of the orthotic brace 300 and associated systems and methods can be well exemplified and highlighted with respect to the fixing of supracondylar fractures of the elbow. For this reason, the orthotic brace 300 and associated systems and methods will be described in this context. Nevertheless, it is to be appreciated that the orthotic brace 300 and associated systems and methods that embody features of the invention are not restricted to supracondylar applications. It is to be appreciated that the disclosed orthotic brace 300 and associated systems and methods are readily applicable for use in treating all types of bone fractures, simple or complex, of any bone type, in children or adults, anywhere in the body.

As shown in FIG. 36, the orthotic brace 300 is sized and configured for treating a supracondylar fracture. In this context, the orthotic brace 300 includes a humeral brace component 302 and a radius/ulnar brace component 304. In use, see FIG. 37, the humeral brace component 302 is secured to the humerus, e.g., by straps, to hold the humerus in a laterally extended position from the shoulder. The radius/ulnar brace component 304 is secured to the radius/ulna, e.g. by straps, to hold the radius/ulna while flexed at the elbow to point the hand in a superior direction facing the shoulder.

Struts 306 coupled to the humeral brace component 302 and the radius/ulna brace component 304 (see FIG. 36) allow relative movement of the humeral brace component 302 vertically, relative movement of the radius/ulnar brace component 304 horizontally, and relative flexure and extension of the humeral brace component 302 and the radius/ulnar brace component 304. Fasteners 308 on the struts 306 make it possible to lock the relative positions of the humeral brace component 302 and the radius/ulnar brace component 304 horizontally, vertically, and in flexure/extension to hold fast the reduction forces applied to the fracture.

Figure 37:
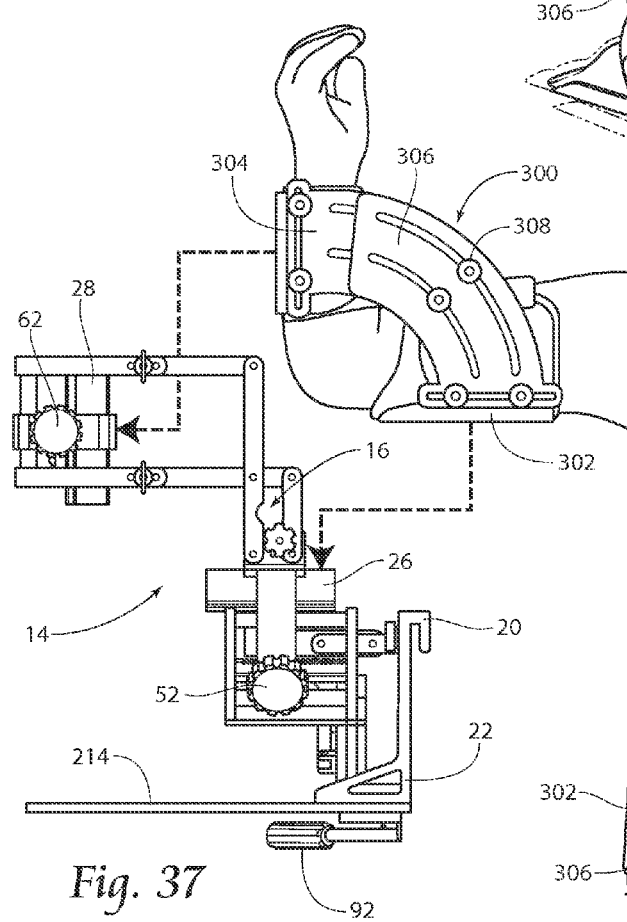
FIG. 37 is a side elevation view demonstrating the temporary fitment of the orthotic brace shown in FIG. 36 in association with a mechanical bone reduction fixture, like that shown in FIGS. 19A to 19F.

The exemplary fracture reduction fixture 14 previously described includes a humeral support carriage 26 and a radius/ulna support carriage 28, which can be sized and configured to carry the humeral brace component 302 and the radius/ulnar brace component 304. In this way, the fracture reduction fixture 14 and orthotic brace 300 work together to collectively hold the humerus and radius/ulna in the desired orientation during mechanical reduction, and to maintain this orientation during and after reduction, while the reduction is mechanical fixed. It can be appreciation that the form, fit, and function of the humeral brace component 302 and the radial/ulnar brace component 304 complement the form, fit, and function of the humeral support carriage 26 and the radius/ulna support carriage 28 of the mechanical fracture reduction fixture 14. For this reason, the orthotic brace 300 can be sized and configured to be partially or fully assembled to a region or regions of the fracture and be temporarily secured, e.g., by straps, pins, or fasteners, to the humeral support carriage 26 and the radius/ulna support carriage 28 of the reduction frame prior to mechanical force reduction (as FIG. 37 shows). The orthotic brace 300 can likewise be sized and configured, while partially or fully assembled to a region or regions of the fracture, to remain secured to the humeral support carriage 26 and the radius/ulna support carriage 28 during fixing of the reduced fracture. This technical feature will be described in further detail and shown in subsequent figures.

Figure 38:
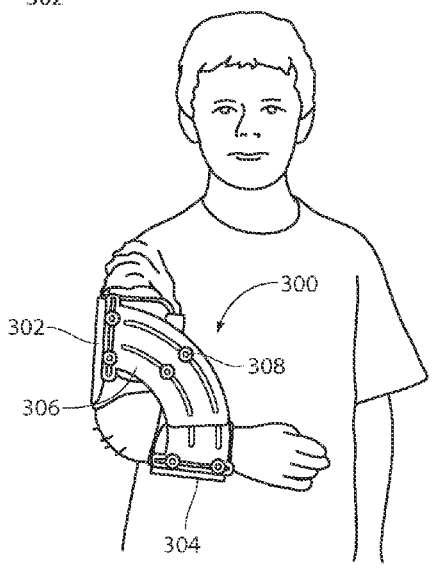
FIG. 38 is a perspective view of the orthotic brace shown in FIG. 36 being worn by an individual after the bone fracture has been mechanically reduced and fixed.
Figure 39:
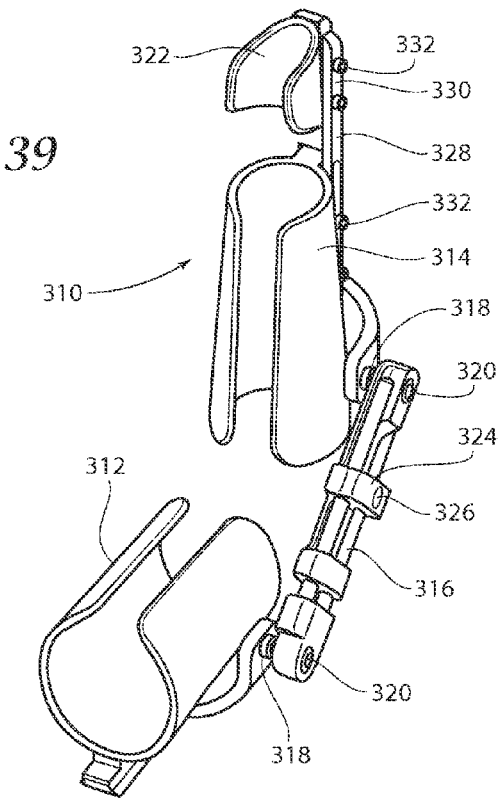
FIG. 39 is a perspective view of another exemplary orthotic brace that can be assembled to stabilize a fixed bone reduction for healing, the orthotic brace comprising a proximal brace component for assembly on a humeral region of s supracondylar fracture, a distal brace component for assembly on a radius/ulnar region of a supracondylar fracture, and an additional third brace component for assembly on wrist region distal to the radius/ulnar region of the supracondylar fracture.
Figure 40:
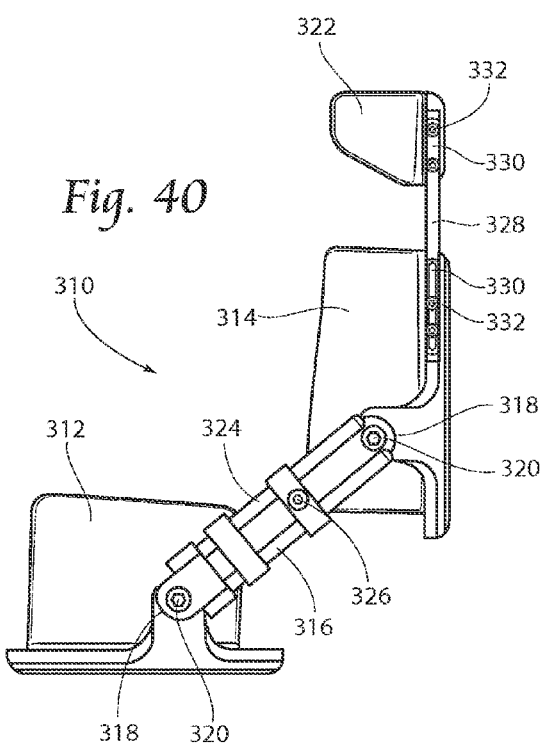
FIGS. 40 and 41 are side elevation views of the orthotic brace shown in FIG. 39, demonstrating the ability to adjust the spacing between the distal brace component and the third brace component.

After fixing of the mechanically reduced fracture, the orthotic brace 300 is released from the fracture reduction fixture 14 fully assembled to the individual's arm (see FIG. 38), to be worn by the individual to maintain and/or improve the reduction, after fixing, while healing occurs.

FIGS. 39 to 45B depict another (also referred to as being the "second") exemplary embodiment of an orthotic brace 310. In this exemplary embodiment, as will be described in greater detail later, the orthotic brace 310 includes a proximal brace component 312 that is sized and configured to be fitted to a proximal region of the fracture, and a distal brace component 314 that is sized and configured to be fitted to a distal region of the fracture.

The second orthotic brace 310 can be made from various types of materials known in the orthotics field, e.g., plastic, elastic, metal, or a combination of similar materials.

The second orthotic brace 310 may also be fitted with an expandable foam material, which can expand and contract once a fracture is reduced and fixed. The expandable foam material will allow the orthotic brace 310 to securely retain the fracture post-operation when swelling of the fracture region may occur.

The orthotic brace 310 in this exemplary embodiment also includes a strut 316 having a proximal region linked to the proximal brace component 312 and a distal region linked to the distal brace component 314. In this exemplary embodiment, at least one of the proximal and distal regions comprises a linkage mechanism 318 permitting articulation of the respective brace component 312/314 on the strut 316 within a range of rotational orientations to accommodate forces applied to reduce the fracture. These are generally shown by directional arrows in FIGS. 42A and 42B. The respective region further includes a locking mechanism 320 to maintain a desired rotational orientation within the range to maintain a desired reduction of the fracture.

In a desirable implementation (as shown in FIGS. 42A and 42B), both the proximal and distal regions comprise a linkage mechanism 318 permitting articulation of the respective brace component on the strut 316 within a range of rotational orientations in response to forces applied to reduce the fracture. In this arrangement, each proximal and distal region further includes a locking mechanism 320 to maintain a desired rotational orientation for each brace component within the range to maintain a desired reduction of the fracture.

The linkage mechanism 318 can comprise, e.g., a ball-and-socket joint, a hinge joint, a clevis joint, an axial joint, a universal joint, a spherical plain bearing, a multi-bar linkage, a spatial linkage, a spherical linkage, or a combination or combinations thereof. The linkage mechanism permits the respective brace component to be pivoted on the strut 316 (see FIG. 42A) as well as rocked and swung about the strut 316 (see FIG. 42B).

The second orthotic brace 310 can also include another brace component 322 interacting with at least one of the proximal and distal brace components 312/314.

The second orthotic brace 310 is sized and configured to be fully or partially assembled and fitted to a bone region having a fracture prior to, during, or after fracture reduction and fixing. The second orthotic brace 310 helps to maintain and/or improve the reduction, after fixing, while healing occurs. The second orthotic brace 310 performs this function by controlling, guiding, limiting and/or immobilizing the reduction after fixing; and/or restricting movement in a given direction; and/or reducing weight bearing forces; and/or otherwise maintain the orientation of the bone structures after reduction and fixing.

The second orthotic brace 310 and associated systems and methods that will be described are applicable to all bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condular fracture), e.g. at, in, or near the elbow, or at, in, or near the knee. Still, as before explained in the context of previous descriptions, the technical features of the orthotic brace 310 and associated systems and methods can be well exemplified and highlighted with respect to the fixing of supracondylar fractures of the elbow. For this reason, a structural implementation of the second orthotic brace 310 and associated systems, and methods will be described in this context. Nevertheless, it is to be appreciated that the orthotic brace 310 and associated systems and methods that embody features of the invention are not restricted to supracondylar applications. It is to be appreciated that the disclosed second orthotic brace 310 and associated systems and methods are readily applicable for use in treating all types of bone fractures, simple or complex, of any bone type, in children or adults, anywhere in the body.

In this context, the second orthotic brace 310 includes a proximal humeral brace component 312 and a distal radius/ulnar brace component 314. The humeral brace component 312 and the radius/ulnar brace 314 component are preferably formed of open cylindrical structures for receiving a region of the respective humerus and the radius/ulna, respectively. The use of straps and other devices to retain the fractured arm, as discussed above, could also be used with the second orthotic brace 310.

In the illustrated structural implementation (FIGS. 39 and 40), the strut 316 is connected by a ball-and-socket joint 318 to the humeral brace component 312 and by another, separate and independent ball-and-socket joint 312 to the radius/ulnar brace component 314. As FIGS. 42A, 42B, and 42C show, the separate and independent ball-and-socket joints 312 allow independent articulation of the humeral brace component 312 and/or the radius/ulnar brace component 314 within a range of rotational orientations to accommodate traction, translation, flexure/extension, pronation/supination, and varus/valgus rotational forces applied to reduce the fracture, as shown by the directional arrows in FIGS. 42A and 42B.

The humeral brace component 312 can be pivoted on its ball-and-socket joint 318 on the strut 316 within a range of rotational orientations (see FIG. 42A) and/or swung and/or rocked on its ball-and-socket joint 318 within a range of rotational orientations about the strut 316 (see FIG. 42B), including, within the ranges of articulation an infinite number of intermediate rotation orientations and combinations of rotational orientations.

Independent of the orientation of the humeral brace component 312, the radius/ulnar brace component 314 can likewise be freely pivoted on its ball-and-socket joint 318 on the strut 316 within a range of rotational orientations (see FIG. 42A) and/or swung and/or rocked on its ball-and-socket joint 318 within a range of rotational orientations about the strut 316 (see FIG. 42B), including, within the ranges of articulation an infinite number of intermediate rotation orientations and combinations of rotational orientations.

In the illustrated structural implementation (see FIG. 42C), a locking pin 320, e.g., with a hex bolt or allen wrench fitting, is operatively coupled to each ball-and-socket joint 318. Each locking pin 320 can be loosened, e.g., by counterclockwise rotation, to free articulation of the respective ball-and-socket joint 318. Conversely, each locking pin 320 can be tightened, e.g., by clockwise rotation, to frictionally prevent articulation of the respective ball-and-socket joint 318, and thereby maintain the desired angular orientation of the respective brace component 312/314, to allow for proper positioning of the second orthotic brace 310 on the reduced fracture.

Desirably, as is shown in the illustrated structural implementation (see FIG. 43), the strut 316 includes an axial mechanism 324 providing elongation or shortening of the axial distance between the proximal and distal brace components 312/314 independent of the linkage mechanism 318 just described, including a locking mechanism 326 to maintain a desired axial distance.

In the illustrated structural implementation, the axial mechanism 324 includes, e.g., telescoping strut arms. The telescoping strut arms 324 can be axially moved together or apart (as shown by directional arrows in FIG. 43, to mutually shorten or lengthen the separation between the humeral brace component 312 and the radius/ulnar brace component 314.

In the illustrated structural implementation, a locking pin 326, e.g., with a hex bolt or allen wrench fitting, is operatively coupled to the telescoping strut arms 324. The locking pin 326 can be loosened, e.g., by counterclockwise rotation, to allow the sliding of the strut arms 324 apart or together. Conversely, the locking pin 326 can be tightened, e.g., by clockwise rotation, to frictionally prevent the sliding and thereby maintain the desired separation between the brace components 312/314, to further allow for proper positioning of the second orthotic brace 310 on the reduced fracture.

Figure 41:
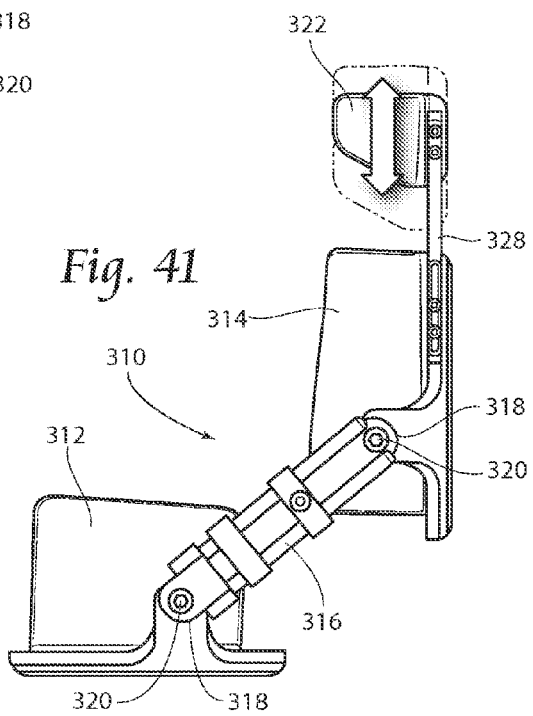

In the exemplary structural implementation for use on a supracondylar fracture (see also FIG. 41), the radius/ulnar component 314 further comprises a carpal brace component 322 coupled to the radius/ulnar brace component by a second strut 328. As FIG. 41 shows, the carpal brace component 322 is sized and configured to be fitted to a wrist region of the supracondylar fracture.

The second strut 328 establishes a spacing distance between the distal brace component 314 and the carpal brace component 322. The second strut 328 slides within a channels 330 in the distal brace component 314 and the additional brace component 322, which provides for elongation or shortening of the spacing distance.

A locking mechanism 332 is provided to maintain a desired spacing distance, to be properly sized to a particular individual. In the illustrated implementation, fasteners, e.g., screws or bolts, on the strut 328 can be loosened, e.g., by counterclockwise rotation, to allow the strut 328 to slide along the channels 330, thereby adjusting the separation between the carpal brace component 322 and the radius/ulnar brace component 314. The fasteners 332 can be tightened, e.g., by clockwise rotation, to frictionally prevent sliding of the strut 328 within the channels 330, to thereby to maintain a desired separation, once achieved.

As FIGS. 44A to 44C show, the second orthotic brace 310 can be sized and configured to be component part of a mechanical fracture reduction fixture 14, to accommodate temporary securing of the orthotic brace 310 to a humeral support carriage 26 and a radius/ulna support carriage 28, either fully or partially assembled to a region of fractured bone, to thereby reside on the fixture 14 while mechanical reduction is achieved and/or reside on the fixture 14 while mechanical reduction fixing is achieved. The second orthotic brace 310 includes the flexibility to respond to translational and rotational forces applied to the fracture when attached to the humeral support carriage 26 and the radius/ulna support carriage 28 of the fixture 14.

As shown in FIGS. 44A to 44C, this aspect of the invention therefore provides a mechanical bone fracture reduction system 334 comprising the frame 22 (as previously described) that is sized and configured to support a bone fracture and the mechanical reduction mechanism 16 (as previously described) on the frame 22 that is sized and configured to apply to the bone fracture a mechanical force vector that moves the bone fracture into a desired anatomic orientation. The mechanical reduction mechanism 16 includes one or more locking mechanisms (as previously described) that are sized and configured to mechanically interact with the reduction mechanism 16 to maintain the desired anatomic orientation. The system 10 includes an orthotic brace 310 that is sized and configured to be fitted to a region of the bone fracture before, during, or after the reduction of the fracture by the reduction mechanism. The orthotic brace 310 includes a proximal brace component 312 that is sized and configured to be fitted to a proximal region of the fracture, a distal brace component 314 that is sized and configured to be fitted to a distal region of the fracture, and a strut 316 having a proximal region linked to the proximal brace component 312 and a distal region linked to the distal brace component 314. At least one of the proximal and distal regions comprises a linkage mechanism 318 permitting articulation of the respective brace component on the strut 316 within a range of rotational orientations in response to forces applied by the reduction mechanism. The respective region further includes a locking mechanism 320 to maintain a desired rotational orientation within the range to maintain the desired anatomic orientation.

The frame 22 can also carry a mechanical guidance mechanism 18 (as previously described) that is sized and configured to guide placement of one or more bone fixing devices 202 to maintain the desired anatomic orientation.

After reduction and/or fixing of the fracture (see FIG. 45), the second orthotic brace 310 is sized and configured to be removed from the fracture reduction mechanism 16 and thereafter worn by the individual, fully assembled to the fixed reduction, to maintain and/or improve the fixed reduction while healing occurs. For example, the technical features of the second orthotic brace 310 as described make it possible for the brace to adapt to the mechanical reduction forces applied by the exemplary fracture reduction mechanism 18 when reducing and fixing the fracture (see FIG. 44A). As previously demonstrated in FIGS. 41, 42, and 43, when attached to the exemplary fracture reduction mechanism 18 (as shown in FIG. 44A), the second orthotic brace 310 accommodates the independent application of all the mechanical force reduction vectors along and about all three anatomical reduction axes of the arm as previously described; namely, the ARPA, ARVA, and ARHA (shown in FIG. 12A). The strut 306 with the independent axial adjustment mechanism 324 and linkage mechanism 318 connected to each of the humeral brace component 312 and the radius/ulnar brace component 314 allows the brace components 312/314 to be manipulated independently when attached to the fracture reduction mechanism 18. The second orthotic brace 310 adapts to the myriad adjustments of the fracture reduction mechanism 18 when reducing and fixing the fracture.

More particularly, as shown in FIG. 44A, the exemplary fracture reduction mechanism 18 previously described (also see e.g. FIGS. 19A and 19B) includes a humeral support carriage 26 and a radius/ulna support carriage 28. The humeral support carriage 26 and radius/ulna support carriage 28 can be sized and configured to be temporarily secured to the humeral brace component 312 and the radius/ulna brace component 314 of the orthotic brace 310. In this arrangement, the humeral support carriage 26 and the radius/ulna support carriage 28 hold the humerus and radius/ulna within the orthotic brace 310 in the same orientation during mechanical reduction, and maintain this orientation after reduction during mechanical fixing of the reduction.

It can be appreciation that the form, fit, and function of the humeral brace component 312 and the radial/ulnar brace component 314 complement the form, fit, and function of the humeral support carriage 26 and the radius/ulna support carriage 28 of the mechanical reduction frame. For this reason, the second orthotic brace 310 can be sized and configured to be partially or fully assembled to the individual's arm and be temporarily secured, e.g., by straps, pins, or fasteners, to the humeral support carriage 26 and the radius/ulna support carriage 28 of the reduction frame prior to mechanical force, as previously described with respect to the first orthotic brace 300. The orthotic brace 310 can likewise be sized and configured, while partially or fully assembled to the individual's arm, to remain secured to the humeral support carriage 26 and the radius/ulna support carriage 28 during fixing of the reduced fracture. After fixing of the mechanically reduced mechanism 18, the orthotic brace 310 is released from the system fully assembled to the individual's arm, to be worn by the individual to maintain and/or improve the reduction, after fixing, while healing occurs (as shown in FIG. 45).

In the exemplary embodiment shown in FIGS. 44B and 44C, each of radius/ulna support carriage 28 and the humeral support carriage 26 includes an orthotic brace support mechanism 336 carried by the respective carriage 26/28. In the exemplary embodiment, the orthotic brace support mechanisms 336 for the carriages 24/26 are essentially identical.

Each orthotic brace support mechanism 336 includes female vice flange 338 that accommodates placement of a mating male flange 340 formed on the companion humeral brace component 312 or radius/ulna brace component 314. The female vice flange 338 includes a fixed flange member 342 and a movable flange member 344. The movable flange member 344 is secured by a threaded pin 346 opposite from the fixed flange member 342.

Rotation of the threaded pin 346 in one direction retracts the movable flange member 344 away from the fixed flange member 342 (see FIG. 44B). This enlarges the width of the female vice flange 338 to a dimension larger than the male flange 340, so that the male flange 340 can be fitted into the female vice flange 338. This, in turn, fits the companion brace component 312/314 to the respective carrier 26/28.

Rotation of the threaded pin 346 in the opposite direction advances the movable flange member 344 toward the fixed flange member 342 (see FIG. 44C). This reduces the width of the female vice flange 338 to fractionally engage the male flange 340 previously fitted into the female vice flange 338. This secures the male flange 340 by frictional engagement within the female vice flange 338. The companion brace component 312/314 is also thereby secured to the carriage 26/28. The companion brace component 312/314 thereby functions In this arrangement, the humerus support carriage 26 and the radius/ulna support carriage 28 comprise a mechanical component of the fracture reduction fixture 14, carried by the frame 22, and a removable component, i.e., the companion brace component 312/314 carried by the ambulatory orthotic brace 310.

The locking pins 320 and 326 on the strut 316 of the orthotic brace 310 are loosened (either before or after fitment on the respective carriage 26/28). This allows unimpeded articulation and axial separation of the humeral brace component 312 and the radius ulna brace component 314 while the mechanical force reduction assemblies of the fracture reduction mechanism 16 orient the humeral support carriage 26 and/or the radius/ulna support carriage 28 in a stepwise fashion to reduce the fracture.

Once the fracture has been mechanically reduced (and desirably fixed) by the mechanisms 16/18, the locking pins 320 and 326 on the strut 316 of the orthotic brace 310 are tightened to maintain and/or improve the mechanically achieved reduction and (if performed) fixing. The threaded pin 346 on each orthotic brace support mechanism is rotated to retract the movable flange member 344 away from the fixed flange member 342 (see FIG. 44B), to enlarge the width of the female vice flange 338, so that the respective orthotic brace component 312/314 can be removed from companion carrier 26/28.

As shown in FIG. 45, the individual wears the orthotic brace 310 while post-operative healing occurs. The orthotic brace 310 is now ambulatory. The ambulatory brace, oriented as a result of mechanical reduction forces applied in a stepwise systematic manner, serves to maintain the orientation of the bone structures after reduction and fixing as healing occurs.

VII. Methods of Mechanically Reducing and Fixing a Bone Fracture

A. Overview

Illustrative devices and systems for achieving a mechanical force reduction and fixing of a fracture have been described, for the purpose of illustration, in the context of reducing a supracondylar fracture. Next to be described are illustrative methods for mechanically reducing and fixing a fracture using the exemplary devices and systems.

The methods that will be described are applicable to all bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condular fracture), e.g. at, in, or near the elbow, or at, in, or near the knee. Still, as before explained in the context of previous descriptions, the technical features of the methods can be well exemplified and highlighted with respect to the fixing of supracondylar fractures of the elbow. For this reason, the methods will be described in this context. Nevertheless, it is to be appreciated that the methods that embody features of the invention are not restricted to supracondylar applications. It is to be appreciated that the disclosed methods are readily applicable for use in treating all types of bone fractures, simple or complex, of any bone type, in children or adults, anywhere in the body.

Figure 48:
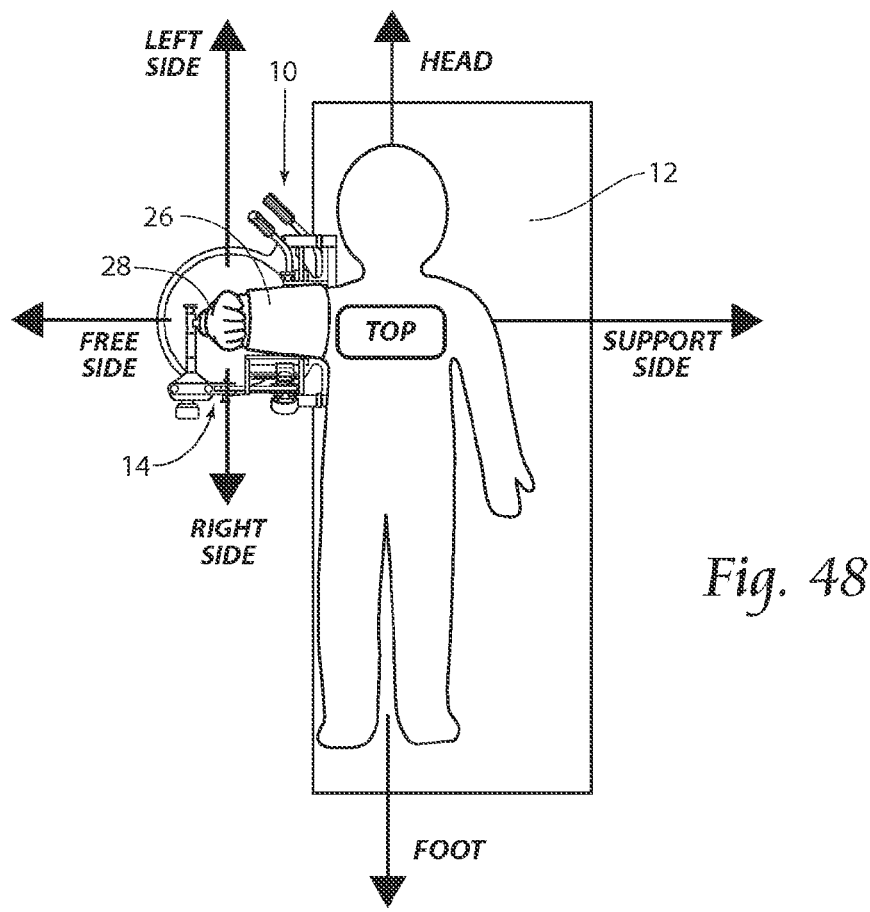
FIG. 48 is a top view of the system shown in FIGS. 18A and 18B in use, with an individual having a supracondylar fracture of a right arm laying in a prone position on the patient support platform, and the mechanical bone reduction fixture (shown in FIGS. 19A to 19F) supporting the humerus and forearm of the individual in a manner conducive for reducing the supracondylar fracture of the right arm.

In this context, and as shown in FIG. 48, the individual having a supracondylar fracture to be treated in their right arm is laid in a supine position on a patient platform 12, upon which a fracture reduction fixture 14 like that shown in FIGS. 19A and 19B is supported. Together, the patient platform 12 and the fracture reduction fixture 14 form the system 10.

The directional points of reference (Support Side, Free Side, Left, Right, Top, and Bottom), as used previously in FIGS. 18A/B to define the orientation of the system, annotate FIG. 48. Laying supine, the individual's anatomic anterior side faces Top-ward, and the individual's anatomic posterior side faces Bottom-ward. The individual's head (the anatomic superior or cephalad direction) faces Left-ward. The individual's feet (the anatomic inferior or caudal direction) faces Right-ward. For treatment of a right arm, the mount 20 is Support-ward, adjacent the individual's right arm side (the anatomic right lateral direction). The individual's other side (the anatomic left lateral direction) faces Free-ward. This orientation is also shown in FIG. 18C. It should be appreciated that, for treatment of a left arm, the individual's head (the anatomic superior or cephalad direction) faces Right-ward, and the individual's feet (the anatomic inferior or caudal direction) faces Left-ward (as shown in FIG. 18D). Thus, it can be seen how the structural directional points of reference in FIGS. 18A/B can be readily converted to anatomic direction points of reference relative to the individual being treated, if desired.

For the sake of consistency, subsequent description will continue to use the structural directional points of reference (Support Side, Free Side, Left, Right, Top, and Bottom) used in FIGS. 18A/B.

Figure 49:
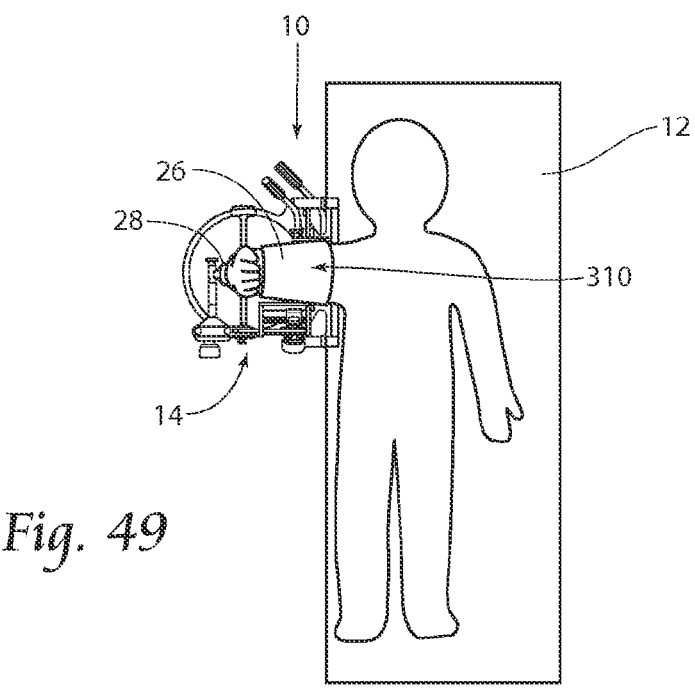
FIG. 49 is a top view of the system shown in FIGS. 18A and 18B in use, with an individual having a supracondylar fracture of a right arm laying in a prone position on the patient support platform, and the mechanical bone reduction fixture (shown in FIGS. 19A to 19F) supporting the humerus and forearm of the individual in a manner conducive for reducing the supracondylar fracture of the right arm, with the orthotic brace shown in FIGS. 42A and 42B also fitted in association with a mechanical bone reduction fixture during use, as shown in FIG. 44A.

The individual's right arm is oriented with the humeral support carriage 26 and a radius/ulna support carriage 28 of the fracture reduction fixture 14. In the exemplary embodiment (see FIG. 49), the orthotic brace 310 is either fully or partially assembled on the arm and temporarily secured to the humeral brace component 312 and a radius/ulnar brace component 314, as previously described.

B. Pre-Procedure Alignment

Prior to beginning the procedure, the fracture reduction fixture 14 is mounted to the patient platform for use. The components of the fracture reduction fixture 14 are placed in their neutral, or rest, positions. For the horizontal traction carriage 42 (see FIG. 44A), the rest position is fully translated over to the Support Side of the horizontal rail. For the vertical traction carriage 54 (see FIG. 44A), the rest position is fully translated over to the Bottom of the vertical rail 56. For the lateral translation carriage 64, the rest position is translating the support bed 66 to the middle of the cross bar and the parallel companion threaded cross bolt. For the rocking carriage 74, the rotation carriage, and the tilting carriage, the rest position is likewise in their centermost, neutral positions parallel to the Mechanical Axes of the fracture reduction fixture 14.

During the reduction procedure, the c-arm 272 can be oriented relative to the supracondylar region for lateral and a-p radiographic imaging of the supracondylar fracture, as shown, respectively, in FIGS. 46A and 47A. FIG. 46B shows a lateral image of the displaced distal and proximal bone regions of supracondylar fracture of a right arm, prior to reduction. FIG. 47B shows a lateral image of the displaced distal and proximal bone regions of supracondylar fracture of a right arm, prior to reduction.

Figure 50:
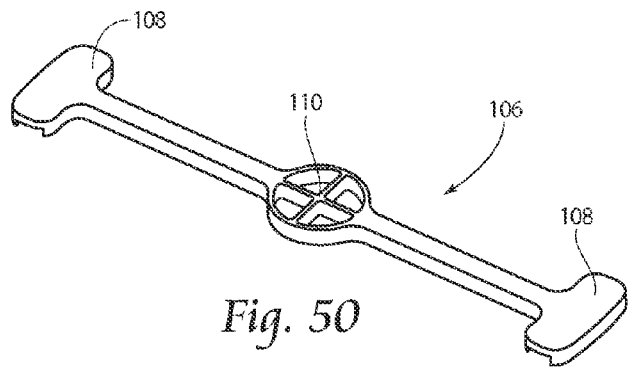
FIGS. 50 and 51 are respectively, perspective views of an a-p cross hair device and a lateral cross hair device that are used, with radiographic imaging, to align the mechanical bone reduction fixture (shown in FIGS. 19A to 19F) relative to the supracondylar fracture prior to reduction of the fracture.
Figure 51:
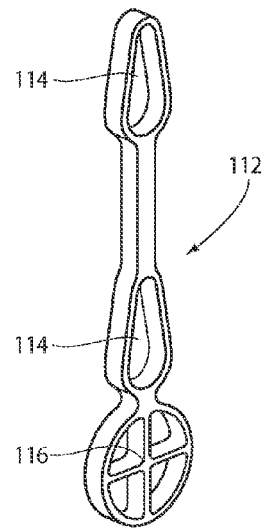
Figure 56:
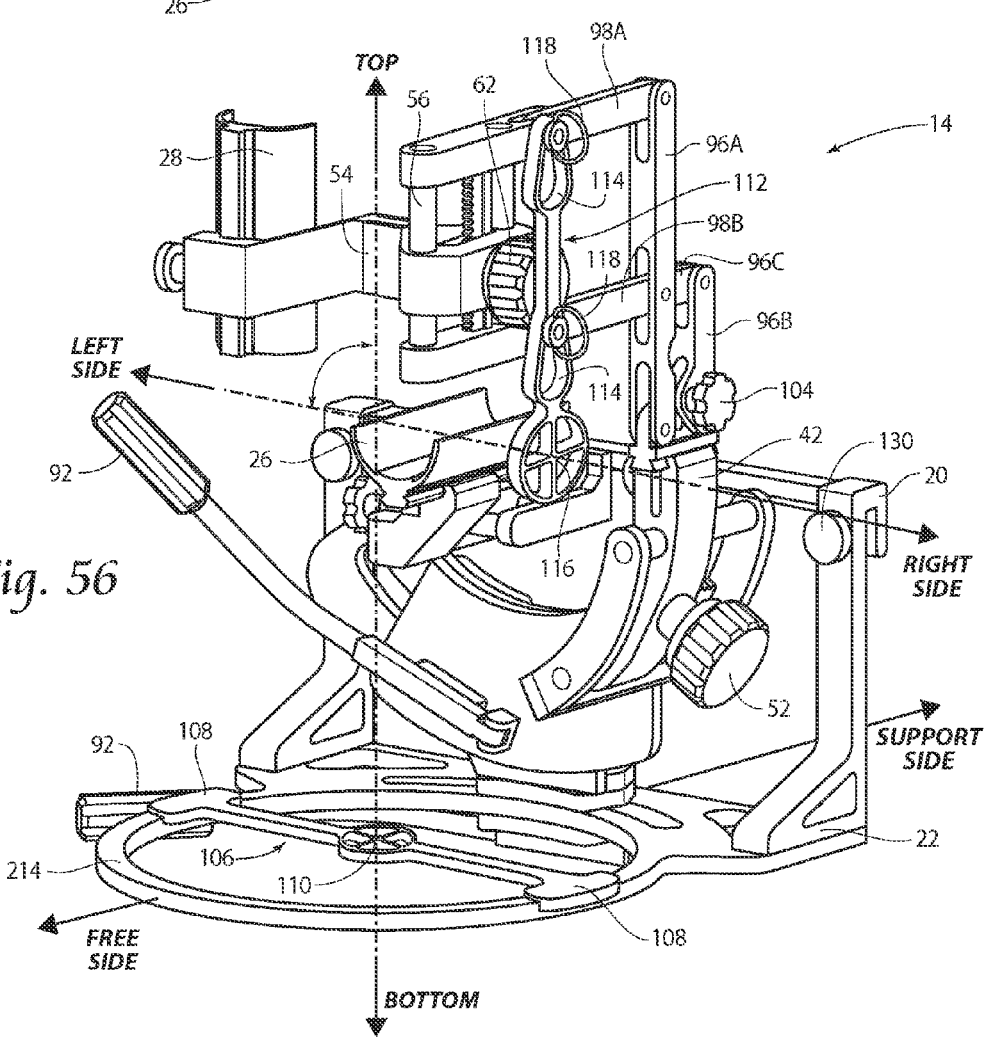
FIG. 56 is a Free Side perspective view of the mechanical bone reduction fixture shown in FIGS. 19A to 19F with the a-p cross hair device and a lateral cross hair device (shown, respectively, in FIGS. 50 and 51) in their correct positions to align, with the aid of radiographic imaging, the mechanical bone reduction fixture in a-p and lateral planes relative to the supracondylar fracture prior to reduction of the fracture.

The caregiver or surgeon uses a-p and lateral radiographic images to initially align the fractured supracondylar region carried by the fracture reduction fixture 14 relative to a central point of reference on the fracture reduction fixture 14, where central Mechanical Vertical and Horizontal Axes intersect (see FIG. 56). The central Mechanical Perpendicular axis also intersects this point. By aligning the fracture centrally along these axes by a-p radiographic imaging and by lateral radiographic imaging, the caregiver or surgeon will also initially align the mechanical components of the fixture 14 and orthotic brace 310 relative to these points of reference, for further reduction and fixing. FIGS. 50 and 51 illustrate exemplary devices to assist in this alignment.

Figure 52:
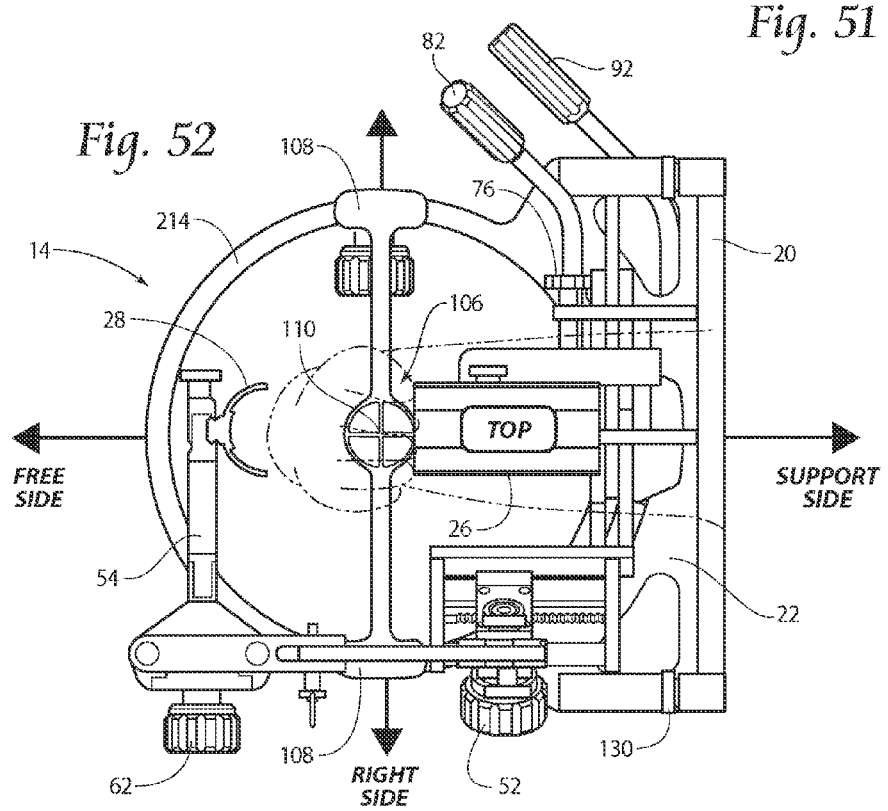
FIG. 52 shows the placement of the a-p cross hair device shown in FIG. 50 in a position to align the mechanical bone reduction fixture in an a-p plane relative to the supracondylar fracture prior to reduction of the fracture.

FIG. 50 shows an exemplary a-p crosshair device 106. The a-p crosshair device 106 generally comprises an elongated body having opposing ends that are spaced apart so that they will extend across the fixing alignment rail 214 (see FIG. 52). Each of the opposing ends form a flange 108 that allows the a-p crosshair device 106 to sit on the alignment rail 214. The a-p crosshair device 106 further comprises a crosshair section 110 that is centered on the elongated body. When spanning the fixing alignment rail 214, the crosshair section 110 aligns with the central Mechanical Vertical Axis of the fracture reduction fixture 14. The a-p crosshair device 106 is made of a radioluminescent material so that, during a-p radiographic imaging (see FIG. 53), the crosshair section 110 radiographically identifies the location of the central Mechanical Vertical Axes of the fraction reduction fixture 14. The circular geometry of the alignment rail 214 ensures that the central crosshair section 110 will always be centered on the center Mechanical Vertical Axis of the fracture reduction fixture 14, regardless of where the crosshair device 106 is placed across the fixing alignment rail 214.

Figure 54:
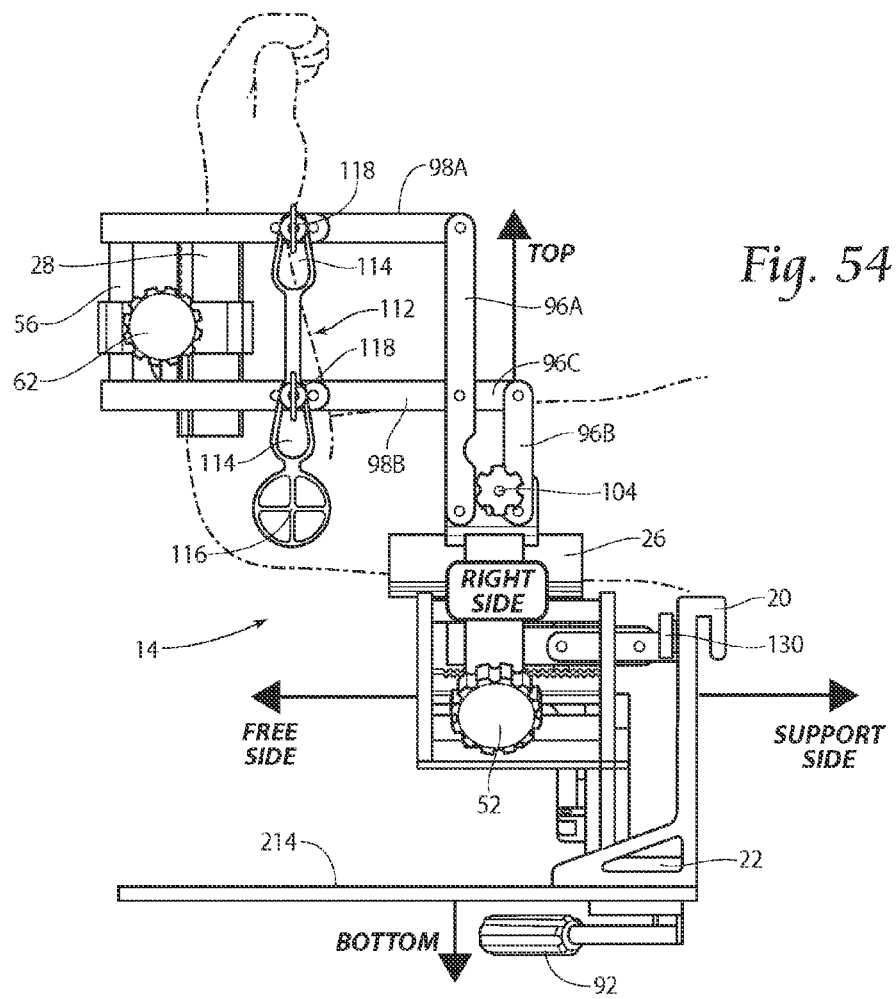
FIG. 54 shows the placement of the lateral cross hair device shown in FIG. 51 in a position to align the mechanical bone reduction fixture in a lateral plane relative to the supracondylar fracture prior to reduction of the fracture.

FIG. 51 depicts a lateral crosshair device 112. The lateral crosshair device 112 includes proximal and medial mounts 114 and a distal opening forming a crosshair section 116. The lateral crosshair device 112 is sized and configured so that the proximal and medial mounts 114 engage vertically aligned pins 118 formed on the horizontal top bar 98A and a horizontal bottom bar 98B of the second parallelogram 98 of the flexion/extension rotation mechanical force reduction assembly 40 (see FIG. 54). Engaged by the pins 118, the cross hair section 116 hangs below the second parallelogram 98 aligned with the central Mechanical Horizontal Axis of the fraction reduction fixture 14. The lateral crosshair device 112 is made of a radioluminescent material so that, during lateral radiographic imaging (see FIG. 55), the crosshair section 116 radiographically identifies the location of the central Mechanical Horizontal Axes of the fraction reduction fixture 14.

In use, the components of the fracture reduction fixture 14 are placed in their neutral, or rest, positions (as previously described). The humerus and radius/ulna (held by the orthotic brace 310, if desired) are secured to the fracture reduction fixture 14, respectively, on the humeral support carriage 26 and the radius/ulna support carriage 28. The a-p crosshair device 106 and the lateral cross hair device 112 are placed on the fracture reduction fixture 14 (see FIGS. 54 and 56).

Figure 53:
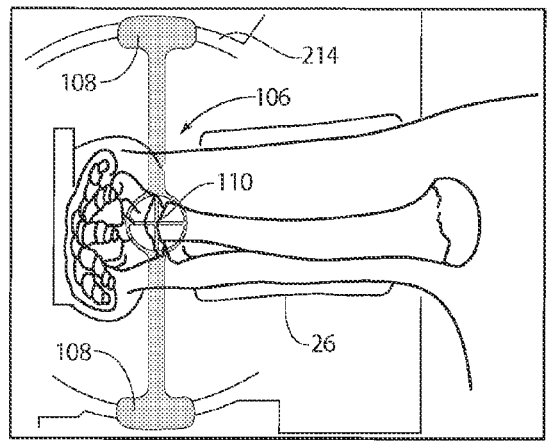
FIG. 53 is an illustration of an a-p radiographic image showing the alignment of the mechanical bone reduction fixture in an a-p plane relative to the supracondylar fracture prior to reduction of the fracture.

Using a-p radiograph imaging and the a-p crosshair device, the horizontal traction carriage 42 and lateral translation carriage 64 are moved to initially align the center of the fracture (viewed a-p) with the crosshair section 110 of the a-p crosshair device (see FIG. 53). This initial a-p alignment is maintained using the control mechanisms previous described.

Figure 55:
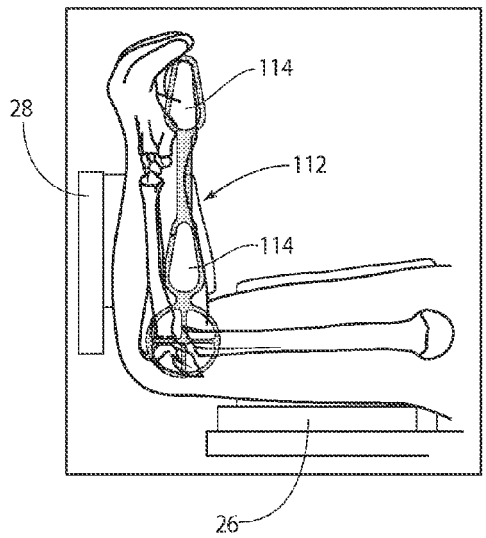
FIG. 55 is an illustration of a lateral radiographic image showing the alignment of the mechanical bone reduction fixture in a lateral plane relative to the supracondylar fracture prior to reduction of the fracture.

Using lateral radiograph imaging and the lateral crosshair device 112, the vertical traction carriage 54 is moved to initially align the center of the fracture (viewed laterally) with the crosshair section 116 of the lateral crosshair device 112 (see FIG. 55). This initial laterally aligned position is maintained using the control mechanisms previous described.

As shown in FIG. 56, the alignment of the axis of the a-p crosshair 110 and the lateral crosshair 116 intersect perpendicularly to one another, and centrally align the fracture reduction fixture 14 and the fracture relative to these coordinates. Once aligned with one another, the caregiver or surgeon can remove the a-p and lateral crosshair devices 106 and 112 and proceed with the reduction and fixing processes.

C. Mechanically Achieving Distal Traction

Figure 60:
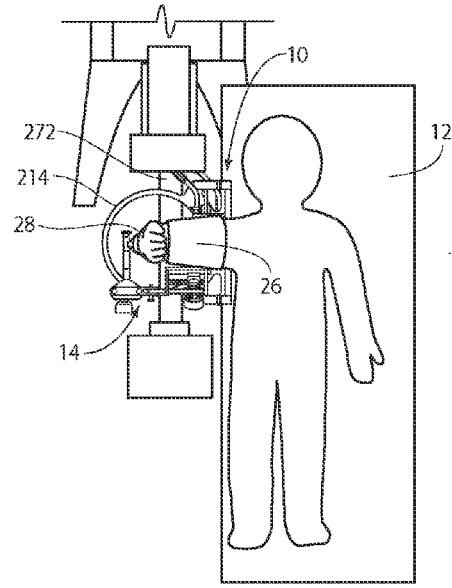
Figure 61:
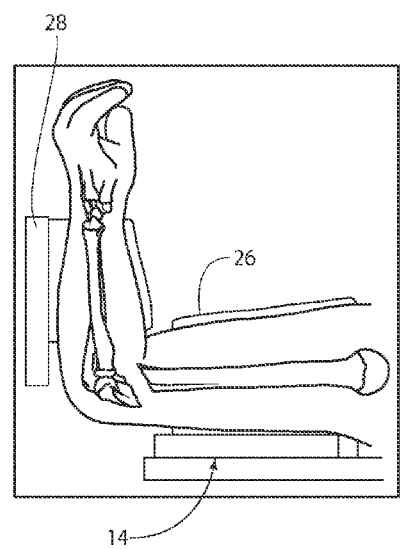

As FIGS. 57 to 59 show, the caregiver or surgeon operates the distal traction mechanical force reduction assembly 30, as previously described, to move the radius/ulna support carriage 28 in a Free-ward path in the horizontal plane (refer back to FIG. 20A). The humeral support carriage 26 remains stationary during Free-ward translation of the radius/ulna support carriage 28. Aided by lateral radiographic imaging (as FIGS. 57 and 58 show), the caregiver or surgeon mechanically applies linear Free-ward translation in a controlled fashion to move the radius/ulna support carriage 28 in a linear path Free-ward, laterally farther from the humeral support carriage 26. The distal traction mechanical force reduction assembly 30 mechanically achieves distal traction along the ARPA of the fracture reduction coordinate system of the supracondylar region (refer back to FIG. 12A), by separating the distal bone region and the proximal bone region along the ARPA (as confirmed by the lateral radiographic imaging shown in FIGS. 60 and 61), until a desired alignment in this first anatomic orientation is achieved. The caregiver or surgeon mechanically maintains the desired alignment in the first anatomic orientation, as previously described.

D. Mechanically Achieving Superior Traction

Figure 62:
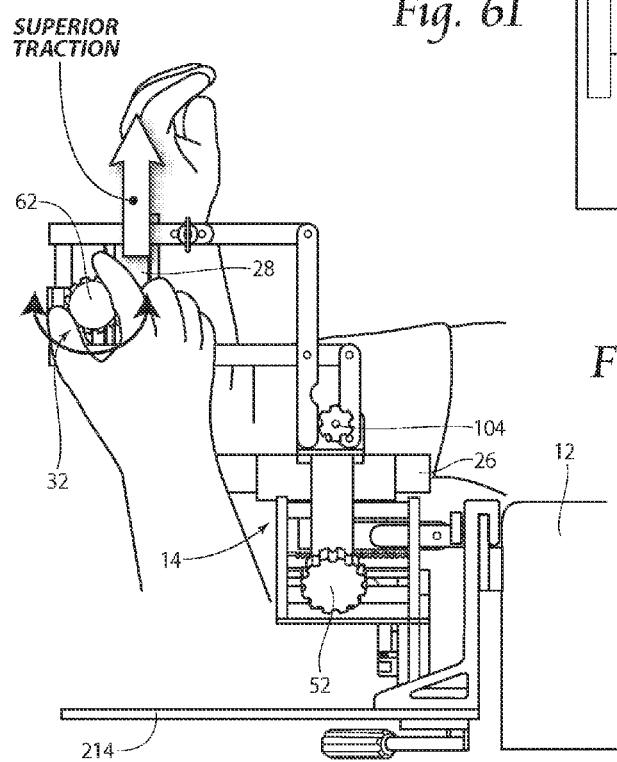
Figure 63:
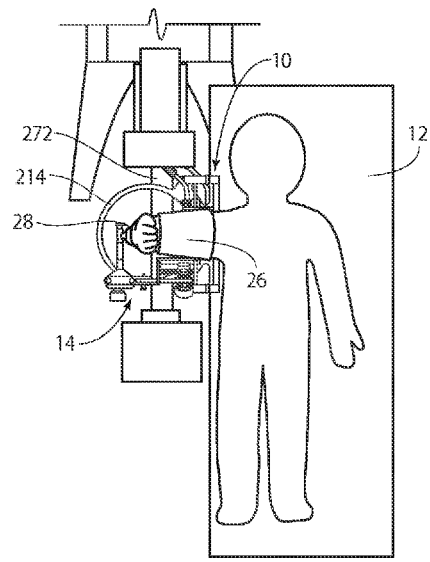
Figure 64:
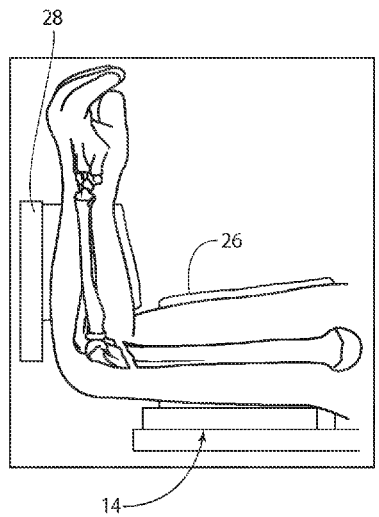

As FIG. 62 shows, the caregiver or surgeon operates the superior traction mechanical force reduction assembly 32, as previously described, to move the radius/ulna support carriage 28 in a linear Top-ward path in the vertical plane (refer back to FIG. 21A). The humeral support carriage 26 remains stationary during Top-ward translation of the radius/ulna support carriage 28. Aided by lateral radiographic imaging (as FIG. 63 shows), the caregiver or surgeon mechanically applies linear Top-ward translation in a controlled fashion to move the radius/ulna support carriage 28 in a linear path Top-ward, laterally farther from the humeral support carriage 26. The superior traction mechanical force reduction assembly 32 mechanically achieves superior traction along the ARVA (refer back to FIG. 13A) by separating the distal bone region and the proximal fracture region along the ARVA (as confirmed by the lateral radiographic image of FIG. 64), until a desired alignment in this second anatomic orientation is achieved. Because the first anatomic orientation is being mechanically maintained, achieving this second anatomic orientation does not alter the first-achieved anatomic orientation (in this case, distal traction). The caregiver or surgeon mechanically maintains the desired alignment in the second anatomic orientation as well, as previously described.

E. Mechanically Achieving Lateral Traction

Figure 65:
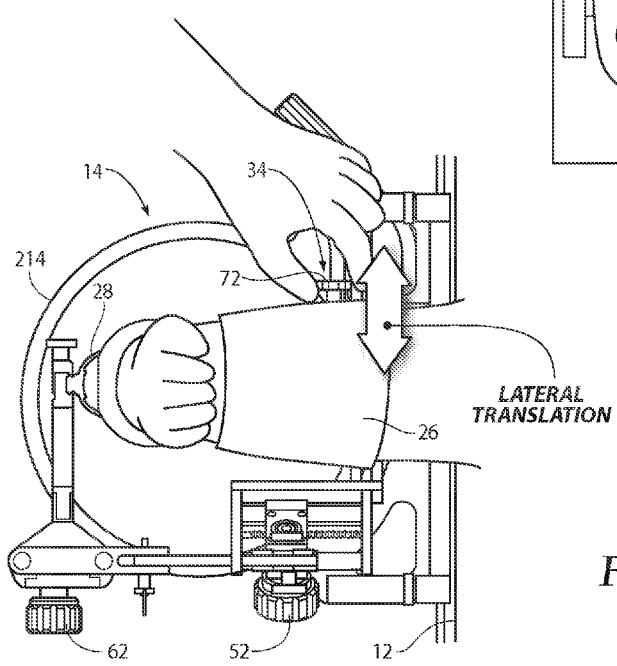
Figure 66:
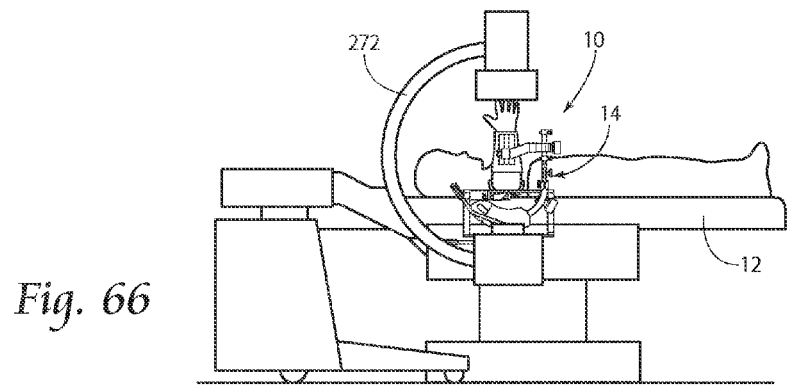
Figure 67:
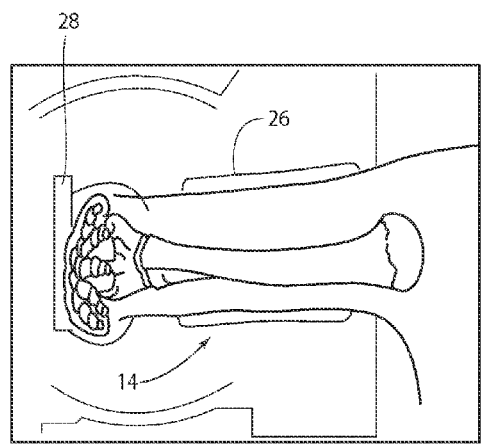

As FIG. 65 shows, the caregiver or surgeon operates the lateral traction mechanical force reduction assembly, as previously described, to move the humeral support carriage 26 in a linear path in a horizontal plane in a Right direction (Right-ward) and a Left direction (Left-ward) with respect to the support platform (refer back to FIG. 22A). The radius/ulna support carriage 28 remains stationary during linear Right-ward and Left-ward movement of the humeral support carriage 26. As previously explained, in the exemplary embodiment, the Right-ward and Left-ward translation is achieved in a micro-fashion (as FIG. 65 shows). Aided by a-p radiographic imaging (as FIG. 66 shows), the caregiver or surgeon mechanically applies linear Right-ward and Left-ward translation in a controlled fashion to move the humeral support carriage 26 in a linear path Right-ward and Left-ward. The superior traction mechanical force reduction assembly 32 mechanically achieves lateral traction along the ARHA (refer back to FIG. 14A) by mechanically returning proximal and distal bone regions that have been medially displaced along the ARHA back toward the native state of alignment (as confirmed by the a-p radiographic image of FIG. 67), until a desired alignment in this third anatomic orientation is achieved. Because the first and second anatomic orientations are being mechanically maintained, achieving this third anatomic orientation does not alter the first- and second-achieved anatomic orientations (in this case, distal traction and superior traction). The caregiver or surgeon mechanically maintains the desired alignment in the third anatomic orientation as well, as previously described.

F. Mechanically Achieving Varus/Valgus Rotation

Figure 68:
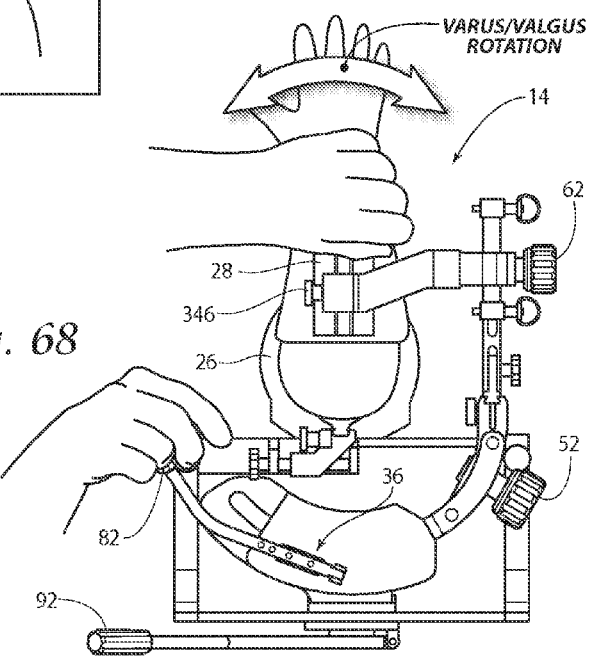
Figure 69:
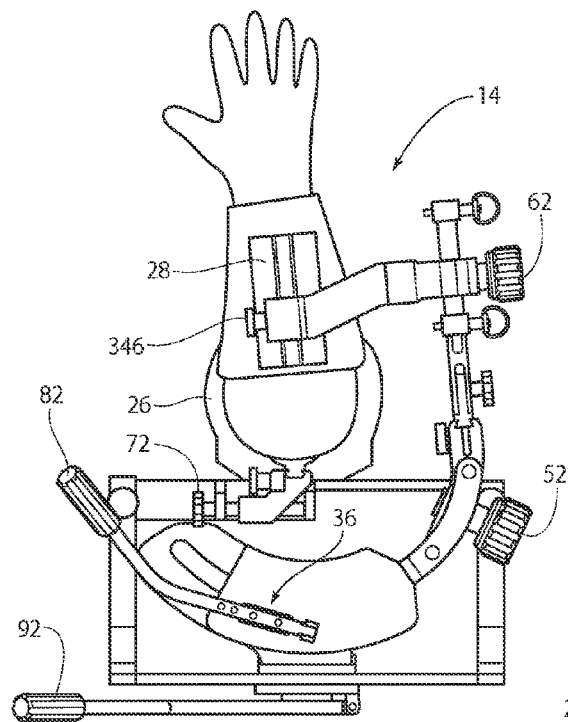
Figure 70:
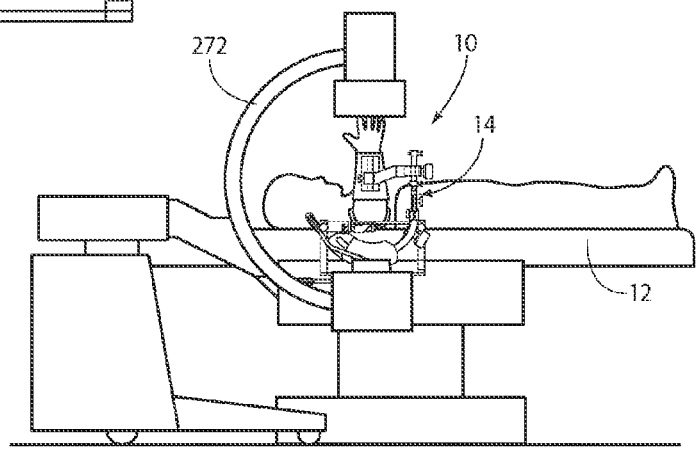
Figure 71:
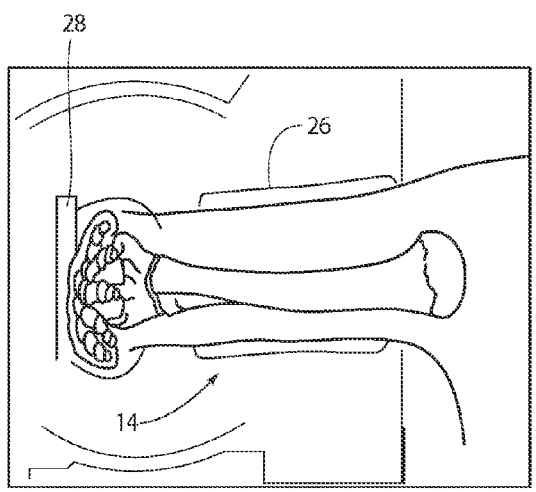

As FIGS. 68 and 69 show, the caregiver or surgeon operates the varus/valgus rotation mechanical force reduction assembly 36, as previously described, to tilt the radius/ulna carriage Right-wards and Left-wards (refer back to FIG. 23A). The humeral support carriage 26 remains stationary as the radius/ulna carriage tilts Left-wards and Right-wards. As previously explained, in the exemplary embodiment, the Front-ward and Back-ward translation is achieved in a macro-fashion (as FIGS. 68 and 69 show). Aided by a-p radiographic imaging (as FIG. 70 shows), the caregiver or surgeon mechanically applies Right-ward and Left-ward rotations in a controlled fashion to rock the radius/ulna carriage Right-ward and Left-ward. The varus/valgus rotation mechanical force reduction assembly 36 mechanically achieves varus/valgus rotation about the ARPA (refer back to FIG. 15A) by applying a rotational force vector (torque) about the ARPA to the fractured end of the distal bone region (held in the radius/ulna support carriage 28). The varus/valgus rotation force, mechanically applied by the varus/valgus rotation mechanical force reduction assembly 36, pivots the fractured end of the distal bone region about the longitudinal axis of the proximal bone region, to return the proximal and distal bone regions, which have been rotationally displaced due to the fracture, back toward the native state of alignment (as confirmed by the a-p radiographic image of FIG. 71), until a desired alignment in this fourth anatomic orientation is achieved, at which point the locking mechanism is operated. Because the first, second, and third anatomic orientations are being mechanically maintained, achieving this fourth anatomic orientation does not alter the first-, second-, or third-achieved anatomic orientations (in this case, distal traction, superior traction, and lateral traction). The caregiver or surgeon mechanically maintains the desired alignment in the fourth anatomic orientation as well, as previously described.

G. Mechanically Achieving Pronation/Supination Rotation

Figure 75:
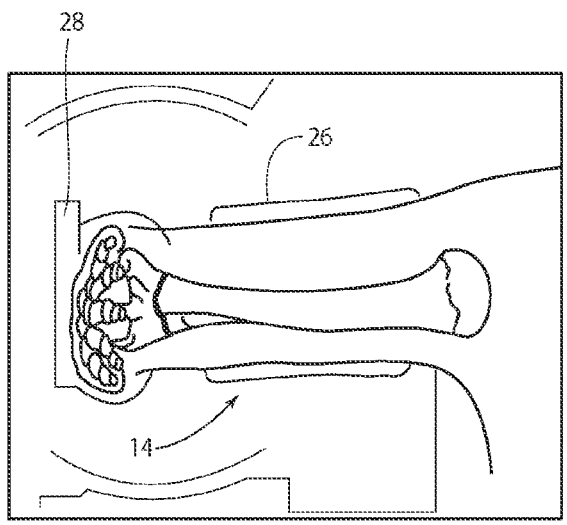

As FIG. 72 shows, the caregiver or surgeon operates the pronation/supination rotation mechanical force reduction assembly 38, as previously described, to rotate or swing the radius/ulna carriage Left-ward and Right-ward about the Top-to-Bottom virtual center of rotation (refer back to FIG. 24C). The humeral support carriage 26 remains stationary as the radius/ulna carriage swings Left-wards and Right-wards. As previously explained, in the exemplary embodiment, the Right-ward and Left-ward translation is achieved in a micro-fashion (as FIG. 72 shows). Aided by a-p radiographic imaging (as FIG. 73 shows), the caregiver or surgeon mechanically applies Right-ward and Left-ward rotations in a controlled fashion to swing the radius/ulna carriage Right-ward and Left-ward. The pronation/supination rotation mechanical force reduction assembly 38 mechanically achieves pronation/supination rotation about the ARVA (refer back to FIG. 16A) by swinging the radius/ulna support carriage 28 in an arcuate path in a horizontal plane Right-ward and Left-ward about the Top-to-Bottom virtual center of rotation axis relative to the stationary humeral support carriage 26. As the radius/ulna support carriage 28 swings Right-ward and Left-ward about the Top-to-Bottom virtual center of rotation axis relative to stationary humeral support carriage 26, a rotational force vector (torque) is applied about the ARVA to the fractured end of the distal bone region (held in the radius/ulna support carriage 28). The pronation/supination rotation force, mechanically applied by the pronation/supination rotation mechanical force reduction assembly 38, pivots the fractured end of the distal bone region about the longitudinal axis of distal bone region, back toward the native state of alignment (as confirmed by a-p radiographic imaging as shown in FIGS. 74 and 75), until a desired alignment in this fifth anatomic orientation is achieved, at which time the locking mechanism is actuated. Because the first, second, third, and fourth anatomic orientations are being mechanically maintained, achieving this fifth anatomic orientation does not alter the first-, second-, third-, or fourth-achieved anatomic orientations (in this case, distal traction, superior traction, lateral traction, and varus/valgus rotation). The caregiver or surgeon mechanically maintains the desired alignment in the fifth anatomic orientation as well, as previously described.

H. Mechanically Achieving Flexion/Extension Rotation

Figure 76:
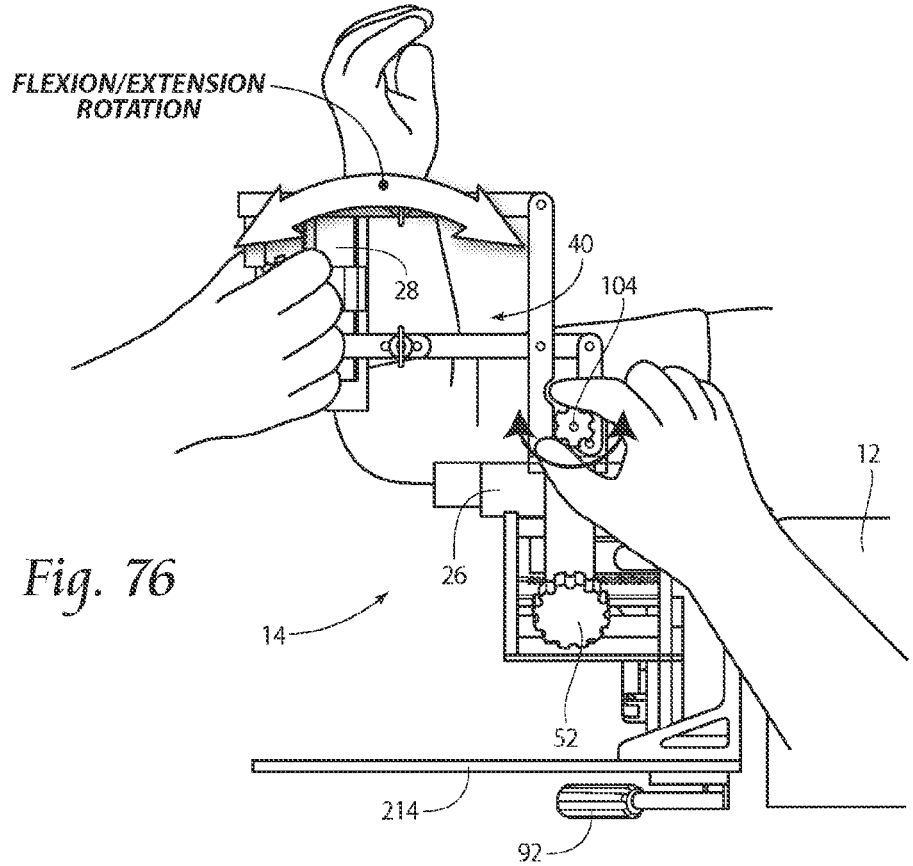
Figure 77:
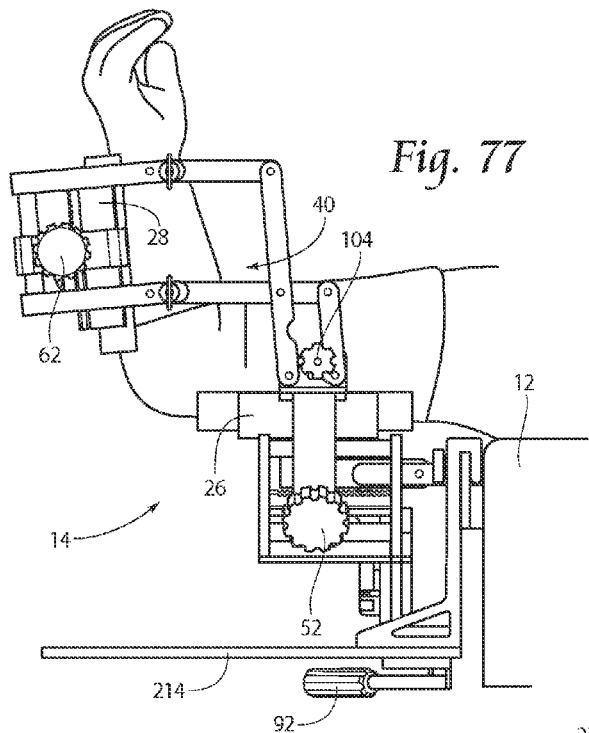
Figure 78:
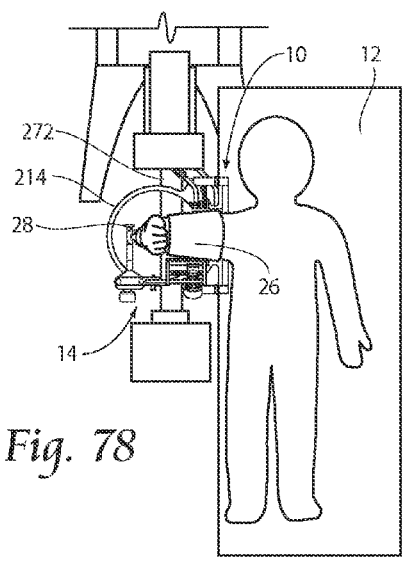
Figure 79:
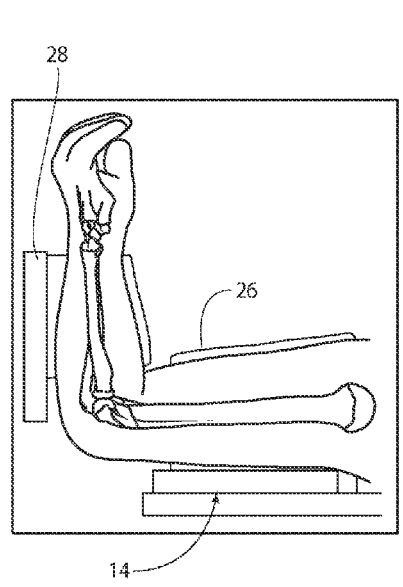

As FIGS. 76 and 77 show, the caregiver or surgeon operates the flexion/extension rotation mechanical force reduction assembly 40, as previously described, to tilt the radius/ulna support carrier Free-ward (refer back to FIG. 25A). The humeral support carriage 26 remains stationary as the radius/ulna carriage tilts Free-ward. As previously explained, in the exemplary embodiment, the Free-ward translation is achieved in a macro-fashion (as FIGS. 76 and 77 show). Aided by lateral radiographic imaging (as FIG. 78 shows), the caregiver or surgeon mechanically applies Free-ward rotation in a controlled fashion to swing the radius/ulna carriage Free-ward. The flexion/extension rotation mechanical force reduction assembly 40 mechanically achieves flexion/extension rotation about the ARHA (refer back to FIG. 17A) by tilting the radius/ulna support carriage 28 Free-ward relative to the stationary humeral support carriage 26. As the radius/ulna support carriage 28 tilts Free-ward relative to stationary humeral support carriage 26, a rotational force vector (torque) is applied about the ARHA to the fractured end of the distal bone region (held in the radius/ulna support carriage 28). The flexion/extension rotation force, mechanically applied by the flexion/extension rotation mechanical force reduction assembly 40, tilts the fractured end of the distal bone region about the longitudinal axis of the proximal bone region, to return the proximal and distal bone regions, which have been rotationally displaced due to the fracture, back toward the native state of alignment (as confirmed by the lateral radiographic image of FIG. 79), until a desired alignment in this sixth anatomic orientation is achieved, at which point the locking mechanism is actuated. Because the first, second, third, fourth, and fifth anatomic orientations are being mechanically maintained, achieving this sixth anatomic orientation does not alter the first-, second-, third-, fourth-, or fifth-achieved anatomic orientations (in this case, distal traction, superior traction, lateral traction, varus/valgus rotation, and pronation/supination rotation). The caregiver or surgeon mechanically maintains the desired alignment in the six anatomic orientation as well, as previously described.

I. Fracture Reduction Review

To summarize, the fracture reduction method, as just described, includes (i) supporting on a frame a body region having the bone fracture, (ii) operating a first reduction mechanism on the frame to apply to the bone fracture a first predefined force reduction vector that returns the bone fracture to a corrective alignment in a first anatomic orientation, (iii) mechanically maintaining the corrective alignment in the first anatomic orientation, (iv) independent of (ii) and (iii), operating a second reduction mechanism on the frame to apply a second predefined force reduction vector that returns the bone fracture to a corrective alignment in a second anatomic orientation different than the first anatomic orientation without altering the corrective alignment in the first anatomic orientation, and (v) mechanically maintaining the corrective alignment in the second anatomic orientation.

The force reduction assemblies carried by the system make possible a mechanically-achieved complete composite reduction of a complex fracture. In the exemplary case of a supracondylar fracture, the method can the operation of up to six force reduction assemblies, corresponding to the up to six mechanical force reductions identified for a supracondylar fracture; namely, (i) a distal traction mechanical force reduction assembly 30 (ii) a superior traction mechanical force reduction assembly 32; (iii) a lateral traction mechanical force reduction assembly; (iv) a varus/valgus rotation mechanical force reduction assembly 36; (v) a pronation/supination rotation mechanical force reduction assembly 38; and (vi) a flexion/extension rotation mechanical force reduction assembly 40.

Reduction can proceed in a systematic, stepwise fashion, by applying predefined force reduction vectors one at a time, and mechanically maintaining one corrective alignment before proceeding with the next, until alignment in all desired anatomic orientations is achieved. Alternatively, however, the caregiver or surgeon can chose to proceed to apply two or more predefined force reduction vectors concurrently, to achieve concurrent corrective alignments in more than one anatomic orientation at the same time, and mechanically maintaining the concurrently-achieved corrective alignments. The former, stepwise approach is preferred, particularly when the predefined force reduction vectors are applied with manual control and/or guidance. Still, it should be appreciated that the technical features of the invention can be achieved without a stepwise approach.

J. Mechanically Achieving Reduction Fixing Guidance

Figure 80:
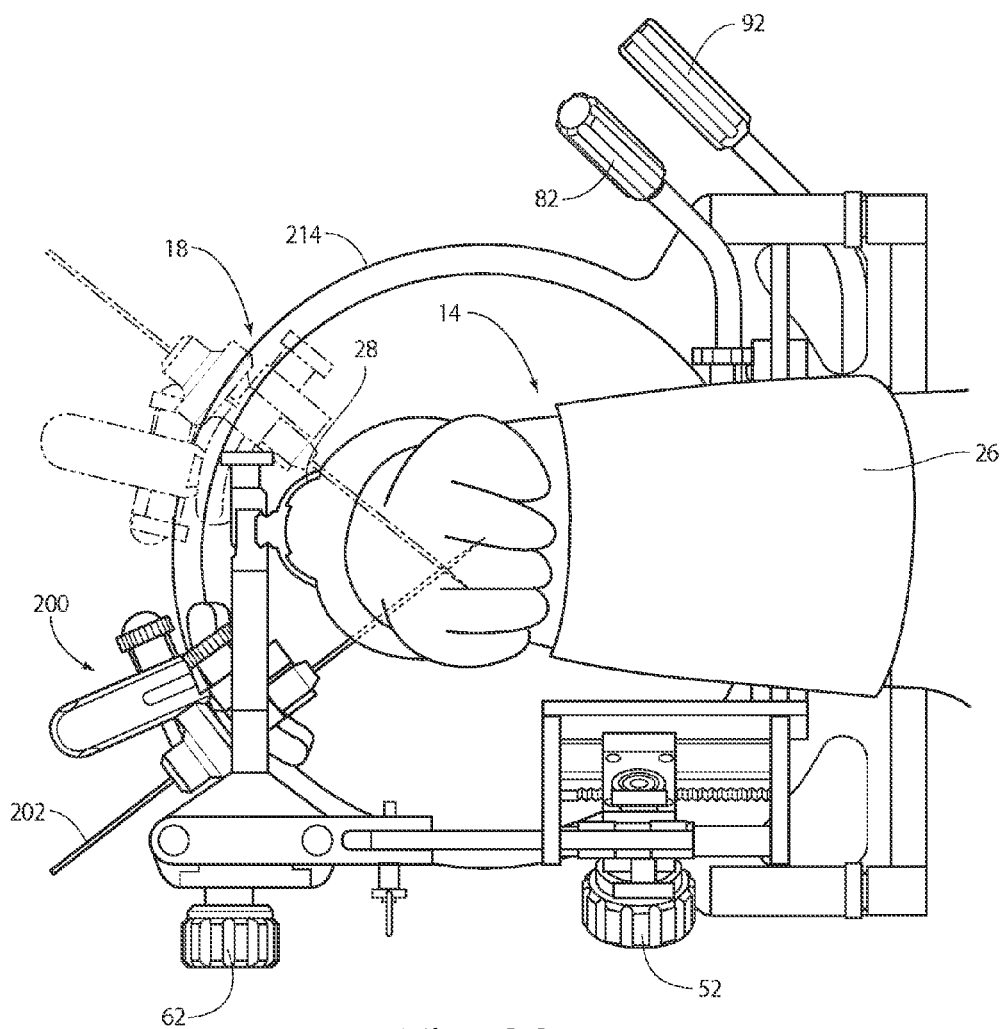

Once mechanical force reduction is achieved, the surgeon or caregiver can, without removal of the orthotic brace 310 and without otherwise altering the composite reduction mechanically achieved, proceed to operate a mechanical bone fixing instrument or tool on the fracture reduction fixture 14 like that shown in FIGS. 27 to 35. As shown in FIG. 80, by operating the mechanical bone fixing instrument or tool, the caregiver or surgeon guides insertion of one or more bone fixing devices to maintain the desired alignment in the anatomic orientations, as previously described, and as generally shown for the purpose of illustration in FIG. 80.

To summarize, the method for mechanically guiding a fixing of a bone fracture reduction comprising (i) supporting on a frame a body region having bone fracture reduction, (ii) providing a guide assembly on the frame including a bone fixing device guide 208 that defines a guide path along which a bone fixing device can be advanced into a region of the reduced bone fracture, the guide assembly including a linkage system that couples the bone fixing device guide 208 to the frame for articulation of the guide path among a plurality of desired orientations with respect to the reduced bone fracture, (iii) mechanically maintaining a desired orientation, (iv) placing the bone fixing device through the guide into the bone fracture reduction to fix the bone fracture reduction.

In a representative implementation of (ii) and (iii), the linkage system includes a first link that articulates the bone fixing device guide 208 in a first plane, including a mechanism that is sized and configured to mechanically interact with the first link to maintain a desired articulation in the first plane, and a second link that articulates the bone fixing device guide 208 in a second plane different than the first plane, including a mechanism that is sized and configured to mechanically interact with the second link to maintain a desired articulation in the second plane without altering the desired articulation in the first plane. In a representative implementation of (ii) and (iii), the linkage system can also include a third link that articulates the bone fixing device guide 208 in a third plane that intersects one of the first and second planes at an angle, including a mechanism that is sized and configured to mechanically interact with the third link to maintain a desired articulation in the third plane without altering the desired articulations in the first and second planes.

Multiple bone fixing devices can be inserted at different articulations into the bone fracture reduction.

Desirably, at least one radio-opaque guide is provided parallel to and axially aligned with the path of the bone fixing device in at least one of the respective planes. In this arrangement, before placing the bone fixing device through the guide, a radiographic image is generated of the radio-opaque guide relative to the bone fracture reduction As before explained, either the first or second plane can comprise a horizontal plane, a vertical plane, or a plane that intersects a horizontal or vertical plane at an angle.

K. Conclusion

Once mechanically guided fixing of the reduced bone fracture is achieved, the orthotic brace 310 can be released from the reduction frame, as FIG. 45 shows, without altering the orientation of bone structures in the reduced and fixed fracture. The individual is free to ambulate as healing occurs and the supracondylar region returns to its native state prior to injury.

Each of the mechanical force reduction assemblies is sized and configured to independently mechanically manipulate the arm resting in the humeral support carriage 26 and the radius/ulna support carriage 28. Each mechanical force reduction assembly functions independently of the other mechanical force reduction assemblies, to independently apply and maintain one of the prescribed mechanical reduction forces to the fracture. Concurrently, the mechanical force reduction assemblies mechanically apply and maintain a plurality of independent mechanical reduction forces, to thereby mechanically reduce the fracture in the desired reduction planes.

In the context of reducing a supracondylar fracture, there are six mechanical force reduction assemblies. The six mechanical force reduction assemblies correspond to six mechanical force reductions identified for a supracondylar fracture. In this context, the mechanical force reduction assemblies carried by the support platform comprise (i) a distal traction mechanical force reduction assembly 30; (ii) a superior traction mechanical force reduction assembly 32; (iii) a lateral traction mechanical force reduction assembly; (iv) a varus/valgus rotation mechanical force reduction assembly 36; (v) a pronation/supination rotation mechanical force reduction assembly 38; and (vi) a flexion/extension rotation mechanical force reduction assembly 40. Concurrently, the six mechanical force reduction assemblies carried by the system make possible a mechanically-achieved complete composite reduction of a supracondylar fracture and a mechanically guided fixing of the mechanically-achieved complete composite reduction.

L. Robotic/Computer Control

Figure 81:
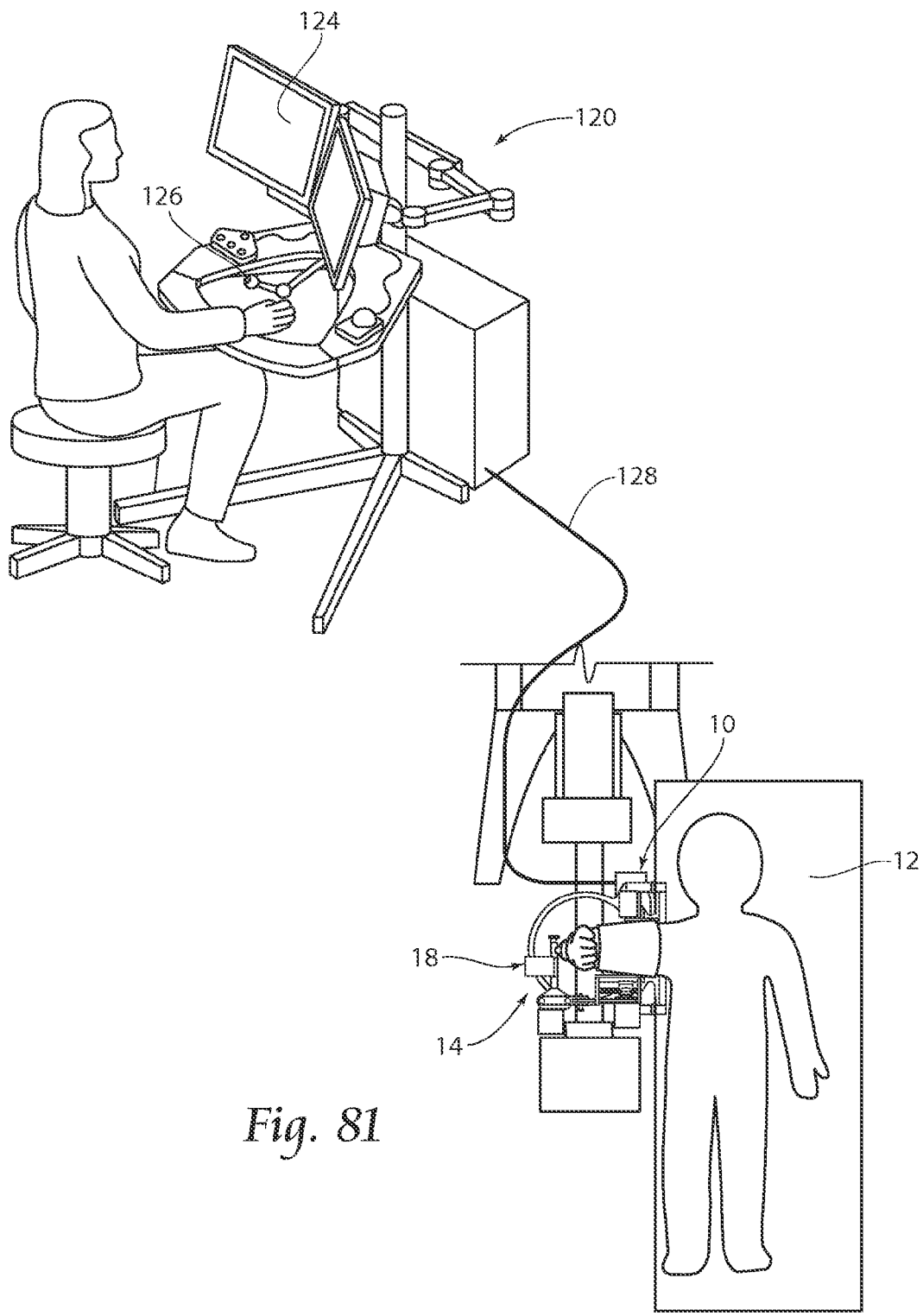
FIG. 81 is a perspective view of a system that includes robotic/computer control for achieving mechanical force reduction of a bone fracture by the application of force reduction vectors.

A fracture reduction system comprising one or more mechanical force reduction assemblies 30, 32, 34, 36, 38, and 40 and/or mechanical reduction fixing guidance systems 200 can include a robotic/computer control system 120 (see FIG. 81). The robotic/computer control system 120 includes a remote control console 122 that includes a radiographic image viewer 124 coupled to the c-arm 272 to facilitate imaging, as well as one or more instrument drivers 126 coupled by a communication link 128 to the mechanical force reduction assemblies 30, 32, 34, 36, 38, and 40 and/or mechanical reduction fixing guidance systems 200 carried by the system 120. The communication link 128 transfers control signals from the instrument drivers 126 to the mechanical force reduction assemblies 30, 32, 34, 36, 38, and 40 and/or mechanical reduction fixing guidance systems 200. The control signals operate the mechanical force reduction assemblies and/or mechanical reduction fixing guidance mechanisms 30, 32, 34, 36, 38, and 40 in the manners described, under radiographic image guidance. The fracture reduction system 10 comprising a robotic/computer control system 120 makes it possible to achieve, mechanically and under precise, robotic/computer control, a complete composite reduction of a fracture and/or a mechanically guided fixing of a mechanically-achieved complete composite reduction of a fracture.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A system for fixing a reduced bone fracture comprising
a frame that is sized and configured to support a reduced bone fracture of an individual,
a guide assembly on the frame including a bone fixing device guide that defines a guide path along which a bone fixing device can be advanced into a region of the reduced bone fracture, the guide assembly including a linkage system that couples the bone fixing device guide to the frame for articulation of the guide path among a plurality of desired orientations with respect to the reduced bone fracture
wherein the linkage system includes a first link that articulates the bone fixing device guide in a first plane, including a mechanism that is sized and configured to mechanically interact with the first link to maintain a desired articulation in the first plane, and a second link that articulates the bone fixing device guide in a second plane different than the first plane, including a mechanism that is sized and configured to mechanically interact with the second link to maintain a desired articulation in the second plane without altering the desired articulation in the first plane,
a guide bushing including an interior channel for passing a bone fixing device, the guide bushing being sized and configured to be handled separate from the guide assembly for insertion into the guide path of the bone fixing device guide at the instance of use and for separation from the guide path after use, and
packaging that maintains the guide bushing in a sterile condition prior to insertion into the guide path.

2. A system according to claim 1
wherein the interior channel includes an entrance end for receiving the bone fixing device for passage, the entrance end comprising a funnel shaped entrance surface that directs the bone fixing device directly into the interior channel, wherein the funnel shaped entrance surface shields contact with the interior channel prior to use.

3. A system according to claim 1
wherein the guide bushing is disposable.

4. A system according to claim 1
wherein the guide bushing can be returned to a sterile condition and repackaged after use.

5. A system according to claim 1
wherein the linkage system includes a third link that articulates the bone fixing device guide in a third plane that intersects one of the first and second planes at an angle, including a mechanism that is sized and configured to mechanically interact with the third link to maintain a desired articulation in the third plane without altering the desired articulations in the first and second planes.

6. A system according to claim 1
further including at least one fracture reduction mechanism on the frame that is sized and configured to apply at least one mechanical force vector to maintain the reduced bone fracture in at least one desired anatomic orientation during articulation of the guide path of the bone fixing device guide.

7. A system according to claim 1
further including an orthotic brace that is sized and configured to be fitted on the frame to a region of the reduced bone fracture.

8. A system according to claim 1
wherein the frame is sized and configured to support a reduced supracondylar fracture.

9. A system according to claim 1
wherein the bone fixing device comprises a pin.

10. A method for fixing a reduced bone fracture comprising
providing a frame that is sized and configured to support a reduced bone fracture of an individual,
providing on the frame a guide assembly including a bone fixing device guide that defines a guide path along which a bone fixing device can be advanced into a region of the reduced bone fracture, the guide assembly including a linkage system that couples the bone fixing device guide to the frame for articulation of the guide path among a plurality of desired orientations with respect to the reduced bone fracture,
articulating of the guide path of the bone fixing device guide into a desired orientation with respect to the reduced bone fracture,
providing separate from guide assembly a guide bushing in a sterile condition within a package, the guide bushing including an interior channel for passing a bone fixing device, the guide bushing being sized and configured to be handled separate from the guide assembly for insertion into the guide path of the bone fixing device guide at the instance of use and for separation from the guide path after use,
either before, during, or after the articulating, removing the guide bushing in a sterile condition from the packaging and inserting the guide bushing in a sterile condition into the guide path,
after the articulating, passing a bone fixing device through the interior channel into a region of the reduced bone fracture to fix the reduced bone fracture, and
after fixing the reduced bone fracture, removing the guide bushing from the guide assembly.

11. A method according to claim 10
after removing the guide bushing, disposing of the guide bushing.

12. A method according to claim 10
after removing the guide bushing, sterilizing the guide bushing and placing the guide bushing in a sterile condition within a package for reuse.

13. A method according to claim 10
wherein fixing the reduced bone fracture includes articulating the guide path into more than one desired orientation and, at each desired orientation, passing a bone fixing device through the interior channel into a region of the reduced bone fracture to fix the reduced bone fracture.

14. A method according to claim 10
further including fitting an orthotic brace to a region of the bone fracture before, during or after the fixing.

15. A method according to claim 10 further including
before, during, or after the fixing, attaching an orthotic brace to a carrier on the frame in either a partially or fully assembled condition to a region of the bone fracture, and
after fixing the reduced bone fracture and assembly of the orthotic brace to the region of the reduced bone fracture, releasing the orthotic brace from the carrier, wherein the orthotic brace can be worn by the individual to maintain and/or improve the fixed reduction while healing occurs.

16. A method according to claim 10
wherein the bone fracture involves an arm including the humerus and/or forearm and/or wrist; or involves a leg including the tibia and/or fibula; or involves articulating condyles including at, in, or near the elbow, or at, in, or near the knee.

17. A method according to claim 10
wherein the bone fracture comprises a supracondylar fracture.

\* \* \* \* \*